US008664192B2

(12) United States Patent
Croce

(10) Patent No.: US 8,664,192 B2
(45) Date of Patent: *Mar. 4, 2014

(54) **MUTATOR ACTIVITY INDUCED BY MICRORNA-155 (*MIR-155*) LINKS INFLAMMATION AND CANCER**

(75) Inventor: Carlo M. Croce, Columbus, OH (US)

(73) Assignee: The Ohio State University, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/414,084

(22) Filed: Mar. 7, 2012

(65) Prior Publication Data

US 2013/0065938 A1 Mar. 14, 2013

Related U.S. Application Data

(60) Provisional application No. 61/449,854, filed on Mar. 7, 2011.

(51) Int. Cl.
*C12N 15/11* (2006.01)
*C12Q 1/68* (2006.01)

(52) U.S. Cl.
USPC .......................................... 514/44 A; 435/6.1

(58) Field of Classification Search
None
See application file for complete search history.

(56) References Cited

U.S. PATENT DOCUMENTS

| 4,172,124 A | 10/1979 | Koprowski et al. |
| 4,196,265 A | 4/1980 | Koprowski et al. |
| 4,608,337 A | 8/1986 | Croce |
| 4,693,975 A | 9/1987 | Kozbor et al. |
| 4,701,409 A | 10/1987 | Croce |
| 5,015,568 A | 5/1991 | Tsujimoto et al. |
| 5,149,628 A | 9/1992 | Croce |
| 5,198,338 A | 3/1993 | Croce |
| 5,202,429 A | 4/1993 | Tsujimoto et al. |
| 5,459,251 A | 10/1995 | Tsujimoto et al. |
| 5,506,106 A | 4/1996 | Croce et al. |
| 5,506,344 A | 4/1996 | Tsujimoto et al. |
| 5,523,393 A | 6/1996 | Tsujimoto et al. |
| 5,567,586 A | 10/1996 | Croce |
| 5,595,869 A | 1/1997 | Tsujimoto et al. |
| 5,633,135 A | 5/1997 | Croce et al. |
| 5,633,136 A | 5/1997 | Croce et al. |
| 5,674,682 A | 10/1997 | Croce et al. |
| 5,688,649 A | 11/1997 | Croce et al. |
| 5,695,944 A | 12/1997 | Croce et al. |
| 5,928,884 A | 7/1999 | Croce et al. |
| 5,939,258 A | 8/1999 | Croce et al. |
| 5,985,598 A | 11/1999 | Russo et al. |
| 6,040,140 A | 3/2000 | Croce et al. |
| 6,130,201 A | 10/2000 | Croce et al. |
| 6,187,536 B1 | 2/2001 | Weinberg et al. |
| 6,242,212 B1 | 6/2001 | Croce et al. |
| 6,255,293 B1 | 7/2001 | Kimchi |
| 6,258,541 B1 | 7/2001 | Chapkin et al. |
| 6,774,217 B1 | 8/2004 | Croce et al. |
| 6,924,414 B2 | 8/2005 | Croce et al. |
| 7,060,811 B2 | 6/2006 | Aldaz et al. |
| 7,141,417 B1 | 11/2006 | Croce et al. |
| 7,175,995 B1 | 2/2007 | Russo et al. |
| 7,217,568 B2 | 5/2007 | Jamieson et al. |
| 7,220,834 B2 | 5/2007 | Croce et al. |
| 7,232,806 B2 | 6/2007 | Tuschl et al. |
| 7,390,792 B2 | 6/2008 | Srivastava et al. |
| 7,585,969 B2 | 9/2009 | Stoffel et al. |
| 7,592,441 B2 | 9/2009 | Bentwich et al. |
| 7,618,814 B2 | 11/2009 | Bentwich et al. |
| 7,642,348 B2 | 1/2010 | Bentwich et al. |
| 7,667,090 B2 | 2/2010 | Croce |
| 7,670,840 B2 | 3/2010 | Croce et al. |
| 7,709,616 B2 | 5/2010 | Bentwich et al. |
| 7,723,030 B2 | 5/2010 | Croce et al. |
| 7,723,035 B2 | 5/2010 | Croce et al. |
| 7,728,189 B2 | 6/2010 | Croce |
| 7,749,715 B2 | 7/2010 | Russo et al. |
| 7,777,005 B2 | 8/2010 | Croce et al. |
| 7,888,010 B2 | 2/2011 | Brown et al. |
| 7,919,245 B2 | 4/2011 | Brown et al. |
| 2001/0026796 A1 | 10/2001 | Croce et al. |
| 2002/0086331 A1 | 7/2002 | Croce et al. |
| 2002/0116726 A1 | 8/2002 | Croce et al. |
| 2002/0132290 A1 | 9/2002 | Frazer |
| 2004/0033502 A1 | 2/2004 | Williams et al. |

(Continued)

FOREIGN PATENT DOCUMENTS

| CA | 2533701 A1 | 2/2005 |
| CA | 2587189 A1 | 12/2006 |
| FR | 2877350 A1 | 5/2006 |
| WO | 9015156 | 12/1990 |
| WO | 9100364 | 1/1991 |
| WO | 9107424 | 5/1991 |
| WO | 9312136 | 6/1993 |
| WO | 9410343 | 5/1994 |
| WO | 9424308 | 10/1994 |
| WO | 9426930 A1 | 11/1994 |

(Continued)

OTHER PUBLICATIONS

Lu et al, A single anti-microRNA antisense oligodeoxyribonucleotide (AMO) targeting multiple microRNAs offers an improved approach for microRNA interference, 2009, Nucl. Acids Res., vol. 37, No. 3, e24:1-10.*

Murrow et al, Identification of WEE1 as a potential molecular target in cancer cells by RNAi screening of the human tyrosine kinome, published online Oct. 2009, Breast Cancer Res Treat, 122: 347-357.*

Kendall et al, Analysis of Genetic Alterations and Clonal Proliferation in Children Treated for Acute Lymphocytic Leukemia, 2006, Cancer Res, 66: 8455-8461.*

(Continued)

*Primary Examiner* — Tracy Vivlemore
*Assistant Examiner* — Kate Poliakova-Georgantas
(74) *Attorney, Agent, or Firm* — MacMillan, Sobanski & Todd, LLC

(57) ABSTRACT

Methods of reducing spontaneous mutation rate of a cell in a subject in need thereof by reducing endogenous levels of miR-155 are described.

26 Claims, 22 Drawing Sheets
(3 of 22 Drawing Sheet(s) Filed in Color)

(56) References Cited

U.S. PATENT DOCUMENTS

| | | |
|---|---|---|
| 2004/0078834 A1 | 4/2004 | Croce |
| 2004/0152112 A1 | 8/2004 | Croce et al. |
| 2004/0265316 A1 | 12/2004 | Croce et al. |
| 2004/0265930 A1 | 12/2004 | Sun et al. |
| 2005/0019890 A1 | 1/2005 | Croce |
| 2005/0059005 A1 | 3/2005 | Tuschl et al. |
| 2005/0069918 A1 | 3/2005 | Claret |
| 2005/0074797 A1 | 4/2005 | Croce et al. |
| 2005/0075492 A1 | 4/2005 | Chen et al. |
| 2005/0112630 A1 | 5/2005 | Shaughnessy et al. |
| 2005/0164252 A1 | 7/2005 | Yeung |
| 2005/0176025 A1 | 8/2005 | McSwiggen et al. |
| 2005/0181385 A1 | 8/2005 | Linsley et al. |
| 2005/0186589 A1 | 8/2005 | Kowalik et al. |
| 2005/0256072 A1 | 11/2005 | Aronin et al. |
| 2005/0260639 A1 | 11/2005 | Nakamura et al. |
| 2005/0266443 A1 | 12/2005 | Croce et al. |
| 2005/0287530 A1 | 12/2005 | Croce et al. |
| 2006/0019286 A1 | 1/2006 | Horvitz et al. |
| 2006/0024780 A1 | 2/2006 | Aldaz et al. |
| 2006/0037088 A1 | 2/2006 | Li |
| 2006/0075511 A1 | 4/2006 | Croce et al. |
| 2006/0084059 A1 | 4/2006 | Yip et al. |
| 2006/0099619 A1 | 5/2006 | Remacle et al. |
| 2006/0105340 A1 | 5/2006 | Croce et al. |
| 2006/0105360 A1 | 5/2006 | Croce et al. |
| 2006/0127895 A1 | 6/2006 | Sabapathy |
| 2006/0165659 A1 | 7/2006 | Croce et al. |
| 2006/0166918 A1 | 7/2006 | Heidenreich et al. |
| 2006/0185027 A1 | 8/2006 | Bartel et al. |
| 2006/0188924 A1 | 8/2006 | Russo et al. |
| 2006/0188959 A1 | 8/2006 | Croce et al. |
| 2006/0189557 A1 | 8/2006 | Slack et al. |
| 2006/0247448 A1 | 11/2006 | Boivin et al. |
| 2006/0292616 A1 | 12/2006 | Neely et al. |
| 2007/0036765 A1 | 2/2007 | Civin et al. |
| 2007/0050146 A1 | 3/2007 | Bentwich et al. |
| 2007/0054849 A1 | 3/2007 | Nakamura et al. |
| 2007/0065840 A1 | 3/2007 | Naguibneva et al. |
| 2007/0065844 A1 | 3/2007 | Golub et al. |
| 2007/0072230 A1 | 3/2007 | Croce et al. |
| 2007/0092882 A1 | 4/2007 | Wang et al. |
| 2007/0099196 A1 | 5/2007 | Kauppinen et al. |
| 2007/0123482 A1 | 5/2007 | Stoffel et al. |
| 2007/0161004 A1 | 7/2007 | Brown et al. |
| 2007/0178105 A1 | 8/2007 | Croce et al. |
| 2007/0178502 A1 | 8/2007 | Reed |
| 2007/0212727 A1 | 9/2007 | Szalay et al. |
| 2007/0213292 A1 | 9/2007 | Stoffel et al. |
| 2007/0259352 A1 | 11/2007 | Bentwich et al. |
| 2007/0292878 A1 | 12/2007 | Raymond |
| 2008/0026951 A1 | 1/2008 | Brown et al. |
| 2008/0050744 A1 | 2/2008 | Brown et al. |
| 2008/0171667 A1 | 7/2008 | Brown et al. |
| 2008/0176766 A1 | 7/2008 | Brown et al. |
| 2008/0182245 A1 | 7/2008 | Brown et al. |
| 2008/0193943 A1 | 8/2008 | Murray |
| 2008/0254473 A1 | 10/2008 | Chen et al. |
| 2008/0256650 A1 | 10/2008 | Croce |
| 2008/0261908 A1 | 10/2008 | Croce et al. |
| 2008/0300211 A1* | 12/2008 | Baltimore et al. ............ 514/44 |
| 2008/0306006 A1 | 12/2008 | Croce et al. |
| 2008/0306017 A1 | 12/2008 | Croce et al. |
| 2008/0306018 A1 | 12/2008 | Croce et al. |
| 2009/0005336 A1 | 1/2009 | Wang |
| 2009/0023594 A1 | 1/2009 | Mouritzen et al. |
| 2009/0029932 A1 | 1/2009 | Voinnet et al. |
| 2009/0061424 A1 | 3/2009 | Chen |
| 2009/0092974 A1 | 4/2009 | Davison et al. |
| 2009/0099034 A1 | 4/2009 | Ahlquist et al. |
| 2009/0123533 A1 | 5/2009 | Croce et al. |
| 2009/0123912 A1 | 5/2009 | Raymond |
| 2009/0123933 A1 | 5/2009 | Mishra |
| 2009/0131348 A1 | 5/2009 | Labourier et al. |
| 2009/0131354 A1 | 5/2009 | Bader et al. |
| 2009/0131356 A1 | 5/2009 | Bader et al. |
| 2009/0163430 A1 | 6/2009 | Johnson et al. |
| 2009/0163434 A1 | 6/2009 | Bader et al. |
| 2009/0163435 A1 | 6/2009 | Bader et al. |
| 2009/0175827 A1 | 7/2009 | Byrom et al. |
| 2009/0176723 A1 | 7/2009 | Brown et al. |
| 2009/0192102 A1 | 7/2009 | Bader et al. |
| 2009/0192111 A1 | 7/2009 | Bader et al. |
| 2009/0192114 A1 | 7/2009 | Ovcharenko et al. |
| 2009/0209450 A1 | 8/2009 | Croce et al. |
| 2009/0222934 A1 | 9/2009 | Croce |
| 2009/0227533 A1 | 9/2009 | Bader et al. |
| 2009/0232893 A1 | 9/2009 | Bader et al. |
| 2009/0233297 A1 | 9/2009 | Mambo et al. |
| 2009/0253780 A1 | 10/2009 | Takeshita et al. |
| 2009/0263803 A1 | 10/2009 | Beaudenon et al. |
| 2009/0270484 A1 | 10/2009 | Croce et al. |
| 2009/0281167 A1 | 11/2009 | Shen et al. |
| 2009/0306194 A1 | 12/2009 | Ford et al. |
| 2010/0004322 A1 | 1/2010 | Croce |
| 2010/0048681 A1 | 2/2010 | Croce |
| 2010/0099200 A1 | 4/2010 | Nazabal et al. |
| 2010/0104662 A1 | 4/2010 | Oren et al. |
| 2010/0120898 A1 | 5/2010 | Croce et al. |
| 2010/0137410 A1 | 6/2010 | Croce |
| 2010/0144850 A1 | 6/2010 | Croce |
| 2010/0173319 A1 | 7/2010 | Croce et al. |
| 2010/0184032 A1 | 7/2010 | Georgantas et al. |
| 2010/0184830 A1 | 7/2010 | Croce et al. |
| 2010/0184842 A1 | 7/2010 | Croce |
| 2010/0192235 A1 | 7/2010 | Croce |
| 2010/0196426 A1 | 8/2010 | Skog et al. |
| 2010/0197770 A1 | 8/2010 | Wang et al. |
| 2010/0197774 A1 | 8/2010 | Croce et al. |
| 2010/0203544 A1 | 8/2010 | Croce et al. |
| 2010/0234241 A1 | 9/2010 | Croce et al. |
| 2010/0249213 A1 | 9/2010 | Croce |
| 2010/0257618 A1 | 10/2010 | Croce et al. |
| 2010/0317610 A1 | 12/2010 | Croce |

FOREIGN PATENT DOCUMENTS

| | | |
|---|---|---|
| WO | 9613514 A1 | 5/1996 |
| WO | 9635124 | 11/1996 |
| WO | 9729119 | 8/1997 |
| WO | 9809510 A1 | 3/1998 |
| WO | 0003685 A2 | 1/2000 |
| WO | 0050565 A2 | 8/2000 |
| WO | 0055169 A1 | 9/2000 |
| WO | 0076524 A1 | 12/2000 |
| WO | 0144466 A1 | 6/2001 |
| WO | 0168666 A1 | 9/2001 |
| WO | 0177343 A1 | 10/2001 |
| WO | 0187958 A2 | 11/2001 |
| WO | 02064171 A1 | 8/2002 |
| WO | 02064172 A2 | 8/2002 |
| WO | 03029459 A2 | 4/2003 |
| WO | 03078662 A1 | 9/2003 |
| WO | 03092370 A1 | 11/2003 |
| WO | 2004033659 A2 | 4/2004 |
| WO | 2004043387 A1 | 5/2004 |
| WO | 2004079013 A1 | 9/2004 |
| WO | 2004098377 | 11/2004 |
| WO | 2005013901 A3 | 2/2005 |
| WO | 2005017711 A2 | 2/2005 |
| WO | 2005020795 A2 | 3/2005 |
| WO | 2005060661 A2 | 7/2005 |
| WO | 2005078139 A2 | 8/2005 |
| WO | 2005079397 A2 | 9/2005 |
| WO | 2005080601 A2 | 9/2005 |
| WO | 2005103298 A2 | 11/2005 |
| WO | 2005118806 A2 | 12/2005 |
| WO | 2006105486 A2 | 10/2006 |
| WO | 2006108718 A1 | 10/2006 |
| WO | 2006119266 A2 | 11/2006 |
| WO | 2006133022 A2 | 12/2006 |
| WO | 2006137941 A2 | 12/2006 |
| WO | 2007016548 A2 | 2/2007 |
| WO | 2007033023 A2 | 3/2007 |

(56) References Cited

FOREIGN PATENT DOCUMENTS

| | | | |
|---|---|---|---|
| WO | 2007044413 A2 | 4/2007 |
| WO | 2007081680 A2 | 7/2007 |
| WO | 2007081720 A2 | 7/2007 |
| WO | 2007081740 A2 | 7/2007 |
| WO | 2007084486 A2 | 7/2007 |
| WO | 2007109236 A2 | 9/2007 |
| WO | 2007112097 A2 | 10/2007 |
| WO | 2007112754 A2 | 10/2007 |
| WO | 2007/127190 A2 | 11/2007 |
| WO | 2008008430 A2 | 1/2008 |
| WO | 2008/036168 A2 | 3/2008 |
| WO | 2008036776 A2 | 3/2008 |
| WO | 2008054828 A2 | 5/2008 |
| WO | 2008070082 A2 | 6/2008 |
| WO | 2008073915 A2 | 6/2008 |
| WO | 2008073920 A2 | 6/2008 |
| WO | 2008094545 A2 | 8/2008 |
| WO | 2008097277 A2 | 8/2008 |
| WO | 2008136971 A1 | 11/2008 |
| WO | 2008153987 A2 | 12/2008 |
| WO | 2008157319 A1 | 12/2008 |
| WO | 2009018303 A2 | 2/2009 |
| WO | 2009020905 A2 | 2/2009 |
| WO | 2009026487 A1 | 2/2009 |
| WO | 2009033140 A1 | 3/2009 |
| WO | 2009049129 A1 | 4/2009 |
| WO | 2009055773 A2 | 4/2009 |
| WO | 2009064590 A2 | 5/2009 |
| WO | 2009070653 A1 | 6/2009 |
| WO | 2009100029 A1 | 8/2009 |
| WO | 2009108853 A1 | 9/2009 |
| WO | 2009108856 A2 | 9/2009 |
| WO | 2009108860 A2 | 9/2009 |
| WO | 2009108866 A2 | 9/2009 |
| WO | 2009152300 A1 | 12/2009 |
| WO | 2010019694 A1 | 2/2010 |
| WO | 2010059779 A1 | 5/2010 |
| WO | 2010065156 A1 | 6/2010 |
| WO | 2010099161 A1 | 9/2010 |

OTHER PUBLICATIONS

EP Search Report, Application No. 12165636.7 dated Jun. 8, 2012.
EP Search Report, Application No. 12165638.3 dated Jun. 12, 2012.
Australian Government, Examiner's First Report, Appln. No. 2007243475, Dated Mar. 30, 2012.
Australian Office Action, Application No. 2006291165 dated Feb. 13, 2012.
Australian Office Action, Application No. 2006291165 dated Aug. 23, 2011.
Australian Office Action, Application No. 2007227423 dated Apr. 13, 2012.
Australian Office Action, Application No. 2007205257 dated Dec. 22, 2011.
Australian Office Action, Application No. 2007205234 dated Sep. 20, 2011.
Canadian Intellectual Property Office, Requisition by the Examiner, Application No. 2,635,616, Dated Feb. 21, 2011.
Canadian Office Action, Application No. 2,635,616, dated Feb. 27, 2011.
Canadian Office Action, Application No. 2,621,441, dated Feb. 1, 2011.
Canadian Office Action, Application No. 2,617,581, dated Apr. 2, 2012.
Canadian Office Action, Application No. 2,617,581, dated Feb. 1, 2011.
Chinese Office Action, Application No. 200680036598.3 dated Feb. 24, 2011.
Chinese Office Action, Application No. 200880112585.9 dated May 24, 2012.
Chinese Office Action, Application No. 200780040146.7 dated May 25, 2011.
Chinese Office Action, Application No. 20088011920639 dated May 3, 2012.
Chinese Office Action, Application No. 200780005821.2 dated Jan. 26, 2011.
Chinese Office Action, Application No. 200780033066.9 dated Jun. 26, 2012.
Chinese Office Action, Application No. 200680039776.8 dated Jun. 30, 2011.
Communication Concerning Office Action Received from Japanese Patent Office dated Jan. 30, 2012, Japanese Patent Application No. 2008-531200.
EP Search Report, Application No. 12154298.9 dated Jun. 4, 2012.
EP Search Report, Application No. 11196253.6 dated Apr. 24, 2012.
EP Search Report, Application No. 11196261.9 dated Feb. 28, 2012.
EP Search Report, Application No. 11196264-3 dated Feb. 28, 2012.
EP Search Report, Application No. 11196250.2 dated Apr. 24, 2012.
EP Search Report, Application No. 11196262.7 dated Feb. 28, 2012.
EP Search Report, Application No. 11196256.9 dated Feb. 28, 2012.
EP Search Report, Application No. 11196254.4 dated Feb. 28, 2012.
EP Search Report, Application No. 11196190.0 dated Apr. 24, 2012.
EP Search Report, Application No. 11196265.0 dated Mar. 5, 2012.
EP Search Report, Application No. 08782609.5 dated Oct. 28, 2010.
European Communication Pursuant to Article 94(3) EPC, Application No. 07717903.4, dated Apr. 25, 2012.
European Communication Pursuant to Article 94(3) EPC, Application No. 07810382.7, dated Dec. 8, 2010.
European Communication Pursuant to Article 94(3) EPC, Application No. 08767439.9, dated Mar. 15, 2011.
European Communication Pursuant to Article 94(3) EPC, Application No. 07716208.9, dated Sep. 13, 2011.
European Communication Pursuant to Article 94(3) EPC, Application No. 08799295.4, dated Nov. 18, 2011.
European Communication Pursuant to Article 94(3) EPC, Application No. 07867402.5, dated Jan. 5, 2011.
European Communication Pursuant to Article 94(3) EPC, Application No. 08768266.2, dated Apr. 18, 2011.
European Communication Pursuant to Article 94(3) EPC, Application No. 08767439.6, dated Feb. 12, 2011.
European Communication Pursuant to Article 94(3) EPC, Application No. 08841700.1, dated Jun. 1, 2012.
European Communication Pursuant to Article 94(3) EPC, Application No. 07867402.5, dated Apr. 10, 2012.
European Communication Pursuant to Article 94(3) EPC, Application No. 06800599.0 dated Nov. 25, 2011.
European Communication Pursuant to Article 94(3)EPC, Application No. 06814375.9 dated Oct. 14, 2011.
European Patent Application, EP 1795203 A2, Croce et al., Application No. 06010581.4, filed Feb. 7, 1997, published Jun. 13, 2007.
European Seach Report, Application No. 11151749.6, dated Feb. 8, 2011.
European Seach Report, Application No. 09714868.8 dated Aug. 1, 2011.
European Search Reoprt, Application No. 08841700.1, dated Jan. 4, 2011.
European Search Report, Application No. 08796821.0 dated Aug. 4, 2010.
European Search Report, Application No. 08770974.4, dated Oct. 21, 2011.
European Search Report, Application No. 06814375.9 dated Oct. 8, 2009.
European Search Report, Application No. 08767439.6 dated May 12, 2010.
European Search Report, Application No. 06800599.0 dated Oct. 19, 2009.
European Search Report, Application No. 07872618.9 dated Jul. 5, 2010.
European Search Report, Application No. 06825457.2 dated Sep. 16, 2009.
European Search Report, Application No. 08768266.2 dated Jul. 1, 2010.
European Search Report, Application No. 08713330.2, dated Jul. 22, 2011.

(56) References Cited

OTHER PUBLICATIONS

European Search Report, Application No. 07717903.4 dated Oct. 23, 2009.
European Search Report, Application No. 08841700.1 dated Jun. 2, 2010.
European Search Report, Application No. 07810382.7 dated Sep. 14, 2009.
European Search Report, Application No. 11151772-8, dated Feb. 8, 2011.
European Search Report, Application No. 11151769-4, dated Feb. 8, 2011.
European Search Report, Application No. 07867402.5 dated Mar. 16, 2010.
European Search Report, Application No. 09713926.5 dated Jul. 21, 2011.
European Search Report, Application No. 07717734.3 dated Nov. 9, 2009.
European Search Report, Application No. 11151771-0, dated Feb. 8, 2011.
European Search Report, Application No. 08798444.9-2402, PCT/US2008/073964, dated Dec. 16, 2010.
European Search Report, Application No. 07716208.9 dated Nov. 10, 2009.
European Search Report, Application No. 08799295.4-2402, PCT/US2008/075565, dated Nov. 9, 2010.
European Search Report, Application No. 07753450.1 dated Jan. 12, 2009.
European Supplementary Search Report, Application No. 09715064.3 dated May 24, 2011.
Japanese Office Action dated Feb. 24, 2012, Japanese Patent Application No. 2008-549532.
Japanese Office Action dated Feb. 22, 2012, Japanese Patent Application No. 2008-549549.
Japanese Office Action dated Jan. 4, 2012, Japanese Patent Application No. 2008-5251070.
Japanese Office Action dated Feb. 24, 2012, Japanese Patent Application No. 2008-549555.
Notice of Allowance and Fees Due in U.S. Appl. No. 12/298,221, filed Nov. 10, 2008, mailing date Nov. 30, 2009.
Notice of Allowance and Fees Due in U.S. Appl. No. 12/160,064, filed Jul. 3, 2008, mailing date Nov. 20, 2009.
Office Action issued in U.S. Appl. No. 12/160,064, filed Jul. 3, 2008, mailing date Aug. 10, 2009.
Office Action issued in U.S. Appl. No. 12/373,358, filed Feb. 11, 2009, mailing date Aug. 20, 2010.
Office Action issued in U.S. Appl. No. 12/160,061, filed Jul. 3, 2008, mailing date Apr. 24, 2009.
Office Action issued in U.S. Appl. No. 12/160,034, filed Jul. 3, 2008, mailing date Jun. 7, 2010.
Office Action issued in U.S. Appl. No. 12/293,471, filed Oct. 9, 2008, mailing date Jun. 8, 2010.
Office Action issued in U.S. Appl. No. 12/160,061, filed Jul. 3, 2008, mailing date Mar. 12, 2010.
Office Action issued in U.S. Appl. No. 12/160,061, filed Jul. 3, 2008, mailing date Oct. 30, 2009.
Office Action issued in U.S. Appl. No. 12/442,018, filed Mar. 27, 2009, mailing date Apr. 15, 2010.
Office Action issued in U.S. Appl. No. 12/083,067, filed Jun. 20, 2008, mailing date Jul. 8, 2010.
PCT International Preliminary Report on Patentability, PCT/US2009/035470 filed Feb. 27, 2009, dated Aug. 31, 2010.
PCT International Preliminary Report on Patentability, PCT/US2007/000159 filed Jan. 3, 2007, dated Jul. 8, 2008.
PCT International Preliminary Report on Patentability, PCT/US2006/035100 filed Sep. 11, 2006, dated Mar. 18, 2008.
PCT International Preliminary Report on Patentability, PCT/US2007/000103 filed Jan. 3, 2007, dated Jul. 8, 2008.
PCT International Preliminary Report on Patentability, PCT/US2010/025173 filed Feb. 24, 2010, dated Sep. 9, 2011.
PCT International Preliminary Report on Patentability, PCT/US2010/057758 filed Nov. 23, 2010, dated Jun. 7, 2012.
PCT International Preliminary Report on Patentability, PCT/US2009/065072 filed Nov. 19, 2009, dated Jun. 3, 2011.
PCT International Preliminary Report on Patentability, PCT/US2008/073964 filed Aug. 22, 2008, dated Feb. 24, 2010.
PCT International Preliminary Report on Patentability, PCT/US2008/075565 filed Sep. 8, 2008, dated Mar. 9, 2010.
PCT International Preliminary Report on Patentability, PCT/US2008/071532 filed Jul. 30, 2008, dated Feb. 2, 2010.
PCT International Preliminary Report on Patentability, PCT/US2008/066870 filed Jun. 13, 2008, dated Dec. 17, 2009.
PCT International Preliminary Report on Patentability, PCT/US2008/001157 filed Jan. 29, 2008, dated Aug. 4, 2009.
PCT International Preliminary Report on Patentability, PCT/US2008/072081 filed Aug. 4, 2008, dated Feb. 9, 2010.
PCT International Preliminary Report on Patentability, PCT/US2009/035458 filed Feb. 27, 2009, dated Aug. 31, 2010.
PCT International Preliminary Report on Patentability, PCT/US2007/023660 filed Nov. 1, 2007, dated May 5, 2009.
PCT International Preliminary Report on Patentability, PCT/US2008/005503 filed Apr. 29, 2008, dated Nov. 3, 2009.
PCT International Preliminary Report on Patentability, PCT/US2007/006824 filed Mar. 19, 2007, dated Sep. 23, 2008.
PCT International Preliminary Report on Patentability, PCT/US2007/020215 filed Sep. 17, 2007, dated Mar. 24, 2009.
PCT International Preliminary Report on Patentability, PCT/US2008/081294 filed Oct. 27, 2008, dated Apr. 27, 2010.
PCT International Preliminary Report on Patentability, PCT/US2009/038214 filed Mar. 25, 2009, dated Jun. 16, 2011.
PCT International Preliminary Report on Patentability, PCT/US2007/015892 filed Jul. 12, 2007, dated Jan. 13, 2009.
PCT International Preliminary Report on Patentability, PCT/US2006/038824 filed Oct. 4, 2006, dated Apr. 9, 2008.
PCT International Preliminary Report on Patentability, PCT/US2008/007196 filed Jun. 9, 2008, dated Dec. 11, 2009.
PCT International Preliminary Report on Patentability, PCT/US2007/000024 filed Jan. 3, 2007, dated Jul. 8, 2008.
PCT International Preliminary Report on Patentability, PCT/US2009/035482 filed Feb. 27, 2009, dated Aug. 31, 2010.
PCT International Preliminary Report on Patentability, PCT/US2007/009910 filed Apr. 24, 2007, dated Oct. 28, 2008.
PCT International Preliminary Report on Patentability, PCT/US2009/035463 filed Feb. 27, 2009, dated Aug. 31, 2010.
PCT International Preliminary Report on Patentability, PCT/US2006/029889 filed Jul. 31, 2006, dated Feb. 5, 2008.
PCT International Preliminary Report on Patentability, PCT/US2008/079482 filed Oct. 10, 2008, dated Apr. 13, 2010.
PCT International Search Report and the Written Opinion, PCT/US2008/71532 filed Jul. 30, 2008, dated Apr. 17, 2009.
PCT International Search Report and the Written Opinion, PCT/US2008/84821 filed Nov. 26, 2008, dated Feb. 17, 2009.
PCT International Search Report and the Written Opinion, PCT/US2007/00024 filed Jan. 3, 2007, dated Nov. 5, 2007.
PCT International Search Report and the Written Opinion, PCT/US2007/006824 filed Mar. 19, 2007, dated Mar. 3, 2008.
PCT International Search Report and the Written Opinion, PCT/US2007/09910 filed Apr. 24, 2007, dated Feb. 13, 2008.
PCT International Search Report and the Written Opinion, PCT/US2008/72081 filed Aug. 4, 2008, dated Jan. 14, 2009.
PCT International Search Report and the Written Opinion, PCT/US2007/15892 filed Jul. 12, 2007, dated Sep. 30, 2008.
PCT International Search Report and the Written Opinion, PCT/US2008/66870 filed Jun. 13, 2008, dated Nov. 10, 2008.
PCT International Search Report and the Written Opinion, PCT/US2009/38214 filed Mar. 25, 2009, dated Aug. 14, 2009.
PCT International Search Report and the Written Opinion, PCT/US2007/20215 filed Sep. 17, 2007, dated Jul. 25, 2008.
PCT International Search Report and the Written Opinion, PCT/US2008/07196 filed Jun. 9, 2008, dated Nov. 19, 2008.
PCT International Search Report and the Written Opinion, PCT/US2008/01157 filed Jan. 29, 2008, dated Aug. 7, 2008.

(56) References Cited

OTHER PUBLICATIONS

PCT International Search Report and the Written Opinion, PCT/US2006/38824 filed Oct. 4, 2006, dated Aug. 9, 2007.
PCT International Search Report and the Written Opinion, PCT/US2008/05503 filed Apr. 29, 2008, dated Sep. 25, 2008.
PCT International Search Report and the Written Opinion, PCT/US2008/73964 filed Aug. 22, 2008, dated Dec. 24, 2008.
PCT International Search Report and the Written Opinion, PCT/US2007/23660 filed Nov. 1, 2007, dated Sep. 16, 2008.
PCT International Search Report and the Written Opinion, PCT/US2009/35463 filed Feb. 27, 2009, dated Aug. 13, 2009.
PCT International Search Report and the Written Opinion, PCT/US2008/81294 filed Oct. 27, 2008, dated Mar. 26, 2009.
PCT International Search Report and the Written Opinion, PCT/US2009/35482 filed Feb. 27, 2009, dated Jul. 17, 2009.
PCT International Search Report and the Written Opinion, PCT/US2009/53586 filed Aug. 12, 2009, dated Oct. 28, 2009.
PCT International Search Report and the Written Opinion, PCT/US2008/79482 filed Oct. 10, 2008, dated Dec. 22, 2008.
PCT International Search Report and the Written Opinion, PCT/US2008/75565 filed Sep. 8, 2008, dated Dec. 9, 2008.
PCT International Search Report and the Written Opinion, PCT/US2009/35458 filed Feb. 27, 2009, dated Jul. 28, 2009.
PCT International Search Report and the Written Opinion, PCT/US2007/00159 filed Jan. 3, 2007, dated Apr. 11, 2008.
PCT International Search Report and the Written Opinion, PCT/US2010/025173 filed Feb. 24, 2010, dated Jul. 6, 2010.
PCT International Search Report and the Written Opinion, PCT/US2012/020911 filed Jan. 11, 2012, dated Apr. 25, 2012.
PCT International Search Report and the Written Opinion, PCT/US2009/65072 filed Nov. 19, 2009, dated Mar. 3, 2010.
PCT International Search Report and the Written Opinion, PCT/US2007/006824 filed Mar. 19, 2007, dated May 14, 2008.
PCT International Search Report and the Written Opinion, PCT/US2009/35470 filed Feb. 27, 2009, dated Jun. 16, 2009.
PCT International Search Report and the Written Opinion, PCT/US2006/35100 filed Sep. 11, 2006, dated Sep. 5, 2007.
PCT International Search Report and the Written Opinion, PCT/US2006/29889 filed Jul. 31, 2006, dated Jul. 10, 2007.
PCT International Search Report and the Written Opinion, PCT/US2007/00103 filed Jan. 3, 2007, dated Dec. 3, 2007.
PCT International Search Report and the Written Opinion, PCT/US2009/46999 filed Jun. 11, 2009, dated Nov. 23, 2009.
PCT Invitation to Pay Additional Fees, PCT/US2012/028016 filed Mar. 7, 2012, dated May 29, 2012.
Aiba, M. "Pathology of the Breast Carcinoma from the Viewpoint of the Proliferative Activity and Grade of Malignancy," JP J Cancer Clin, 2000, pp. 475-181, vol. 46, No. 5.
Akahoshi, M. et al., "Myeloproliferative Disorders Terminating in Acute Megakaryoblastic Leukemia with Chromosome 3q26 Abnormality," Cancer, 1987, pp. 2654-2661, vol. 60.
Akao, Y. et al., "let-7 MicroRNA Functions as a Potential Growth Suppressor in Human Colon Cancer Cells," Biol. Pharm. Bull., May 2006, pp. 903-906, vol. 29, No. 5.
Alvarez-Secord, A. et al., "Maspin Expression in Epithelial Ovarian Cancer and Associations with Poor Prognosis: A Gynecologic Oncology Group Study," Gynecologic Oncology, 2006, pp. 390-397, vol. 101.
Ambros, V. et al., "A Uniform System for MicroRNA Annotation," RNA, 2003, pp. 277-279, vol. 9.
Ambs, S. et al., "Genomic Profiling of MicroRNA and Messenger RNA Reveals Deregulated MicroRNA Expression in Prostate Cancer," Cancer Research, Aug. 2008, pp. 6162-6170, vol. 68, No. 15.
Aqeilan, R. I. et al., "Targeted Deletion of WWOX Reveals a Tumor Suppressor Function," PNAS, Mar. 2007, pp. 3949-3954, vol. 104, No. 10.
Baira, E. et al., "Ultraconserved Elements: Genomics, Function and Disease," RNA Biology, Jul. 2008, pp. 132-134, vol. 5, No. 3.

Bandres, E. et al., "Identification by Real-Time PCR of 13 Mature MicroRNAs Differentially Expressed in Colorectal Cancer and Non-Tumoral Tissues," Molecular Cancer, Jul. 2006, 10 pages, vol. 5, No. 29.
Bartel, D. P., "MicroRNAs: Target Recognition and Regulatory Functions," Cell, Jan. 2009, pp. 215-233, vol. 136.
Bednarek, A. K. et al., "WWOX, the FRA16D Gene, Behaves as a Suppressor of Tumor Growth," Cancer Research, Nov. 2001, pp. 8068-8073, vol. 61.
Bejenaro, et al., "Ultraconserved Elements in the Human Genome," Electronic Suppl. Data, Science, 2004.
Bejerano, G. et al., "Ultraconserved Elements in the Human Genome," Science, May 2004, pp. 1321-1325, vol. 304.
Bell, D. A., "Origins and Molecular Pathology of Ovarian Cancer," Modern Pathology, 2005, pp. S19-S32, vol. 18.
Bichi, R. et al., "Human Chronic Lymphocytic Leukemia Modeled in Mouse by Targeted TCL1 Expression," PNAS, May 2002, pp. 6955-6960, vol. 99, No. 10.
Bloomston, M. et al., "MicroRNA Expression Patterns to Differentiate Pancreatic Adenocarcinoma from Normal Pancreas and Chronic Pancreatitis," JAMA, May 2007, pp. 1901-1908 vol. 297, No. 1.
Blum, W. et al., "Clinical Response and miR-29b Predictive Significance in Older AML Patients Treated With a 10-Day Schedule of Decitabine," PNAS, Apr. 2010, pp. 7473-7478, vol. 107, No. 16.
Boland, C.R. et al., "Lynch Syndrome: Form, Function, Proteins, and Basketball," Gastroenterology, Aug. 2005, pp. 751-755, vol. 129, No. 2.
Braun et al., "p53-Responsive MicroRNAs 192 and 215 are Capable of Inducing Cell Cycle Arrest," Cancer Research, 2008, pp. 10094-10104, vol. 68.
Brueckner, B. et al., "The Human let-7a-3 Locus Contains an Epigenetically Regulated MicroRNA Gene with Oncogenic Function," Cancer Research, Feb. 2007, pp. 1419-1423, vol. 67, No. 4.
Budhu, A. et al., "A Unique Metastasis-Related MicroRNA Expression Signature is a Prognostic Indicator of Survival and Recurrence in Hepatocellular Carcinoma," Hepatology, 2007, p. 791A, vol. 46, No. 4, Suppl. 1, Abstract #1249.
Budhu, A. et al., "Identification of Metastasis-Related MicroRNAs in Hepatocellular Carcinoma," Hepatology, Mar. 2008, pp. 897-907, vol. 47, No. 3.
Caldas, C. et al., "Sizing Up miRNAs as Cancer Genes," Nature Medicine, Jul. 2005, pp. 712-714, vol. 11, No. 7.
Calin, G. A. et al., "Human MicroRNA Genes are Frequently Located at Fragile Sites and Genomic Regions Involved in Cancers," PNAS, Mar. 2004, pp. 2999-3004, vol. 101, No. 9.
Calin, G. A. et al., "MiR-15a and MiR-16-1 Cluster Functions in Human Leukemia," PNAS, Apr. 2008, pp. 5166-5171, vol. 105, No. 13.
Calin, G. A. et al., "MicroRNA Profiling Reveals Distinct Signatures in B Cell Chronic Lymphocytic Leukemias," PNAS, Aug. 2004, pp. 11755-11760, vol. 101, No. 32.
Calin, G. A. et al., "A MicroRNA Signature Associated with Prognosis and Progression in Chronic Lymphocytic Leukemia," The New England Journal of Medicine, Oct. 2005, pp. 1793-1801, vol. 353, No. 17.
Calin, G. A. et al., "Frequent Deletions and Down-Regulation of MicroRNA Genes miR15 and miR16 at 13q14 in Chronic Lymphocytic Leukemia," PNAS, Nov. 2002, pp. 15524-15529, vol. 99, No. 24.
Calin, G. A. et al., "Ultraconserved Regions Encoding ncRNAs are Altered in Human Leukemias and Carcinomas," Cancer Cell, Sep. 2007, pp. 215-229, vol. 12.
Calin, G. A. et al., "Chromosomal Rearrangements and MicroRNAs: A New Cancer Link with Clinical Implications," The Journal of Clinical Investigation, Aug. 2007, pp. 2059-2066, vol. 117, No. 8.
Calin, G. A. et al., "MicroRNA Signatures in Human Cancers," Nature Reviews Cancer, Nov. 2006, pp. 857-866, vol. 6.
Cannistra, S.A., "Cancer of the Ovary," The New England Journal of Medicine, 2004, pp. 2519-2529, vol. 351, No. 25.
Castoldi, M. et al., "A Sensitive Array for MicroRNA Expression Profiling (miChip) Based on Locked Nucleic Acids (LNA)," RNA, 2006, pp. 913-920, vol. 12.

(56) References Cited

OTHER PUBLICATIONS

Chan, J. A. et al., "MicroRNA-21 is an Antiapoptotic Factor in Human Glioblastoma Cells," Cancer Research, Jul. 2005, pp. 6029-6033, vol. 65, No. 14.
Chang, N.-S. et al., "Molecular Mechanisms Underlying WOX1 Activation During Apoptotic and Stress Responses," Biochemical Pharmacology, 2003, pp. 1347-1354, vol. 66.
Chang, T.-C. et al., "Widespread MicroRNA Repression by Myc Contributes to Tumorigenesis," Nat Genet., Jan. 2008, pp. 43-50, vol. 40, No. 1.
Chen, C.-Z. et al., "MicroRNAs as Regulators of Mammalian Hematopoiesis," Seminars in Immunology, 2005, pp. 155-165, vol. 17.
Cheng, A. M. et al., "Antisense Inhibition of Human miRNAs and Indications for an Involvement of miRNA in Cell Growth and Apoptosis," Nucleic Acids Research, 2005, pp. 1290-1297, vol. 33, No. 4.
Chim, S.S.C. et al., "Detection and Characterization of Placental MicroRNAs in Maternal Plasma," Clinical Chemistry, 2008, pp. 482-490, vol. 54, No. 3.
Ciafre, S. A. et al., "Extensive Modulation of a Set of MicroRNAs in Primary Glioblastoma," Biochemical and Biophysical Research Communications, 2005, pp. 1351-1358, vol. 334.
Cimmino, A. et al., Corrections to "miR-15 and miR-16 Induce Apoptosis by Targeting BCL2," PNAS, Feb. 2006, pp. 2464-2465, vol. 103, No. 7.
Cimmino, A. et al., "miR-15 and miR-16 Induce Apoptosis by Targeting BCL2," PNAS, Sep. 2005, pp. 13944-13949, vol. 102, No. 39.
Costinean, S. et al., "Pre-B Cell Proliferation and Lymphoblastic Leukemia/ High-Grade Lymphoma in Eμ-miR155 Transgenic Mice," PNAS, May 2006, pp. 7024-7029, vol. 103, No. 18.
Croce, C. M. et al., "Role of FHIT in Human Cancer," Journal of Clinical Oncology, May 1999, pp. 1618-1624, vol. 17, No. 5.
Croce, C. M. et al., "miRNAs, Cancer, and Stem Cell Division," Cell, 2005, pp. 6-7, vol. 36.
Croce, C. M., "Causes and Consequences of MicroRNA Dysregulation in Cancer," Nature Reviews Genetics, Oct. 2009, pp. 704-714, vol. 10.
Croce, C. M., "Oncogenes and Cancer," The New England Journal of Medicine, Jan. 2008, pp. 502-511, vol. 358, No. 5.
Cui, S. et al., "MicroRNAs that Underlie Ovarian Cancer Development and Response to Chemotherapy," 98th AACR Annual Meeting, Apr. 14-18, 2007, Los Angeles, CA.
Dalmay, T. et al., "MicroRNAs and the Hallmarks of Cancer," Oncogene, 2006, pp. 6170-6175, vol. 25.
Davies, B.R. et al., "AZD6244 (ARRY-142886), a Potent Inhibitor of Mitogen-Activated Protein Kinase/Extracellular Signal-Regulated Kinase Kinase 1/2 Kinases: Mechanism of Action in vivo, Pharmacokinetic/Pharmacodynamic Relationship, and Potential for Combination in Preclinical Needs," Mol. Cancer Ther., Aug. 2007, vol. 6, No. 8, pp. 2209-2219.
Davies, F. E. et al., "Insights into the Multistep Transformation of MGUS to Myeloma Using Microarray Expression Analysis," Blood, Dec. 2003, pp. 4504-4511, vol. 102, No. 13.
Debernardi, S. et al., "MicroRNA miR-181a Correlates with Morphological Sub-Class of Acute Myeloid Leukemia and the Expression of its Target Genes in Global Genome-Wide Analysis," Leukemia, 2007, pp. 912-916, vol. 21.
Dohner, H. et al., "Genomic Aberrations and Survival in Chronic Lymphocytic Leukemia," The New England Journal of Medicine, Dec. 2000, pp. 1910-1916, vol. 343, No. 26.
Druck, et al., "FHIT," Atlas of Genetics and Cytogenetics in Oncology and Haematology, 2007, pp. 171-178, vol. 2.
Eiriksdottir, G. et al., "Mapping Loss of Heterozygosity at Chromosome 13q: Loss at 13q12-q13 is Associated wit Breast Tumour Progression and Poor Prognosis," European Journal of Cancer, 1998, pp. 2076-2081, vol. 34, No. 13.
Eis, P. S. et al., "Accumulation of miR-155 and BIC RNA in Human B Cell Lymphomas," PNAS, Mar. 2005, pp. 3627-3632, vol. 102, No. 10.
Esquela-Kerscher, A. et al., "Oncomirs—MicroRNAs with a Role in Cancer," Nature Reviews:Cancer, Apr. 2006, pp. 259-269, vol. 6.
Fabbri, M. et al., "MicroRNAs," The Cancer Journal, Jan./Feb. 2008, pp. 1-6, vol. 14, No. 1.
Fabbri, M. et al., "MicroRNA-29 Family Reverts Aberrant Methylation in Lung Cancer by Targeting DNA Methyltransferases 3A and 3B," PNAs, Oct. 2007, pp. 15805-15810, vol. 104, No. 40.
Fabbri, M. et al., "WWOX Gene Restoration Prevents Lung Cancer Growth In Vitro and In Vivo," PNAS, Oct. 2005, pp. 15611-15616, vol. 102, No. 43.
Felli, N. et al., "MicroRNAs 221 and 222 Inhibit Normal Erythropoiesis and Erythroleukemic Cell Growth via Kit Receptor Down-Modulation," PNAS, Dec. 2005, pp. 18081-18086, vol. 102, No. 50.
Feng, G. et al., "Elevated Serum-Circulating RNA in Patients with Conventional Renal Cell Cancer," Anticancer Research, 2008, pp. 321-326, vol. 28.
Flavin, RJ et al., "MicroRNA Gene Expression Profiling in Human Ovarian and Primary Peritoneal Serous Carcinomas" USCAP 96th Annual Meeting, Abstract #897, San Diego, CA, Mar. 2007.
Fong, Y. et al., "Muir-Torre-Like Syndrome in FHIT-Deficient Mice," PNAS, Apr. 2000, pp. 4742-4747, vol. 97, No. 9.
Ford, L.P., "A MicroRNA Expression Signature of Human Solid Tumors Defines Cancer Gene Targets," Leukemia Research, 2006, pp. 511-513, vol. 30.
Fox, T. et al., "A Single Amino Acid Substitution Makes ERK2 Susceptible to Pyridinyl Imidazole Inhibitors of p38 MAP Kinase," Protein Science, 1998, pp. 2249-2255, vol. 7.
Fujuta, S. et al., "miR-21 Gene Expression Triggered by AP-1 is Sustained Through a Double-Negative Feedback Mechanism," J. Mol. Biol., Abstract, 2008, pp. 492-504, vol. 378.
Gailiun, M., "Single MicroRNA Causes Cancer in Transgenic Mice," Research Communications, The Ohio State University, Apr. 2006.
Gang, M. et al., "Expression of Programmed Cell Death 4 and Its Clinicopathological Significance in Human Pancreatic Cancer," Abstract, 2005, pp. 597-600, vol. 27.
Garofalo, M. et al., "MicroRNA Signatures of TRAIL Resistance in Human Non-Small Cell Lung Cancer," Oncogene, 2007, pp. 3854-3855, vol. 27.
Garofalo, M. et al., "miR-221&222 Regulate TRAIL Resistance and Enhance Tumorigenicity through PTEN and TIMP3 Downregulation," Cancer Cell, Dec. 2009, pp. 498-509, vol. 16.
Garzon, et al., "MicroRNA 29b Functions in Acute Myeloid Leukemia," Prepublished Online, www.bloodjournal.org, Oct. 2009, doi:10.1182/blood-2009-03-211938, pp. 5331-5341, vol. 114.
Garzon, R. et al., "MicroRNA Expression and Function in Cancer," TRENDS in Molecular Medicine, Oct. 2006, pp. 580-587, vol. 12, No. 12.
Garzon, R. et al., "MicroRNA Signatures Associated with Cytogenetics and Outcome in Acute Myeloid Leukemia," ASH Annual Meeting Abstracts, Nov. 2006, Abstract #151, Part 1, p. 498, vol. 108, Issue 11.
Garzon, R. et al., "MicroRNA Signatures Associated with Cytogenetics and Prognosis in Acute Myeloid Leukemia," Blood, Published Online Jan. 2008, DOI: 10.1182/blood-2007-07-098749.
Garzon, R. et al., "MicroRNA Fingerprints During Human Megakaryocytopoiesis," PNAS, Mar. 2006, pp. 5078-5083, vol. 103, No. 13.
Godlewski, J. et al., "Targeting of the Bmi-1 Oncogene/Stem Cell Renewal Factor by MicroRNA-128 Inhibits Glioma Proliferation and Self-Renewal," Cancer Research, Nov. 2008, pp. 9125-9130, vol. 68, No. 22.
Gourley, C. et al., "WWOX Gene Expression Abolishes Ovarian Cancer Tumorigenicity in Vivo and Decreases Attachment to Fibronectin via Integrin α3," Cancer Research, Jun. 2009, pp. 4835-4842, vol. 69, No. 11.
Griffiths-Jones, S. et al., "miRBase: MicroRNA Sequences, Targets and Gene Nomenclature," Nucleic Acids Research, 2006, pp. D140-D144, vol. 34.
Griffths-Jones, S. et al., "miRBase: Tools for MicroRNA Genomics," Nucleic Acids Research, 2008, pp. D154-D157, vol. 36.
Griffths-Jones, S., "The MicroRNA Registry," Nucleic Acids Research, 2004, pp. D109-D111, vol. 32.

(56) References Cited

OTHER PUBLICATIONS

Guimaraes-Sternberg, C. et al., "MicroRNA Modulation of Megakaryoblast Fate Involves Cholinergic Signaling," Leukemia Research, 2006, pp. 583-595, vol. 30.
Guweidhi, A. et al. "Enhanced Expression of 14-3-3sigma in Pancreatic Cancer and its Role in Cell Cycle Regulation and Apoptosis," Carcinogenesis, 2004, pp. 1575-1585, vol. 25, No. 9.
Havelange, V. et al., "MicroRNAs: New Players in Acute Myeloid Leukemia," British Journal of Cancer, 2009, pp. 743-748, vol. 101.
Hayashita, Y. et al., "A Polycistronic MicroRNA Cluster, miR-17-92, is Overexpressed in Human Lung Cancers and Enhances Cell Proliferation," Cancer Research, Nov. 2005, pp. 9628-9632, vol. 65, No. 21.
He, L. et al., "A MicroRNA Polycistron as a Potential Human Oncogene," Nature, Jun. 2005, pp. 828-833, vol. 435.
He, X. et al., "MicroRNA and Esophageal Carcinoma," Journal of Nanjing Medical University, 2007, pp. 201-206, vol. 21, No. 4.
Herling, et al., "TCL1 Shows a Regulated Expression Pattern in Chronic Lymphocytic Leukemia that Correlates with Molecular Subtypes and Proliferative State," Leukemia, Feb. 2006, pp. 280-285, vol. 20, No. 2.
Hiromura, M. et al., "Identification of Nerve Growth Factor-Responsive Element of the TCL1 Promoter as a Novel Negative Regulatory Element," The Journal of Biological Chemistry, Sep. 2006, pp. 27753-27764, vol. 281, No. 38.
Huang, Y.-S. et al., "Microarray Analysis of MicroRNA Expression in Hepatocellular Carcinoma and Non-Tumorous Tissues Without Viral Hepatitis," Journal of Gastroenterology and Hepatology, 2008, pp. 87-94, vol. 23.
Iliopoulos, D. et al., "Inhibition of Breast Cancer Growth InVitro and In Vivo: Effect of Restoration of WWOX Expression," Clin. Cancer Research, Jan. 2007, pp. 268-274, vol. 13, No. 1.
Iliopoulos, D. et al., "Fragile Genes as Biomarkers: Epigenetic Control of WWOX and FHIT in Lung, Breast and Bladder Cancer," Oncogene, 2005, pp. 1625-1633, vol. 24.
Iorio, M. V. et al., "MicroRNA Signatures in Human Ovarian Cancer," Cancer Research, Sep. 2007, pp. 8699-8707, vol. 67, No. 18.
Iorio, M. V. et al., "MicroRNA Gene Expression Deregulation in Human Breast Cancer," Cancer Research, Aug. 2005, pp. 7065-7070, vol. 65, No. 16.
Ishii, H. et al., "Effect of Adenoviral Transduction of the Fragile Histidine Triad Gene into Esophageal Cancer Cells," Cancer Research, Feb. 2001, pp. 1578-1584, vol. 61.
Ivanovska, I. et al., "MicroRNAs in the miR-106b Family Regulate p21/CDKN1A and Promote Cell Cycle Progression," Molecular and Cellular Biology, Apr. 2008, pp. 2167-2174, vol. 28, No. 7.
Jacobs, I.J. et al., "Prevalence Screening for Ovarian Cancer in Postmenopausal Women by CA 125 Measurement and Ultrasonography," BMJ, Apr. 1993, pp. 1030-1034, vol. 306.
Jacobs, I.J. et al., "Progress and Challenges in Screening for Early Detection of Ovarian Cancer," Molecular & Cellular Proteomics, 2004, pp. 355-366, vol. 3.
Jansen, A. P. et al., "Epidermal Expression of the Translation Inhibitor Programmed Cell Death 4 Suppresses Tumorigenesis," Cancer Research, Jul. 2005, pp. 6034-6041, vol. 65, No. 14.
Jazbutyte, V. et al., "MicroNRA-21: From Cancer to Cardiovascular Disease," Current Drug Targets, Abstract, 2010, pp. 926-935, vol. 11.
Jemal, A. et al., "Cancer Statistics, 2008," CA Cancer J. Clin., 2008, pp. 71-96, vol. 58, No. 2.
Ji, J. et al., "MicroRNA Expression, Survival, and Response to Interferon in Liver Cancer," The New England Journal of Medicine, Oct. 2009, pp. 1437-1447, vol. 361, No. 15.
Ji, J. et al., "New Kids on the Block: Diagnostic and Prognostic MicroRNAs in Hepatocellular Carcinoma," Cancer Biology & Therapy, Aug. 2009, pp. 1-8, vol. 8, No. 16.
Ji, L. et al., "Induction of Apoptosis and Inhibition of Tumorigenicity and Tumor Growth by Adenovirus Vector-Mediated Fragile Histidine Triad (FHIT) Gene Overexpression," Cancer Research, Jul. 1999, pp. 3333-3339, vol. 59.

Jiang, J. et al., "Association of MicroRNA Expression in Hepatocellular Carcinomas with Hepatitis Infection, Cirrhosis, and Patient Survival," Clin Cancer Research, Jan. 2008, pp. 419-427, vol. 14, No. 2.
Jiang, J. et al., "Real-Time Expression Profiling of MicroRNA Precursors in Human Cancer Cell Lines," Nucleic Acids Research, 2005, pp. 5394-5403, vol. 33, No. 17.
John, B. et al., "Human MicroRNA Targets," PLOS Biology, Nov. 2004, pp. 1862-1879, vol. 2, Issue 11.
Johnson, S. M. et al., "RAS is Regulated by the let-7 MicroRNA Family," Cell, Mar. 2005, pp. 635-647, vol. 120.
Johnson, S. M. et al., "RAS is Regulated by the let-7 MicroRNA Family," Supplemental Data, Cell, Mar. 2005, pp. 635-647, vol. 120.
Kawasaki, H. et al., "MicroRNA-196 Inhibits HOXB8 Expression in Myeloid Differentiation of HL60 Cells," Nucleic Acids Symposium Series, 2004, pp. 211-212, No. 48.
Kelly, L.M. et al., "CT53518, A Novel Selective FLT3 Antagonist for the Treatment of Acute Myelogenous Leukemia (AML)," Cancer Cell, Jun. 2002,pp. 421-432, vol. 1.
Kim, H. et al., "Elevated mRNA Levels of DNA Methyltransferase-1 as an Independent Prognostic Factor in Primary Nonsmall Cell Lung Cancer," Cancer, Sep. 2006, pp. 1042-1049, vol. 107, No. 5.
Kotoula, V. et al., "In Situ Detection of MicroRNAs 146b, 221 and 222 in Human Carcinoma Tissues Reveals Tumor-Type Specific Expression Patterns," In: Proceedings of the 98th Annual Meeting of the American Association for Cancer Research, Apr. 14-18, 2007 Los Angeles, CA: AACR, 2007, 2 pages, Abstract No. 1780.
Koturbash, I. et al., "Role of Epigenetic Effectors in Maintenance of the Long-Term Persistent Bystander Effect in Spleen In Vivo," Carcinogenesis, 2007, pp. 1831-1838, vol. 28, No. 8.
Kozomara, A. et al., "miRBase: Integrating MicroRNA Annotation and Deep-Sequencing Data," Nucleic Acids Research, 2011, pp. D152-D157, vol. 39.
Krek, A. et al., "Combinatorial MicroRNA Target Predictions," Nature Genetics, May 2005, pp. 495-500, vol. 37, No. 5.
Kulshreshtha, R. et al., "A MicroRNA Signature of Hypoxia," Molecular and Cellular Biology, Mar. 2007, pp. 1859-1867, vol. 27, No. 5.
Kuroki, et al., "Genetic Alterations of the Tumor Suppressor Gene WWOX in Esophageal Squamous Cell Carcinoma," Cancer Research, Apr. 2002, pp. 2258-2260, vol. 62.
Kutay, H. et al., "Downregulation of miR-122 in the Rodent and Human Hepatocellular Carcinomas," Journal of Cellular Biochemistry, 2006, pp. 671-678, vol. 99.
Lagos-Quintana, M. et al., "Identification of Tissue-Specific MicroRNAs from Mouse," Current Biology, Apr. 2002, pp. 735-739, vol. 12.
Lagos-Quintana, M. et al., "New MicroRNAs From Mouse to Human," RNA, 2003, pp. 175-179, vol. 9, No. 2.
Landgraf, P. et al., "A Mammalian MicroRNA Expression Atlas Based on Small RNA Library Sequencing," Cell, Jun. 2007, pp. 1401-1414, vol. 129.
Landi, M. T. et al., "Gene Expression Signature of Cigarette Smoking and Its Role in Lung Adenocarcinoma Development and Survival," PLOS One, Feb. 2008, pp. 1-8, vol. 3, Issue 2.
Lanza, G. et al., "mRNA/microRNA Gene Expression Profile in Microsatellite Unstable Colorectal Cancer," Molecular Cancer, 2007, pp. 1-11, vol. 6, No. 54.
Lawrie, C.H. et al., "Detection of Elevated Levels of Tumour-Associated MicroRNAs in Serum of Patients with Diffuse Large B-Cell Lymphoma," British Journal of Haematology, 2008, pp. 672-675, vol. 141.
Lee, E. J. et al., "Expression Profiling Identifies MicroRNA Signature in Pancreatic Cancer," Int. J. Cancer, 2006, pp. 1046-1054, vol. 120.
Lewis, B. P. et al., "Prediction of Mammalian MicroRNA Targets," Cell, Dec. 2003, pp. 787-798, vol. 115.
Li, S.-C. et al., "Bioinformatic Discovery of MicroRNA Precursors from Human ESTs and Introns," BMC Genomics, 2006, vol. 7.
Li, Z. et al., "Inhibition of PRL-3 Gene Expression in Gastric Cancer Cell Line SGC7901 via MicroRNA Suppressed Reduces Peritoneal Metastasis," Biochemical and Biophysical Research, Sep. 2006, pp. 229-237, vol. 348, No. 1.

(56) References Cited

OTHER PUBLICATIONS

Lin, R.-K. et al., "Alteration of DNA Methyltransferases Contributes to 5'CpG Methylation and Poor Prognosis in Lung Cancer," Lung Cancer, 2007, pp. 205-213, vol. 55.
Lipp, E., "MicroRNAs Inform Cancer Research: Alterations in the Expression of miRNA Genes Contribute to Pathogenesis on Broad Basis," Genetic Engineering & Biotechnology News, Dec. 2009, pp. 38-39, genengnews.com.
Liu, C.-G. et al., "An Oligonucleotide Microchip for Genome-Wide MicroRNA Profiling in Human and Mouse Tissues," PNAS, Jun. 2004, pp. 9740-9744, vol. 101, No. 26.
Lu, J. et al., "MicroRNA Expression Profiles Classify Human Cancers," Nature, Jun. 2005, pp. 834-838, vol. 435.
Lu, J. et al., "MicroRNA Expression Profiles Classify Human Cancers," Nature, Jun. 2005, pp. 834-838, vol. 435, Supplementary Information.
Lujambio, A. et al., "A MicroRNA DNA Methylation Signature for Human Cancer Metastasis," PNAS, Sep. 2008, pp. 13556-13561, vol. 105, No. 36.
Ma, G. et al., "Expression of Programmed Cell Death 4 and Its Clinicopathological Significance in Human Pancreatic Cancer," Department of General Surgery, the First Affiliated Hospital, China Medical University, Oct. 2005, pp. 597-600.
Mack, G. S., "MicroRNA Gets Down to Business," Nature Biotechnology, Jun. 2007, pp. 631-638, vol. 25, No. 6.
Marchetti, A. et al., "EGFR Mutations in Non-Small-Cell Lung Cancer: Analysis of a Large Series of Cases and Development of a Rapid and Sensitive Method for Diagnostic Screening with Potential Implications on Pharmacologic Treatment," Journal of Clinical Oncology, Feb. 2005, pp. 857-865, vol. 23, No. 4.
Marcucci, et al., "MicroRNA Expression in Cytogenetically Normal Acute Myeloid Leukemia," NEJM, May 2008, pp. 1919-1928, vol. 358, No. 18.
Mattie, M. D. et al., "Optimized High-Throughput MicroRNA Expression Profiling Provides Novel Biomarker Assessment of Clinical Prostate and Breast Cancer Biopsies," Molecular Cancer, Jun. 2006, 14 pages, vol. 5, No. 24.
Mazurek, N. et al., "Phosphorylated Galectin-3 Mediates Tumor Necrosis Factor-Related Apoptosis-Inducing Ligand Signaling by Regulating Phosphatase and Tensin Homologue Deleted on Chromosome 10 in Human Breast Carcinoma Cells," The Journal of Biological Chemistry, Jul. 2007, pp. 21337-21348, vol. 282, No. 29.
McManus, M. T., "MicroRNAs and Cancer," Seminars in Cancer Biology, 2003, pp. 253-258, vol. 13.
Medina, P.P. et al., "OncomiR Addiction in an In Vivo Model of MicroRNA-21-Induced Pre-B-Cell Lymphoma," Nature Letters, Sep. 2010, pp. 86-91, vol. 467.
Medina, P.P., "OncomiR Addicton in an in vivo Model of MicroRNA-21-Induced Pre-B-Cell Lymphoma," Supplementary Information, Sep. 2010, p. 1-22.
Megraw, M. et al., "miRGen: A Database for the Study of Animal MicroRNA Genomic Organization and Function," Nucleic Acids Research, 2007, pp. D149-D155, vol. 35.
Mendell, J.T., "miRiad Roles for the miR-17-92 Cluster in Development and Disease," Cell, 2008, pp. 217.
Meng, F. et al., "MicroRNA-21 Regulates Expression of the PTEN Tumor Suppressor Gene in Human Hepatocellular Cancer," Gastroenterology, 2007, pp. 647-658, vol. 133.
Meng, F. et al., "Involvement of Human MicroRNA in Growth and Response to Chemotherapy in Human Cholangiocarcinoma Cell Lines," Gastroenterology, 2006, pp. 2113-2129, vol. 130.
Mi, S. et al., "MicroRNA Expression Signatures Accurately Discriminate Acute Lymphoblastic Leukemia from Acute Myeloid Leukemia," PNAS, Dec. 2007, pp. 19971-19976, vol. 104, No. 50.
Michael, M. Z. et al., "Reduced Accumulation of Specific MicroRNAs in Colorectal Neoplasia," Molecular Cancer Research, Oct. 2003, pp. 882-891, vol. 1.

Miller, M. K. et al., "Concurrent Chronic Lymphocytic Leukemia Cutis and Acute Myelogenous Leukemia Cutis in a Patient with Untreated CLL," The American Journal of Dermatopathology, 2001, pp. 334-340, vol. 23, No. 4.
Mitchell, P. S. et al., "Circulating MicroRNAs as Stable Blood-Based Markers for Cancer Detection," PNAS, Jul. 2008, pp. 10513-10518, vol. 105, No. 30.
Mitrovic, T. et al., "Cancer Gene Therapy," Arch. Oncology, 2005, pp. 23-26, vol. 13, No. 1.
Mountzios, G. et al., "Mechanisms of Disease: Signal Transduction in Lung Carcinogenesis-A Comparison of Smokers and Never-Smokers," Nature Clinical Practice Oncology, Oct. 2008, pp. 610-618, vol. 5, No. 10.
Murakami, Y. et al., "Comprehensive Analysis of MicroRNA Expression Patterns in Hepatocellular Carcinoma and Non-Tumorous Tissues," Oncogene, 2006 pp. 2537-2545, vol. 25., published online Dec. 5, 2005.
Naegeli, K. et al., "Novel Mechanisms of Ovarian Cancer Growth Inhibition, via MicroRNA Downregulation and Oxidative Damage, by a Ratioanlly Designed Histone Deacetylase Inhibitor," Abstract #2475, 98th ACCR Annual Meeting, Apr. 14-18, 2007, Los Angeles, CA.
Nakajima, G. et al., "Non-Coding MicroRNAs HAS-LET-7G and HAS-MIR-181b are Associated with Chemoresponse to S-1 in Colon Cancer," Cancer Genomics & Proteomics, Sep. 2006, pp. 317-324, vol. 3, No. 5.
Nakanishi, H. et al., "ALL1 Fusion Proteins Induce Deregulation of EphA7 and ERK Phosphorylation in Human Acute Leukemias," PNAS, Sep. 2007, pp. 14442-14447, vol. 104, No. 36.
Nam, E.J. et al., "MicroRNA Expression Profiles in Serous Ovarian Carcinoma," Clinical Cancer Research, 2008, pp. 2690-2695, vol. 14, No. 9.
Negrini, M. et al., "MicroRNAs in Human Cancer: From Research to Therapy," Journal of Cell Science, Apr. 2007, pp. 1833-1840, vol. 120.
Nicoloso, M.S. et al., "MicroRNAs—The Micro Steering Wheel of Tumour Metastases " Nature Reviews: Cancer, Apr. 2009, pp. 293-302, vol. 9.
Nurden, A.T., "Qualitative Disorders of Platelets and Megakaryocytes," Journal of Thrombosis and Haemostasis, 2005, vol. 3, pp. 1773-1782.
Okada, H. et al., "MicroRNAs in Immune Regulation—Opportunities for Cancer Immunotherapy," The International Journal of Biochemistry & Cell Biology, 2010, pp. 1256-1261, vol. 42.
Olivier, R.I. et al., "CA125 and Transvaginal Ultrasound Monitoring in High-Risk Women Cannot Prevent the Diagnosis of Advanced Ovarian Cancer," Gynecologic Oncology, 2006, pp. 20-26, vol. 100.
Palamarchuk, A. et al., "Akt Phosphorylates Tcl1 Oncoprotein and Inhibits Its Repressor Activity," Cancer Research, Jun. 2005, pp. 4515-4519, vol. 65, No. 11.
Pawelczyk, T. et al., "Expression in *Escherichia coli* and Simple Purification of Human Fhit Protein," Protein Expr. Purlf., Apr. 2000, pp. 320-326, vol. 18, No. 3.
Pedersen, I. M. et al., "Interferon Modulation of Cellular MicroRNAs as an Antiviral Mechanism," Nature, Oct. 2007, pp. 919-922, vol. 449.
Pekarsky, Y. et al., "Tcl1 Functions as a Transcriptional Regulator and is Directly Involved in the Pathogenesis of CLL," PNAS, Dec. 2008, pp. 19643-19648, vol. 105, No. 50.
Pekarsky, Y. et al., "Tcl1 Expression in Chronic Lymphocytic Leukemia is Regulated by miR-29 and miR-181," Cancer Research, Dec. 2006, pp. 11590-11593, vol. 66, No. 24.
Pekarsky, Y. et al., "Animal Models for Chronic Lymphocytic Leumekia," Journal of Cellular Biochemistry, 2007, pp. 1109-1118, vol. 100.
Pekarsky, Y. et al., "Tcl1 Enhances Akt Kinase Activity and Mediates Its Nuclear Translocation," PNAS, Mar. 2000, pp. 3028-3033, vol. 97, No. 7.
Petrocca, F. et al., "MicroRNAs Deregulation in Gastric Cancer," PNAS, Apr. 2006, p. 1338, vol. 47, Abstract # 5690.
Petrocca, F. et al., "E2F1-Regulated MicroRNAs Impair TGFβ-Dependent Cell-Cycle Arrest and Apoptosis in Gastric Cancer," Cancer Cell, Mar. 2008, pp. 272-286, vol. 13.

(56) References Cited

OTHER PUBLICATIONS

Pichiorri et al., "Downregulation of p53-Inducible MicroRNAs 192, 194 and 215 Impairs the p53/MDM2 Autoregulatory Loop in Multiple Myeloma Development," Cancer Cell, 2010, pp. 367-381, vol. 18.

Pichiorri, F. et al., "MicroRNAs Regulate Critical Genes Associated with Multiple Myeloma Pathogenesis," PNAS, Sep. 2008, pp. 12885-12890, vol. 105, No. 35.

Pineau, P. et al., "miR-221 Overexpression Contributes to Liver Tumorigenesis," PNAS, Jan. 2010, pp. 264-269, vol. 107, No. 1.

Porkka, K.P. et al., "MicroRNA Expression Profiling in Prostate Cancer," Cancer Research, 2007, pp. 6130-6135, vol. 67, No. 13.

Prueitt, R. L. et al., "Expression of MicroRNAs and Protein-Coding Genes Associated with Perineural Invasion in Prostate Cancer," The Prostate, 2008, pp. 1152-1164, vol. 68.

Pruitt, K.D. et al., "NCBI Reference Sequence (RefSeq): A Curated Non-Redundant Sequence Database of Genomes, Transcripts and Proteins," Nucleic Acids Research, 2005, pp. D501-D504, vol. 33.

Qin, H. R. et al., "A Role for the WWOX Gene in Prostate Cancer," Cancer Research, Jul. 2006, pp. 6477-6481, vol. 66, No. 13.

Ramkissoon, S. H, et al., "Hematopoietic-Specific MicroRNA Expression in Human Cells," Leukemia Research, 2006, pp. 643-647, vol. 30.

Ribas, J. et al., "The Transcriptional Regulation of miR-21, Its Multiple Transcripts, and Their Implication in Prostate Cancer," Cell Cycle, 2010, pp. 923-929, vol. 9.

Roldo, C. et al., "MicroRNA Expression Abnormalities in Pancreatic Endocrine and Acinar Tumors Are Associated With Distinctive Pathologic Feature and Clinical Behavior," Journal of Clinical Oncology, Oct. 2006, pp. 4677-4684, vol. 24, No. 29.

Rossi, S. et al., "MicroRNA Fingerprinting of CLL Patients with Chromosome 17p Deletion Identify a miR-21 Score that Stratifies Early Survival," Blood, Aug. 2010, pp. 945-952, vol. 116, No. 6.

Rozovskaia, T. et al., "Expression Profiles of Acute Lymphoblastic and Myeloblastic Leukemias with ALL-1 Rearrangements," PNAS, Jun. 2003, pp. 7853-7858, vol. 100, No. 13.

Ryu, J.K. et al., "Aberrant MicroRNA-155 Expression is an Early Event in the Multistep Progression of Pancreatic Adenocarcinoma," Pancreatology, 2010, pp. 66-73, vol. 10.

Saini, H. K. et al., "Annotation of Mammalian Primary MicroRNAs," BMC Genomics, 2008, vol. 9.

Saito, Y. et al., "Specific Activation of MicroRNA-127 with Downregulation of the Proto-Oncogene BCL6 by Chromatin-Modifying Drugs in Human Cancer Cells," Cancer Cell, Jun. 2006, pp. 435-443, vol. 9.

Santanam, U. et al., "Chronic Lymphocytic Leukemia Modeled in Mouse by Targeted miR-29 Expression," PNAS, Jul. 2010, pp. 12210-12215, vol. 107, No. 27.

Sasaki, Y.T.F. et al., "Coordinated Expression of ncRNAs and HOX mRNAs in the Human HOXA Locus," Biochemical and Biophysical Communications, 2007, pp. 724-730, vol. 357.

Schagen, F. et al., "Genetic Targeting of Adenovirus Vectors Using a Reovirus Signal-Based Attachment Protein," Molecular Therapy, May 2006, pp. 997-1005, vol. 13, No. 5.

Schetter, A. J. et al., "MicroRNA Expression Profiles Associated With Prognosis and Therapeutic Outcome in Colon Adenocarcinoma," JAMA, Jan. 2008, pp. 425-436, vol. 299, No. 4.

Schetter, A.J. et al., "Association of Inflammation-Related and MicroRNA Gene Expression with Cancer Specific Mortality of Colon Adenocarcinoma," Clin. Cancer Res., Sep. 2009, pp. 5878-5887, vol. 15, No. 18.

Schmittgen, T. D. et al., "A High-Throughput Method to Monitor the Expression of MicroRNA Precursors," Nucleic Acids Research, Feb. 2004, vol. 32, No. 4.

Seike, M. et al., "MiR-21 is an EGFR-Regulated Anti-Apoptotic Factor in Lung Cancer in Never-Smokers," PNAS, Jul. 2009, pp. 12085-12090. vol. 106, No. 29.

Seike, M. et al., "MiR-21 is an EGFR-Regulated Anti-Apoptotic Factor in Lung Cancer in Never-Smokers," Supporting Information, PNAS, Jul. 2009, pp. 12085-12090. vol. 106, No. 29.

Seike, M., "MicroRNA Expression Profiles in Lung Cancer Cooperated with Drug Sensitivity to EGFR Tyrosine Kinase Inhibitor," J. Nippon Med. School, 2009, pp. 275-276, vol. 76, No. 5.

Seth, P., "Vector-Mediated Cancer Gene Therapy," Cancer Biology & Therapy, May 2005, pp. 512-517, vol. 4, Issue 5.

Sevinsky, J. R. et al., "Extracellular Signal-Regulated Kinase Induces the Megakaryocyte GPllb/CD41 Gene Through MafB/Kreisler," Molecular and Cellular Biology, May 2004, pp. 4534-4545, vol. 24, No. 10.

Sharma, S. et al., "Development of Inhalational Agents for Oncologic Use," Journal of Clinical Oncology, Mar. 2001, Abstract, vol. 19, Issue 6.

Shen, H, et al., "A Novel Polymorphism in Human Cytosine DNA-Methyltransferase-3B Promoter is Associated with an Increased Risk of Lung Cancer," Cancer Research, Sep. 2002, pp. 4992-4995, vol. 62.

Slack, F.J., "Big Roles for Small RNAs," Nature, Feb. 2010, p. 616, vol. 463.

Stamatopoulos, B. et al., "MicroRNA-29c and MicroRNA-233 Down-Regulation has In Vivo Significance in Chronic Lymphocytic Leukemia and Improves Disease Risk Stratification," Blood, May 2009, pp. 5237-5245, vol. 113, No. 21.

Suarez-Saiz, F.J. et al., "MicroRNA Expression Profiling in Acute Myelogenous Leukemia," Canada Blood, Nov. 2004, Abstract #1131, p. 320A.

Taccioli, C. et al., "Ucbase & miRfunc: A Database of Ultraconserved Sequences and MicroRNA Function," Nucleic Acids Research, 2009, pp. D41-D48, vol. 37.

Takamizawa, J. et al., "Reduced Expression of the let-7 MicroRNAs in Human Lung Cancers in Association with Shortened Postoperative Survival," Cancer Research, Jun. 2004, pp. 3753-3756, vol. 64.

Tang, X. et al., "A Simple Array Platform for MicroRNA Analysis and Its Application in Mouse Tissues," RNA, Aug. 2007, pp. 1-20, vol. 13.

Taylor, D.D. et al., "MicroRNA Signatures of Tumor-Derived Exosomes as Diagnostic Biomarkers of Ovarian Cancer," Gynecologic Oncology, 2008, pp. 13-21, vol. 110.

Thomson, J. M. et al., "A Custom Microarray Platform for Analysis of MicroRNA Gene Expression," Nature Methods, Oct. 2004, pp. 1-7, vol. 1, No. 1.

Thomson, M., Supplementary data for "A Custon Microarray Platform for Analysis of MicroRNA Gene Expression," Nature Methods, Oct. 2004, pp. 47-53, vol. 1, No. 1.

Thorgeirsson, S. S. et al., "Functional Genomics of Hepatocellular Carcinoma," Hepatology, Feb. 2006, pp. S145-S150, vol. 43, No. 2, Suppl. 1.

Tili, E. et al., "Expression and Function of Micro RNAs in Immune Cells During Normal or Disease State," International Journal of Medicine Sciences, 2008, pp. 73-79, vol. 5, No. 2.

Tockman, M. S. et al., "Considerations in Bringing a Cancer Biomarker to Clinical Application," Cancer Research, May 1992, pp. 2711s-2718s, vol. 52.

Trapasso, F. et al., "Fhit Interaction with Ferredoxin Reductase Triggers Generation of Reactive Oxygen Species and Apoptosis of Cancer Cells," Journal of Biological Chemistry, May 2008, pp. 13736-13744, vol. 283, No. 20.

Tricoli, J. V. et al., "MicroRNA: Potential for Cancer Detection, Diagnosis, and Prognosis," Cancer Research, May 2007, pp. 4553-4555, vol. 67, No. 10.

Ueda, T. et al., "Relation Between MicroRNA Expression and Progression and Prognosis of Gastric Cancer: A MicroRNA Expression Analysis," Published Online; www.thelancet.com/oncology, Dec. 2009, DO1:10.1016/S1470-2045(09)70343-2.

Uil, T.G. et al., "Generation of an Adenoviral Vector Containing an Addition of a Heterologous Ligand to the Serotpe 3 Fiber Knob," Cancer Gene Therapy, Feb. 2003, pp. 121-124, vol. 10, No. 2.

Valeri, N. et al., "Epigenetics, miRNAs, and Human Cancer: A New Chapter in Human Gene Regulation," Mamm Genome, Aug. 2009, pp. 573-580, vol. 20.

Valeri, N. et al., "Modulation of Mismatch Repair and Genomic Stability by miR-155," PNAS, Apr. 2010, pp. 6982-6987, vol. 107, No. 15.

(56) References Cited

OTHER PUBLICATIONS

Varnholt, H. et al., "MicroRNA Gene Expression Profile of Hepatitis C Virus-Associated Hepatocellular Carcinoma," Hepatology, Apr. 2008, pp. 1223-1232, Vo. 47, No. 4.

Vassilev et al., "In Vivo Activation of the p53 Pathway by Small-Molecule Antagonists of MDM2," Science, 2004, pp. 844-848, vol. 303.

Verschuur, A.C., "Acute Megakaryoblastic Leukemia," May 2004, pp. 1-5, Retrieved from the Internet: URL:http://www.orpga.net/data/patho/GB/uk-AMLM7.pdf.

Virgilio, L. et al., "Identification of the TCL1 Gene Involved in T-Call Malignancies," Proc. Natl. Acad. Sci., Dec. 1994, pp. 12530-12534, vol. 91.

Visone, R. et al., "MiRNAs and Cancer," The American Journal of Pathology, Apr. 2009, pp. 1131-1138, vol. 174, No. 4.

Volinia, et al., "Reprogramming of MirRNA Networks in Cancer and Leukemia," Genome Research, 2010, pp. 589-599, vol. 20.

Volinia, S. et al., "A MicroRNA Expression Signature of Human Solid Tumors Defines Cancer Gene Targets," PNAS, Feb. 2006, pp. 2257-2261, vol. 103, No. 7.

Wang, E. et al., "Ontogeny and Oncogenesis Balance the Transcriptional Profile of Renal Cell Cancer," Cancer Research, Oct. 2004, pp. 7279-7287, vol. 64.

Wang, X. et al., "Association Between CpG Island Methylation of the WWOX Gene and Its Expression in Breast Cancers," Tumor Biology, Feb. 2009, pp. 8-14, vol. 30.

Watson, D.I. et al., "MicroRNA Expression Profiles in Barrett's Oesophagus," RACS Annual Scientific Congress, 2007, pp. A45, vol. 77.

Weidhaas, J., "Using MicroRNAs to Understand Cancer Biology," Published Online Dec. 21, 2009, DOI: 10.1016/S1470-2045(09)70386-9.

Wiemer et al., "The Role of MicroRNAs in Cancer: No Small Matter," European Journal of Cancer, Jun. 12, 2007, vol. 43, No. 10, pp. 1529-1544.

Wijermans, P.W., "Low Dose Azanucleosidesfor High Risk (s) MDS and AML," Haematologica Reports, Nov. 2006, pp. 74-76. vol. 2, Issue, 15.

Xi, Y. et al., "Prognostic Values of MicroRNAs in Colorectal Cancer," Biomarker Insights, Jan. 2006, pp. 113-121, vol. 1.

Yamashita, T. et al., "EpCAM and α-Fetoprotein Expression Defines Novel Prognostic Subtypes of Hepatocellular Carcinoma," Cancer Research, Mar. 2008, pp. 1451-1461, vol. 68, No. 5.

Yamashita, T. et al., "Activation of Hepatic Stem Cell Marker EpCAM by Wnt-β-Catenin Signaling in Hepatocellular Carcinoma," Cancer Research, Nov. 2007, pp. 10831-10839, vol. 67, No. 22.

Yanaihara, N. et al., "Unique MicroRNA Molecular Profiles in Lung Cancer Diagnosis and Prognosis," Cancer Cell, Mar. 2006, pp. 189-198, vol. 9.

Yang, J. et al., "Analysis of Sequence Variations in 59 MicroRNAs in Hepatocellular Carcinomas," Mutation Research, Aug. 2008, pp. 205-209, vol. 638.

Yendamuri, S. et al., "WW Domain Containing Oxidoreductase Gene Expression is Altered in Non-Small Cell Lung Cancer," Cancer Research, Feb. 2003, pp. 878-881, vol. 63.

Yoon, S. et al., "Prediction of Regulatory Modules Comprising MicroRNAs and Target Genes," Bioinformatics Genes and Genomes, 2005. pp. ii93-ii100, vol. 21, Suppl. 2.

Yu, L.-G. et al., "Protein Phosphatase 2A, a Negative Regulator of the ERK Signaling Pathway, Is Activated by Tyrosine Phosphorylation of Putative HLA Class II-Associated Protein I (PHAPI)/pp32 in Response to the Antiproliferative Lectin, Jacalin," The Journal of Biological Chemisty, Jul. 2004, pp. 41377-41383, vol. 279, No. 40.

Zawacka-Pankau, J. et al., "Expression and Simple, One-Step Purification of Fragile Histidine Triad (Fhit) Tumor Suppressor Mutant Forms in *Escherichia coli* and their Interaction with Protoporphyrin IX," Biotechnology Letters, Jun. 2007, pp. 877-883, vol. 29, No. 6.

Zeng, Y. et al., "Recognition and Cleavage of Primary MicroRNA Precursors by the Nuclear Processing Enzyme Drosha," The EMBO Journal, 2005, pp. 138-148, vol. 24.

Zhang, L. et al., "Genomic and Epigenetic Alterations Deregulate MicroRNA Expression in Human Epithelial Ovarian Cancer," PNAS, May 2008, pp. 7004-7009, vol. 105, No. 19.

Zhang, L. et al., "MicroRNAs Exhibit High Frequency Genomic Alterations in Human Cancer," PNAS, Jun. 2006, pp. 9136-9141, vol. 103, No. 24.

Zhang, L. et al., Supporting Information, PNAS 2008, pp. 1-11.

Zhang, Z. et al., "Three Biomarkers Identified from Serum Proteomic Analysis for the Detection of Early Stage Ovarian Cancer," Cancer Research, Aug. 2004, pp. 5882-5890, vol. 64.

Zhao et al., "p53 Mediates the Negative Regulation of MDM2 by Orphan Receptor TR3," The EMBO Journal, 2006, pp. 5703-5715, vol. 25.

Zhu, S. et al., "MicroRNA-21 Targets the Tumor Suppressor Gene Tropomyosin 1 (TPM 1)," Journal of Biological Chemistry, May 2007, pp. 14328-14336, vol. 282, No. 19.

\* cited by examiner

Table 1. Mutations found in HPRT cDNAs prepared from 6-TG-resistant colonies of T47D, HCT116, and MDA-MB-231 cells

| Cell lines | Treatment | Number of clones analyzed | Clones without mutation in the coding sequence | Clones with frameshift mutation(s) | Clones with deletion(s) | Clones with only a single deletion | Clones with one or more exons lacking | Clones with other types of deletions | Clones with insertion(s) | Clones with transition(s) | Clones with transversion(s) |
|---|---|---|---|---|---|---|---|---|---|---|---|
| T47D | Mock | 24 | 0 | 12 | 14 | 17 | 24<br>Del ex. 3: 11<br>Del ex. 2+3: 9<br>Del ex. 4+5: 4 | 4<br>Del 1: 7 | 1<br>Ins 1: 1 | 4<br>Transitions: 5 | 0 |
| T47D | LSMCM | 40 | 0 | 20 | 40 | 25 | 38<br>Del ex. 3: 14<br>Del ex. 2+3: 16<br>Del ex. 4 + 5: 5<br>Del ex. 2+3+4: 1<br>Del ex. 6+7+8: 1<br>Del ex. 5: 1 | 11<br>Del ex. 17: 3 | 2<br>Ins 1: 3 | 7<br>Transitions: 7 | 1<br>Transitions: 3 |
| HCT116 | – Doxycycline | 14 | 1 | 13 | 13 | 0 | 0 | 13<br>Del 2: 1<br>Del 1: 12 | 4<br>Ins 1: 5 | 0 | 2<br>Transversions: 3 |
| HCT116 | – Doxycycline | 14 | 1 | 13 | 13 | 0 | 0 | 13<br>Del 2: 1<br>Del 1: 12 | 4<br>Ins 1: 5 | 0 | 2<br>Transversions: 2 |
| HCT116 | + Doxycycline | 25 | 4 | 18 | 11 | 0 | 2<br>Del ex. 3: 1<br>Del ex. 2+3: 1 | 9<br>Del 1: 16 | 13<br>Ins 1: 17 | 5 | 5<br>Transversions: 8 |
| MDA-MB-231 | – Doxycycline | 11 | 3 | 8 | 10 | 5 | 8<br>Del ex. 2+3: 1<br>Del ex. 7: 8 | 3<br>Del 1: 5 | 0 | 1<br>Transitions: 1 | 0 |
| MDA-MB-231 | + Doxycycline | 24 | 2 | 17 | 21 | 11 | 17<br>Del ex. 2: 1<br>Del ex. 2 + 3: 1<br>Del ex. 7: 16 | 9<br>Del 1: 17 | 0 | 4<br>Transitions: 6 | 2<br>Transversions: 2 |

Ex., exon; LSMCM, LPS-stimulated macrophage-conditioned medium; Mock, unstimulated macrophage-conditioned medium.

Figure 9

Table 2. Transcripts encoding factors related to DNA replication and maintenance whose levels decrease significantly following treatment of T47D and MDA-MB-231 cells

| Symbol | Gene name | Fold change |
|---|---|---|
| RFC5 | Replication factor C (activator 1) 5, 36.5kDa | 0.72 |
| NEIL3 | Nei endonuclease VIII-like 3 (*E. coli*) | 0.71 |
| AURKB | Aurora kinase B | 0.71 |
| GTSE1 | G-2 and S-phase expressed 1 | 0.64 |
| RAD54L | RAD54-like (*S. cerevisiae*) | 0.75 |
| ARL3 | ADP ribosylation factor-like 3 | 0.81 |
| BCCIP | BRCA2 and CDKN1A interacting protein | 0.77 |
| SKP2 | S-phase kinase-associated protein 2 (p45) | 0.65 |
| RDM1 | RAD52 motif 1 | 0.75 |
| PARP2 | Poly (ADP ribose) polymerase 2 | 0.86 |
| RAD54B | RAD54 homolog B (*S. cerevisiae*) | 0.67 |
| ERCC6L | Excision repair cross-complementing rodent repair deficiency, complementation group 6-like | 0.61 |
| DCTPP1 | dCTP pyrophosphatase 1 | 0.78 |
| DDB2 | Damage-specific DNA binding protein 2, 48kDa | 0.84 |
| CDKN2C | Cyclin-dependent kinase inhibitor 2C (p18, inhibits CDK4) | 0.64 |
| AK3L1 | Adenylate kinase 3-like 1 | 0.84 |
| APRT | Adenine phosphoribosyltransferase | 0.84 |
| DDB2 | Damage-specific DNA binding protein 2, 48kD | 0.84 |
| BRCC3 | BRCA1/BRCA2-containing complex, subunit 3 | 0.83 |
| TOP2A | Topoisomerase (DNA) II alpha 170kD | 0.77 |
| CDT1 | Chromatin licensing and DNA replication factor 1 | 0.74 |
| RECQL4 | RecQ protein-like | 0.72 |
| PARP1 | Poly (ADP ribose) polymerase 1 | 0.86 |

After Affymetrix microarray analyses, comparisons were done between two pools of cells treated with either unstimulated macrophage-conditioned medium or with LPS-stimulated macrophage-conditioned medium. The two pools contained four independent replicates from both T47D and MDA-MB-231 cell lines. Transcripts are arranged according to the decreasing values of $P$ (all $< 1 \times 10^{-7}$).

Figure 10

| Cell lines | Clones or experiments | Doxycycline (ng/ml) | Number of plated cells | Fold miR-155 up-regulation ± standard deviation | Number of 6-TG-resistant colonies | Average mutation rate | Fold increase of the average mutation rate |
|---|---|---|---|---|---|---|---|
| HCT116 cells | | 0 | $0.1 \times 10^7$ | | 112 | $560 \times 10^{-7}$ | |
| | | 500 | $0.1 \times 10^7$ | $19.57 \pm 0.62$ | 352 | $1570 \times 10^{-7}$ | 2.81 |
| SW620 clone 8A | Experiment 1 | 0 | $6 \times 10^7$ | | 12 | | |
| | | 500 | $6 \times 10^7$ | | 20 | | |
| | Experiment 2 | 0 | $6 \times 10^7$ | | 10 | | |
| | | 500 | $6 \times 10^7$ | | 14 | | |
| | Experiment 3 | 0 | $6 \times 10^7$ | | 11 | | |
| | | 500 | $6 \times 10^7$ | | 25 | | |
| | Total | 0 | $18 \times 10^7$ | | 33 | | |
| | | 500 | $18 \times 10^7$ | $2.94 \pm 0.23$ | 59 | $1.66 \times 10^{-7}$ | |
| SW620 clone 22C | Experiment 1 | 0 | $3.5 \times 10^7$ | | 7 | | |
| | | 500 | $3.5 \times 10^7$ | | 14 | | |
| | Experiment 2 | 0 | $3.5 \times 10^7$ | | 7 | | |
| | | 500 | $3.5 \times 10^7$ | | 15 | | |
| | Experiment 3 | 0 | $3.5 \times 10^7$ | | 5 | | |
| | | 500 | $3.5 \times 10^7$ | | 16 | | |
| | Total | 0 | $10.5 \times 10^7$ | | 19 | $0.75 \times 10^{-7}$ | |
| | | 500 | $10.5 \times 10^7$ | $5.58 \pm 0.43$ | 45 | $2.13 \times 10^{-7}$ | 2.86 |
| SW620 clone 23A | Experiment 1 | 0 | $2 \times 10^7$ | | 2 | | |
| | | 500 | $2 \times 10^7$ | | 12 | | |
| | Experiment 2 | 0 | $2 \times 10^7$ | | 2 | | |
| | | 500 | $2 \times 10^7$ | | 9 | | |
| | Experiment 3 | 0 | $2 \times 10^7$ | | 1 | | |
| | | 500 | $2 \times 10^7$ | | 10 | | |
| | Total | 0 | $6 \times 10^7$ | | 5 | $0.75 \times 10^{-7}$ | |
| | | 500 | $6 \times 10^7$ | $8.10 \pm 0.65$ | 31 | $2.53 \times 10^{-7}$ | 3.39 |
| MDA-MB-231 | Clone 9C | 0 | $4 \times 10^7$ | | 11 | $1.28 \times 10^{-7}$ | |
| | | 500 | $4 \times 10^7$ | $12.01 \pm 2.34$ | 16 | $1.98 \times 10^{-7}$ | 1.56 |
| MDA-MB-231 | Clone 2B | 0 | $2.5 \times 10^7$ | | 6 | $1.28 \times 10^{-7}$ | |
| | | 500 | $2.5 \times 10^7$ | $28.42 \pm 1.11$ | 15 | $2.74 \times 10^{-7}$ | 2.15 |
| MDA-MB-231 | Clone 19B | 0 | $2 \times 10^7$ | | 5 | $1.28 \times 10^{-7}$ | |
| | | 500 | $2 \times 10^7$ | $32.07 \pm 3.27$ | 20 | $4.42 \times 10^{-7}$ | 3.47 |

Table S1

Figure 11

| Table S3 | | | | | | | | | | | |
|---|---|---|---|---|---|---|---|---|---|---|---|
| Cellules | Treatment | Mutation type | Associated mutations | Associated mutation type | Nt positions | Exons | Coding / Untranslated region | Sequence context | SEQ ID NO: | Expected phenotypic change | Number of occurrences |
| T47D | Mock* | del 184 (frameshift) | no | | 302-485 | whole 3 | coding | GTCGTG-(ATTAGT...TATTGT)-AATGAC | 9 & 116 | loss of function | 8 |
| | | del 184 (frameshift) | yes | | 302-485 | whole 3 | coding | GTCGTG-(ATTAGT...TATTGT)-AATGAC | 9 & 116 | loss of function | 1 |
| | | | | transition | 505 | 4 | coding | GGG-GA>GC-ATA | 10 | Asp > Gly | 1 |
| | | del 184 (frameshift) | yes | | 302-485 | whole 3 | coding | GTCGTG-(ATTAGT...TATTGT)-AATGAC | 9 & 116 | loss of function | 1 |
| | | | | transition | 556 | 5 | coding | AAT-GT>CC-TTC | 11 | Val > Ala | |
| | | del 184 (frameshift) | yes | | 302-485 | whole 3 | coding | GTCGTG-(ATTAGT...TATTGT)-AATGAC | 9 & 116 | loss of function | 1 |
| | | | | del 1 | 1061, 1062 or 1063 | 9 | 3'-untranslated | TGT-A>(A)-TGA | 12 | none | |
| | | | | del 1 | 1066, 1067, 1068, 1069, 1070 or 1071 | 9 | 3'-untranslated | AATG-AAAAA(A)-TTCT | 13 | none | |
| | | del 291 (no frameshift) | no | | 195-485 | whole 2 + 3 | coding | GTCGTG-(ATTAGT...TATTGT)-AATGAC | 9 & 116 | loss of function | 8 |
| | | del 291 | yes | | 195-485 | whole 2 + 3 | coding | GTCGTG-(ATTAGT...TATTGT)-AATGAC | 9 & 116 | loss of function | 1 |
| | | | | del 1 | 195-485 | whole 2 + 3 | coding | GTCGTG-(ATTAGT...TATTGT)-AATGAC | 9 & 116 | loss of function | |
| | | | | del 1 | 1066, 1067, 1068, 1069, 1070 or 1071 | 9 | 3'-untranslated | AATG-AAAAA(A)-TTCT | 13 | none | |
| | | del 84 (no frameshift) | no | | 486-569 | whole 4 + 5 | coding | TATTGT-(AATGAC...GTGGAA)-GATATA | 14 & 117 | loss of function | 1 |
| | | del 84 | yes | | 486-569 | whole 4 + 5 | coding | TATTGT-(AATGAC...GTGGAA)-GATATA | 14 & 117 | loss of function | |

Figure 12

| Cell line | Treatment | Mutation type | Associated mutations | Associated mutation type | Nt positions | Exons | Coding/ Untranslated region | Sequence context | SEQ ID NO. | Expected phenotypic change | Number of occurrences |
|---|---|---|---|---|---|---|---|---|---|---|---|
| | | | | transition | 223 | 2 | coding | CCTT-GA(T>C)-TTAT | 15 | Asp <-> Asp | |
| | | | | transition | 407 | 3 | coding | GCTG-GA(T>C)-TACA | 16 | Asp <-> Asp | |
| | | del 84 | yes | | 486-569 | whole 4 + 5 | coding | TATTGT-(AATGAC...GTGGAA)-GATATA | 14 & 117 | loss of function | 1 |
| | | | | del 1 | 948, 949, 950 or 951 | 9 | 3'-untranslated | AGAA-TTTT(T)-ATCT | 17 | none | |
| | | del 84 | yes | | 486-569 | whole 4 + 5 | coding | TATTGT-(AATGAC...GTGGAA)-GATATA | 14 & 117 | loss of function | 1 |
| | | | | del 1 | 170 or 171 | 3 | coding | CCTT-AT(G)G-CGAC | 18 | frameshift (initiator codon) | |
| | | | | del 1 | 185 | 1 | coding | CAGC-CC(T)-GGCG | 19 | frameshift | |
| | | | | ins 1 | 344, 345 or 346 | 3 | coding | GAGC-CC(C)-ATCA | 20 | frameshift | |
| | | | | transition | 968 | 9 | 3'-untranslated | TACT-TT(A>G)-GAAA | 21 | none | |
| T47D | LSMCM | del 184 (frameshift) | no | | 302-485 | whole 3 | coding | GTCGTG-(ATTAGT...TATTGT)-AATGAC | 9 & 116 | loss of function | 13 |
| | | del 184 | yes | | 302-485 | whole 3 | coding | GTCGTG-(ATTAGT...TATTGT)-AATGAC | 9 & 116 | loss of function | 1 |
| | | | | del 1 | 1038, 1039 or 1040 | 9 | 3'-untranslated | CTTT-GCG-(C)GGATC | 22 | none | |
| | | del 184 | yes | | 302-485 | whole 3 | coding | GTCGTG-(ATTAGT...TATTGT)-AATGAC | 9 & 116 | loss of function | 1 |
| | | | | 3 transversions | 153, 157 and 161 | 1 | 5'-untranslated | CGCG-(C>G)-CGG-(C>G)-CGG-(C>G)-TCCG | 23 | none | |
| | | | | transition | 188 | 1 | coding | CGTT-(A>G)-TGGC | 24 | lack of initiator codon | |
| | | | | ins 1 | 925, 926, 927, 928, 929 or 930 | 9 | 3'-untranslated | GAGC-TTTTT(T)-GCAT | 25 | none | |

Figure 12 cont.

| Cellules | Treatment | Mutation type | Associated mutations | Associated mutation type | Nt positions | Exons | Coding / Untranslated region | Sequence context | SEQ ID NO: | Expected phenotypic change | Number of occurrences |
|---|---|---|---|---|---|---|---|---|---|---|---|
| | | del 184 | yes | | 302-485 | whole 3 | coding | GTCGTG-(ATTAGT...TATTGT)-AATGAC | 9 & 116 | loss of function | 1 |
| | | | | transition | 787 | 9 | coding | TTGT-G(T>C)C-ATTA | 26 | Val > Ala | |
| | | del 291 (no frameshift) | no | | 195-485 | whole 2 + 3 | coding | GTCGTG-(ATTAGT...TATTGT)-AATGAC | 9 & 116 | loss of function | 13 |
| | | del 291 | yes | | 195-485 | whole 2 + 3 | coding | GTCGTG-(ATTAGT...TATTGT)-AATGAC | 9 & 116 | loss of function | 1 |
| | | | | ins 1 | 1100, 1101, 1102 or 1103 | 9 | 3'-untranslated | GAGTG-AAA(A)-CATT | 27 | none | |
| | | del 291 | yes | | 195-485 | whole 2 + 3 | coding | GTCGTG-(ATTAGT...TATTGT)-AATGAC | 9 & 116 | loss of function | 1 |
| | | | | del 1 | 1066, 1067, 1068, 1069, 1070 or 1071 | 9 | 3'-untranslated | GAAACA-T(T)-GAAC | 28 | none | |
| | | del 291 | yes | | 195-485 | whole 2 + 3 | coding | GTCGTG-(ATTAGT...TATTGT)-AATGAC | 9 & 116 | loss of function | 1 |
| | | | | transition | 492 | 4 | coding | CCAG-TC(A>G)-ACAG | 29 | Ser <> Ser | |
| | | del 84 (no frameshift) | no | | 486-569 | whole 4 + 5 | coding | TATTGT-(AATGAC...GTGGAA)-GATATA | 14 & 117 | loss of function | 1 |
| | | del 84 | yes | | 486-569 | whole 4 + 5 | coding | TATTGT-(AATGAC...GTGGAA)-GATATA | 14 & 117 | loss of function | 1 |
| | | | | del 1 | 1045 or 1046 | 9 | 3'-untranslated | GCCG-AT(T)-GTTG | 30 | none | |
| | | | | del 1 | 1066, 1067, 1068, 1069, 1070 or 1071 | 9 | 3'-untranslated | AATG-AAAA(A)-TTCT | 13 | none | |
| | | | | del 1 | 1079, 1080 or 1081 | 9 | 3'-untranslated | TCTT-AA(A)-CCAC | 31 | none | |
| | | del 84 | yes | | 486-569 | whole 4 + 5 | coding | TATTGT-(AATGAC...GTGGAA)-GATATA | 14 & 117 | loss of function | 1 |

Figure 12 cont.

| Cellules | Treatment | Mutation type | Associated mutations | Associated mutation type | Nt positions | Exons | Coding / Untranslated region | Sequence context | SEQ ID NO: | Expected phenotypic change | Number of occurrences |
|---|---|---|---|---|---|---|---|---|---|---|---|
| | | | | del 1 | 145, 146 or 147 | 1 | 5'-untranslated | TCAG-CC(C)-GCGC | 32 | none | |
| | | | | del 1 | 152 | 1 | 5'-untranslated | GCGC-(G)-CCGG | 33 | none | |
| | | | | del 1 | 175, 176 or 177 | 1 | coding | GCGA-CC(C)-GCAG | 34 | frameshift | |
| | | | | del 1 | 208 or 209 | 2 | coding | TGAT-GA(A)-CCAG | 35 | frameshift | |
| | | | | del 1 | 210 | 2 | coding | TTAT-(G)ACCT | 36 | frameshift | |
| | | | | ins 1 | 257, 258 or 259 | 2 | coding | CTGA-(GAG)-ATTT | 37 | frameshift | |
| | | del 84 | yes | | 486-569 | whole 4 + 5 | coding | TATTGT-(AATGAC...GTGGAA)-GATATA | 14 & 117 | loss of function | 1 |
| | | | | del 3 | 168 | 1 | coding | CGTT-(A)-TGGC | 38 | lack of initiator codon | |
| | | del 84 | yes | | 486-569 | whole 4 + 5 | coding | TATTGT-(AATGAC...GTGGAA)-GATATA | 14 & 117 | loss of function | 1 |
| | | | | transition | 378 | 3 | coding | GCGG-(G>A)GC-TATA | 39 | Gly > Ser | |
| | | del 357 (no frameshift) | yes | | 195-551 | 2 + 3 + 4 | coding | GTCGTG-(ATTAGT...GGAAAG)-AATGTC | 40 & 118 | loss of function | 1 |
| | | | | transition | 787 | 9 | coding | TTGT-(GT>CC)-ATTA | 26 | Val > Ala | |
| | | del 207 (no frameshift) | | | 520-726 | 6 + 7 + 8 | coding | GTGGAA-(GATATA...TTGAAT)-CATGTT | 41 & 119 | loss of function | 1 |
| | | del 18 (no frameshift) | yes | | 552-569 | whole 5 | coding | GGAAAG-(AATGTC...GTGGAA)-GATATA | 42 & 120 | loss of function | 1 |
| | | | | del 3 | 145, 146 or 147 | 1 | 5'-untranslated | TCAG-CC(C)-GCGC | 32 | none | |
| | | | | del 1 | 208 or 209 | 2 | coding | GATG-A(A)-CCAG | 43 | frameshift | |
| | | del 17 (frameshift) | yes | | 595-611 | 6 | coding | AACAA-(TGCAGAC...TTCC)-TTCGT | 44 & 121 | frameshift | 1 |
| | | | | del 3 | 1079, 1080 or 1081 | 9 | 3'-untranslated | TCTT-AA(A)-CCAC | 31 | none | |

Figure 12 cont.

| CeBules | Treatment | Mutation type | Associated mutations | Associated mutation type | Nt positions | Exons | Coding / Untranslated region | Sequence context | SEQ ID NO: | Expected phenotype change | Number of occurrences |
|---|---|---|---|---|---|---|---|---|---|---|---|
| | | | | del 1 | 1093 or 1094 | 9 | 3'-untranslated | ACTA-T(T)-GAGT | 45 | none | |
| | | del 17 (frameshift) | yes | | 595-611 | 6 | coding | AACAA-(TGCAGAC...TTCC)-TTCGT | 44 & 121 | frameshift | 1 |
| | | | | del 1 | 1066, 1067, 1068, 1069, 1070 or 1071 | 9 | 3'-untranslated | AATG-AAAAA(A)-TTCT | 13 | none | |
| | | del 17 (frameshift) | yes | | 595-611 | 6 | coding | AACAA-(TGCAGAC...TTCC)-TTCGT | 44 & 121 | frameshift | 1 |
| | | | | del 1 | 170 or 171 | 1 | coding | GTTAT-G(G)-CGACC | 46 | frameshift | |
| | | | | del 1 | 175, 176 or 177 | 1 | coding | GCGA-CC(C)-GCAG | 34 | frameshift | |
| | | | | transition | 307 | 3 | coding | GACTG-(A>G)-ACGTC | 47 | Glu > Gly | |
| | | del 1 | yes | | 166 or 167 | 1 | 5'-untranslated | TCCG-T(T)-TGC | 48 | none | 1 |
| | | | | del 1 | 175, 176 or 177 | 1 | coding | GCGA-CC(C)-GCAG | 34 | frameshift | |
| | | | | del 1 | 260, 261 or 262 | 2 | coding | GAGGA-TT(T)-GGAAA | 49 | frameshift | |
| | | | | transition | 315 | 3 | coding | GTCTT-(G>A)-CTCGAG | 50 | Ala > Thr | |
| HCT116 | Doxycycline | del 1 | yes | | 145, 146 or 147 | 1 | 5'-untranslated | GTCAG-CC(C)-GCGCG | 51 | none | 1 |
| | | | | del 1 | 182, 183 or 184 | 1 | coding | CCGCAG-CC(C)-TGGCG | 52 | frameshift | |
| | | del 1 | yes | | 145, 146 or 147 | 1 | 5'-untranslated | GTCAG-CC(C)-GCGCG | 51 | none | 1 |
| | | | | del 1 | 153 or 154 | 1 | 5'-untranslated | GCGCG--C(C)-GBCCG | 53 | none | |
| | | | | del 2 | 602, 603 or 604 | 6 | coding | CAGAC-T(TT)-GCTTT | 54 | frameshift | |
| | | del 1 | yes | | 153 | 1 | 5'-untranslated | CGCGC-(G)-CCGGC | 55 | none | 1 |
| | | | | del 1 | 170 or 171 | 1 | coding | GTTAT-G(G)-CGACC | 46 | frameshift | |

Figure 12 cont.

| Cellules | Treatment | Mutation type | Associated mutation | Associated mutation type | Nt positions | Exons | Coding / Untranslated region | Sequence context | SEQ ID NO | Expected phenotypic change | Number of occurrences |
|---|---|---|---|---|---|---|---|---|---|---|---|
| | | | | del 1 | 182, 183 or 184 | 1 | coding | CCGCAG-CC(C)-TGGCG | 52 | frameshift | |
| | | del 1 | yes | | 152 | 1 | 5'-untranslated | CGCGC-(G)-CCGGC | 55 | none | 1 |
| | | | | del 3 | 155 or 156 | 1 | 5'-untranslated | GCGCC-G(G)-CCGGC | 56 | none | |
| | | | | del 1 | 182, 183 or 184 | 1 | coding | CCGCAG-CC(C)-TGGCG | 52 | frameshift | |
| | | del 1 | yes | | 153 or 154 | 1 | 5'-untranslated | GCGCG-C(C)-CGGCG | 53 | none | 1 |
| | | | | del 3 | 157 or 158 | 1 | 5'-untranslated | GCCCG-C(C)-GGCTC | 57 | none | |
| | | | | del 1 | 170 or 171 | 1 | coding | CTTAT-G(G)-CGACC | 46 | frameshift | |
| | | del 1 | yes | | 155 or 156 | 1 | 5'-untranslated | GCGCC-G(G)-CCGGC | 56 | none | 1 |
| | | | | del 3 | 170 or 171 | 1 | coding | CTTAT-G(G)-CGACC | 46 | frameshift | |
| | | | | del 1 | 182, 183 or 184 | 1 | coding | CCGCAG-CC(C)-TGGCG | 52 | frameshift | |
| | | del 1 | yes | | 170 or 171 | 1 | coding | CTTAT-G(G)-CGACC | 46 | frameshift | 1 |
| | | | | del 3 | 174, 175 or 176 | 1 | coding | GGCGA-CC(C)-GCAGC | 58 | frameshift | |
| | | | | del 3 | 182, 183 or 184 | 1 | coding | CCGCAG-CC(C)-TGGCG | 52 | frameshift | |
| | | | | del 3 | 196 or 197 | 2 | coding | CGTGA-T(T)-AGTGAT | 59 | frameshift | |
| | | del 3 | yes | | 182, 183 or 184 | 1 | coding | CCGCAG-CC(C)-TGGCG | 52 | frameshift | 1 |
| | | | | del 3 | 196 or 197 | 2 | coding | CGTGA-T(T)-AGTGAT | 59 | frameshift | |
| | | del 3 | yes | | 182, 183 or 184 | 1 | coding | CCGCAG-CC(C)-TGGCG | 52 | frameshift | 1 |
| | | | | transversion | 188 | 1 | coding | GCCCT-GG(G>A)-GTGAT | 60 | Gly <-> Gly | |
| | | | | del 3 | 191 | 1 | coding | GGCGT-(C)-GTGAT | 61 | frameshift | |
| | | | | del 1 | 196 or 197 | 2 | coding | CGTGA-T(T)-AGTGAT | 59 | frameshift | |
| | | del 1 | yes | | 170 or 171 | 1 | coding | CTTAT-G(G)-CGACC | 46 | frameshift | 1 |

Figure 12 cont.

| Cell lines | Treatment | Mutation type | Associated mutations | Associated mutation type | Nt positions | Exons | Coding / Untranslated region | Sequence context | SEQ ID NO: | Expected phenotypic change | Number of occurrences |
|---|---|---|---|---|---|---|---|---|---|---|---|
|  |  |  |  | del 1 | 182, 183 or 184 | 1 | coding | CCGCAG-CCCC-TGGCG | 52 | frameshift |  |
|  |  |  |  | del 1 | 196 or 197 | 2 | coding | CCTGA-T(T)-AGTGAT | 59 | frameshift |  |
|  |  |  |  | del 1 | 227, 228 or 229 | 2 | coding | CTTGA-TT(T)-ATTTG | 62 | frameshift |  |
|  |  |  |  | del 1 | 231, 232, 233 or 234 | 2 | coding | GATTTA-TT(T)-GCATA | 63 | frameshift |  |
|  |  | ins 1 | yes |  | 186, 187 or 188 | 1 | coding | GCCCT-G(G)-CGTCG | 64 | frameshift | 1 |
|  |  |  |  | del 1 | 190 | 1 | coding | TGGCG(T)-CGTGAT | 65 | frameshift |  |
|  |  |  |  | del 1 | 227, 228 or 229 | 2 | coding | CTTGA-TT(T)-ATTTG | 62 | frameshift |  |
|  |  |  |  | del 1 | 231, 232, 233 or 234 | 2 | coding | GATTTA-TT(T)-GCATA | 63 | frameshift |  |
|  |  | del 1 | yes |  | 188 | 1 | coding | CCTGG-(C)-GTCGT | 66 | frameshift | 1 |
|  |  |  |  | del 1 | 263 or 264 | 2 | coding | GATTT-C(C)-AAAGG | 67 | frameshift |  |
|  |  |  |  | ins 1 | 374, 375, 376, 377, 378 or 379 | 3 | coding | CTCAA-GGGGGG(G)-CTATA | 68 | frameshift |  |
|  |  |  |  | transversion | 596 | 6 | coding | ACA-AT(G>C)-CAGAC | 69 | Met > Ile |  |
|  |  |  |  | ins 1 | 601 | 6 | coding | GCAGA-(G)-CTTTG | 70 | frameshift |  |
|  |  | del 1 | yes |  | 260, 261 or 262 | 2 | coding | GAGGA-TT(T)-GGAAA | 49 | frameshift | 1 |
|  |  |  |  | ins 1 | 296, 297 or 298 | 2 | coding | ATTAT-GG(G)-ACAGG | 71 | frameshift |  |
|  |  | ins 1 | no |  | 1030, 1031 or 1032 | 9 | 3'-untranslated | TATCAG-TT(T)-CCCTT | 72 | none | 1 |
| HCT116 | Doxycycline | del 1 | yes |  | 145, 146 or 147 | 1 | 5'-untranslated | GTCAG-CC(C)-GCGCG | 51 | none | 1 |
|  |  |  |  | transversion | 182 | 1 | coding | CCCGC-AG(C>G)-CCTGG | 73 | Ser > Arg |  |
|  |  |  |  | del 1 | 196 or 197 | 2 | coding | CCTGA-T(T)-AGTGAT | 59 | frameshift |  |

Figure 12 cont.

| Cellules | Treatment | Mutation type | Associated mutations | Associated mutation type | Nt positions | Exons | Coding / Untranslated region | Sequence context | SEQ ID NO: | Expected phenotypic change | Number of occurrences |
|---|---|---|---|---|---|---|---|---|---|---|---|
| | | del 1 | yes | | 153 or 154 | 1 | 5'-untranslated | GCGCG-(C)-GGCCG | 74 | none | 1 |
| | | | | del 1 | 182, 183 or 184 | 1 | coding | CCGCAG-(C)-TGGCG | 52 | frameshift | |
| | | del 1 | yes | | 166 or 167 | 1 | 5'-untranslated | GCTCCG-(T)-ATGGC | 75 | none | 1 |
| | | | | del 1 | 181 | 1 | coding | GGGCA-(G)-CCCTG | 76 | frameshift | |
| | | | | transition | 657 | 7 | coding | GCTTG-(C>T)G-GTGAA | 77 | Leu <-> Leu | |
| | | del 1 | yes | | 180 | 1 | coding | CCGTTA-(T)-GCGCAC | 78 | lack of initiator codon | 1 |
| | | | | del 1 | 174, 175 or 176 | 1 | coding | GGCGA-(C)-GCAGC | 58 | frameshift | |
| | | | | del 1 | 215 or 216 | 2 | coding | CCAGG-(T)-TATGAC | 79 | frameshift | |
| | | | | transition | 657 | 7 | coding | GCTTG-(C>T)G-GTGAA | 77 | Leu <-> Leu | |
| | | del 1 | yes | | 170 or 171 | 1 | coding | GTTAT-(G)-CGACC | 46 | frameshift | 1 |
| | | | | del 1 | 182, 183 or 184 | 1 | coding | CCGCAG-(C)-TGGCG | 52 | frameshift | |
| | | del 291 (no frameshift) | yes | | 195-485 | whole 2 + 3 | coding | GTCGTG-(ATTAGT...TATTGT)-AATGAC | 9 & 116 | loss of function | 1 |
| | | | | transversion | 197 | 2 | coding | TCGTG-AT(T>A)-AGTGAT | 80 | Ile <-> Ile | |
| | | ins 1 | no | | 235 | 2 | coding | TATTTT-(C)-GCATA | 81 | frameshift | 4 |
| | | ins 1 | yes | | 235 | 2 | coding | TATTTT-(C)-GCATA | 81 | frameshift | 2 |
| | | | | transversion | 408 | 3 | coding | GCTGAC-(T>A)C-CTGGAT | 82 | Leu > Gln | |
| | | | | ins 1 | 407, 408 or 409 | 3 | coding | CTGGA-(T)-ACATC | 83 | frameshift | |
| | | ins 1 | yes | | 235 | 2 | coding | TATTTT-(C)-GCATA | 81 | frameshift | 1 |
| | | | | ins 1 | 406 or 407 | 3 | coding | GCTGG-A(A)-TTACA | 84 | frameshift | |
| | | ins 1 | yes | | 235 | 2 | coding | TATTTT-(C)-GCATA | 81 | frameshift | 1 |
| | | | | ins 1 | 410 or 411 | 3 | coding | GATTA-C(C)-ATCAA | 85 | frameshift | |

Figure 12 cont.

| Cellline | Treatment | Mutation type | Associated mutations | Associated mutation type | Nt positions | Exons | Coding / Untranslated region | Sequence context | SEQ ID NO: | Expected phenotypic change | Number of occurrences |
|---|---|---|---|---|---|---|---|---|---|---|---|
| | | ins 1 | yes | | 335 | 3 | coding | TATTT-(C)-GCATA | 84 | frameshift | 1 |
| | | | | transversion | 536 | 4 | coding | TCTC-TC(A>C)-ACTTT | 86 | Ser <-> Ser | |
| | | ins 1 | no | | 339 or 340 | 2 | coding | TGCAT-A(A)-CCTAA | 87 | frameshift | 1 |
| | | ins 1 | no | | 240, 241 or 242 | 2 | coding | GCATA-C(C)-TAATC | 88 | frameshift | 1 |
| | | del 184 (frameshift) | no | | 302-485 | whole 3 | coding | GTCGTG-(ATTAGT...TATTGT)-AATGAC | 9 & 116 | loss of function | 1 |
| | | transversion | yes | | 489 | 3 | coding | TGGAT-TA(>T)C-ATCAA | 89 | Tyr > Phe | 1 |
| | | | | transition | 686 | 6 | coding | GACTTG-(C>T)TT-TCCTT | 90 | Leu > Phe | |
| | | ins 1 | yes | | 410 | 3 | coding | GATTA-C(C)-ATCAA | 85 | frameshift | 1 |
| | | | | transition | 657 | ? | coding | GCTTG-(C>T)TG-GTGAA | 77 | Leu <-> Leu | |
| | | transition | yes | | 476 | 3 | coding | GACTG-AA(G>A)-AGCTA | 91 | Lys <-> Lys | 1 |
| | | | | ins 1 | 659, 660 or 661 | 7 | coding | TTGCT-GG(G)-TGAAA | 92 | frameshift | |
| | | | | ins 1 | 662 or 663 | 7 | coding | CTGGT-G(G)-AAAAG | 93 | frameshift | |
| | | | | transition | 667 | ? | coding | TGAAA-A(G>A)G-ACCCC | 94 | Arg > Lys | |
| | | | | transversion | 674 | ? | coding | GGACC-CCTA(>C)-CGAAG | 95 | Pro <-> Pro | |
| | | | | transversion | CCCCA-C(C>C)A-AGTGT | 7 | coding | CCCCA-C(C>C)A-AGTGT | 96 | Arg > Pro | |
| | | no mutation in CDS | | | del 1 | 196 or 197 | 1 | | | | 2 |
| | | no mutation in CDS | yes | | | | | | | | 1 |
| | | | | del 1 | 157 or 158 | 1 | 5'-untranslated | GCCGG-C(C)-GGCTC | 57 | none | |
| | | | | del 1 | 1057 or 1058 | 9 | 3'-untranslated | TTAAC-C(C)-GTAAA | 97 | none | |
| | | no mutation in CDS | yes | | | | | | | | 1 |

Figure 12 cont.

| Cellules | Treatment | Mutation type | Associated mutations | Associated mutation type | Nt positions | Exons | Coding / Untranslated region | Sequence context | SEQ ID NO: | Expected phenotypic change | Number of occurrences |
|---|---|---|---|---|---|---|---|---|---|---|---|
| | | | | del 1 | 157 or 158 | 1 | 5'-untranslated | GCCGG-(C)-GGCTC | 57 | none | |
| | | | | transition | 366 | 9 | 3'-untranslated | GTCCGA(T>C)TGACA | 98 | none | |
| MDA-MB-231 | - Doxycycline | del 47 (frameshift) | no | | 653-699 | whole 7 | coding | CGCAAG-(CTTGCT...C AGACT)-TTGTTG | 99 & 122 | loss of function | 5 |
| | | del 47 (frameshift) | yes | | 653-699 | whole 7 | coding | CGCAAG-(CTTGCT...C AGACT)-TTGTTG | 99 & 122 | loss of function | 1 |
| | | | | del 291 (no frameshift) | 195-485 | whole 2 + 3 | coding | GTCGTG-(ATTAGT... TATGGT)-AATGAC | 9 & 116 | loss of function | |
| | | del 47 (frameshift) | yes | | 653-699 | whole 7 | coding | CGCAAG-(CTTGCT...C AGACT)-TTGTTG | 99 & 122 | loss of function | 3 |
| | | | | transition | 365 | 3 | coding | CCCTC-T(T>C)-GTGCT | 100 | Cys <-> Cys | |
| | | del 47 (frameshift) | yes | | 653-699 | whole 7 | coding | CGCAAG-(CTTGCT...C AGACT)-TTGTTG | 99 & 122 | loss of function | 1 |
| | | | | del 1 | 1061, 1062 or 1063 | 9 | 3'-untranslated | TGT-AA(A)-TGA | 12 | none | |
| | | del 1 | yes | | 1038, 1039 or 1040 | 9 | 3'-untranslated | CCTTT-(GGG)-CGGAT | 101 | none | 1 |
| | | | | del 1 | 1072 or 1073 | 9 | 3'-untranslated | AAAAA-T(T)-CTCTT | 102 | none | |
| | | del 1 | yes | | 1061, 1062 or 1063 | 9 | 3'-untranslated | TGT-AA(A)-TGA | 12 | none | 3 |
| | | | | del 1 | 1066, 1067, 1068, 1069, 1070 or 1071 | 9 | 3'-untranslated | AATG-AAAAA(A)-TTCT | 13 | none | |
| | | no mutation | | | | | | | | | 3 |
| MDA-MB-231 | + Doxycycline | del 47 (frameshift) | no | | 653-699 | whole 7 | coding | CGCAAG-(CTTGCT...C AGACT)-TTGTTG | 99 & 122 | loss of function | 12 |
| | | del 47 (frameshift) | yes | | 653-699 | whole 7 | coding | CGCAAG-(CTTGCT...C AGACT)-TTGTTG | 99 & 122 | loss of function | 1 |

Figure 12 cont.

| Cellules | Treatment | Mutation type | Associated mutations | Associated mutation type | Nt positions | Exons | Coding / Untranslated region | Sequence context | SEQ ID NO: | Expected phenotype change | Number of occurrences |
|---|---|---|---|---|---|---|---|---|---|---|---|
| | | | | del 107 (frameshift) | | whole 2 | coding | GTCGTG-(ATTAGT...GGACAG)-GACTGA | 103 & 123 | loss of function | |
| | | | | del 291 (no frameshift) | 195-485 | whole 2 + 3 | coding | GTCGTG-(ATTAGT...TATTGT)-AATGAC | 9 & 126 | loss of function | |
| | | del 47 (frameshift) | yes | | 653-699 | whole 7 | coding | CGCAAG-(CTTGCT...CAGACT)-TTGTTG | 99 & 122 | loss of function | 1 |
| | | | | transition | 229 | 3 | coding | GCTTAT-G(A>G)C-CTTGAT | 104 | Asp > Gly | |
| | | | | del 1 | 1866, 1867, 1868, 1869, 1870 or 1871 | 9 | 3'-untranslated | AATG-AAAAA(A)-TTCT | 13 | none | |
| | | | | del 1 | 1861, 1862 or 1863 | 9 | 3'-untranslated | TGT-AA(A)-TGA | 12 | none | |
| | | | | del 1 | 1079, 1080 or 1081 | 9 | 3'-untranslated | TCTT-AA(A)-CCAC | 31 | none | |
| | | del 47 (frameshift) | yes | | 653-699 | whole 7 | coding | CGCAAG-(CTTGCT...CAGACT)-TTGTTG | 99 & 122 | loss of function | 2 |
| | | | | del 1 | 1861, 1862 or 1863 | 9 | 3'-untranslated | TGT-AA(A)-TGA | 12 | none | |
| | | | | del 1 | 1866, 1867, 1868, 1869, 1870 or 1871 | 9 | 3'-untranslated | AATG-AAAAA(A)-TTCT | 13 | none | |
| | | del 47 (frameshift) | yes | | 653-699 | whole 7 | coding | CGCAAG-(CTTGCT...CAGACT)-TTGTTG | 99 & 122 | loss of function | 2 |
| | | | | del 1 | 1866, 1867, 1868, 1869, 1870 or 1871 | 9 | 3'-untranslated | AATG-AAAAA(A)-TTCT | 13 | none | |
| | | transversion | yes | | 331 | 3 | coding | CTGAA-(GT>A)-CTTGC | 105 | Arg <> Arg | 1 |
| | | transition | | | 349 | 3 | coding | GCCAT-C(A>G)C-ATTGT | 106 | His > Arg | 1 |
| | | transition | | | 357 | 3 | coding | TTGTA-(G>A)CC-CTCTG | 107 | Ala > Thr | |
| | | transversion | | | 747 | 8 | coding | CCCTT-(G>T)AC-TATAA | 108 | Asp > Tyr | |

Figure 12 cont.

| Cellules | Treatment | Mutation type | Associated mutations | Associated mutation type | Nt positions | Exons | Coding / Untranslated region | Sequence context | SEQ ID NO: | Expected phenotypic change | Number of occurrences |
|---|---|---|---|---|---|---|---|---|---|---|---|
| | | transition | no | | 357 | 3 | coding | TTGTA-(G>A)CC-CTCTG | 107 | Ala > Thr | 1 |
| | | transition | yes | | 458 | 3 | coding | TGACT-GT(A>G)-GATTT | 108 | Val <-> Val | 1 |
| | | | | del 1 | 992, 993 or 994 | 9 | 3'-untranslated | TTCT-AA(A)-CTGTT | 110 | none | 1 |
| | | transition | yes | | 570 | 6 | coding | TGGAA-(G>A)AT-ATAAT | 111 | Asp > Asn | 1 |
| | | | | del 1 | 1066, 1067, 1068, 1069, 1070 or 1071 | 9 | 3'-untranslated | AATG-AAAAA(A)-TTCT | 13 | none | 1 |
| | | | | del 1 | 1082 or 1083 | 9 | 3'-untranslated | TTAAA-C(C)-ACAGC | 112 | none | 1 |
| | | | del 1 | yes | 1061, 1062 or 1063 | 9 | 3'-untranslated | TGT-AA(A)-TGA | 12 | none | 1 |
| | | | | del 1 | 1066, 1067, 1068, 1069, 1070 or 1071 | 9 | 3'-untranslated | AAATG-AAAAA(A)-TTCT | 113 | none | 1 |
| | | | | del 1 | 1100, 1101 or 1102 | 9 | 3'-untranslated | GAGTG-A(A)-CATTG | 114 | none | 1 |
| | | | del 1 | yes | 1066, 1067, 1068, 1069, 1070 or 1071 | 9 | 3'-untranslated | AAATG-AAAAA(A)-TTCTCT | 115 | none | 1 |
| | | | | del 1 | 1100, 1101 or 1102 | 9 | 3'-untranslated | GAGTG-A(A)-CATTG | 114 | none | 1 |

Figure 12 cont.

| Table S3 | |
|---|---|
| Factors | Main function |
| APC | Predicted target of *miR-155* (www.targetscan.org). APC is a tumor suppressor protein that acts as an antagonist of the Wnt signaling pathway. It is also involved in cell migration and adhesion, transcriptional activation, and apoptosis. |
| BACH1 | Involved in DNA replication checkpoint control. |
| CUTL1 / CUX1 | Dual function, acts as an oncogene or tumour suppressor gene depending on the cellular context. Together with E2F1 they regulate coordinated expression of the mitotic complex genes Ect2, MgcRacGAP, and MKLP1 in S phase. |
| FADD | Adaptor molecule that interacts with various cell surface receptors and mediates cell apoptotic signals. |
| FOXO3 | Triggers apoptosis through expression of many genes involved in cell death. |
| JARID2 | Negatively regulates cell proliferation and survival, also part of methyltransferase complex. |
| KGF / FGF-7 | Epithelial specific growth factor, it is down regulation by *miR-155* results in increased cell migration. |
| RhoA | Ectopic expression of miR-155 reduced RhoA protein and disrupted tight junction formation in mammary cells. |
| RIP1 | Induces necrotic cell death downstream of TNF signaling. |
| SHIP1 / INPP5D | Negative regulator of cell proliferation and survival. It is down regulation by *miR-155* results in activation of Akt. |
| SMAD1 | BMP signalling cascade. It is targeting by *miR-155* results in BMP induction of the cyclin-dependent kinase inhibitor p21 and it reverses BMP-mediated cell growth inhibition. |
| SMAD5 | Same as SMAD1 |
| HIVEP2 | Same as SMAD1 |
| MYO10 | Same as SMAD1 |
| SOCS1 | Negative regulator of cytokine signalling. It is down regulation by *miR-155* results in constitutive activation of STAT3 through the JAK pathway. |
| TP53INP | Proapoptotic stress-induced p53 target gene. |

Figure 13

SEQUENCE LISTING

```
<160> NUMBER OF SEQ ID NOS: 123

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atagcggccg cttaatgcta atcgtgatag gggtgaattc gcg              43

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgcgaattca cccctatcac gattagcatt aagcggccgc tat              43

<210> SEQ ID NO 3
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atagcggccg cctgttaatg ctaatcgtga tagggttttt tgcctccaac tgactcctac    60
atattagcat taacaggaat tcgcg                                         85

<210> SEQ ID NO 4
<211> LENGTH: 85
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 4
cgcgaattcc tgttaatgct aatatgtagg agtcagttgg aggcaaaaac ccctatcacg      60
attagcatta acaggcggcc gctat                                            85

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcgcgccggc cggctccgtt                                                  20

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggcgatgtca ataggactcc agatg                                            25

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gccggccggc tccgttatgg                                                  20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atgtcaatag gactccagat g                                                21

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gtcgtgatta gt                                                          12

<210> SEQ ID NO 10
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 10 ggggrcata                                                              9

<210> SEQ ID NO 11
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11 aatgycttg                                                              9

<210> SEQ ID NO 12
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: May or may not be present

<400> SEQUENCE: 12 tgtaaatga                                                              9

<210> SEQ ID NO 13
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: May or may not be present

<400> SEQUENCE: 13
aatgaaaaaa ttct                                                       14

<210> SEQ ID NO 14
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tattgtaatg ac                                                         12

<210> SEQ ID NO 15
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ccttgaytta t                                                          11

<210> SEQ ID NO 16
<211> LENGTH: 11
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gctggaytac a                                                          11

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: May or may not be present

<400> SEQUENCE: 17
agaattttat ct                                                         12

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: May or may not be present

<400> SEQUENCE: 18
cgttatggcg ac                                                         12

<210> SEQ ID NO 19
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 19
cagccctggc g                                                          11

<210> SEQ ID NO 20
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 20
gaggcccatc a                                                          11

<210> SEQ ID NO 21
```

```
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tactttrgaa a                                                            11

<210> SEQ ID NO 22
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 22
ctttgggcgg atc                                                          13

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cgcgscggsc ggstccg                                                      17

<210> SEQ ID NO 24
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24 cgttrtggc                                                                9

<210> SEQ ID NO 25
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: May or may not be present

<400> SEQUENCE: 25
gagctttttt gcat                                                         14

<210> SEQ ID NO 26
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 26
ttgtgycatt a                                                           11

<210> SEQ ID NO 27
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: May or may not be present

<400> SEQUENCE: 27
gagtgaaaac att                                                         13

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: May or may not be present

<400> SEQUENCE: 28
gaaacattga ac                                                          12

<210> SEQ ID NO 29
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ccagtcraca g                                                           11

<210> SEQ ID NO 30
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 30
gcggattgtt g                                                           11

<210> SEQ ID NO 31
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present
```

-continued

<400> SEQUENCE: 31
tcttaaacca c                                                                    11

<210> SEQ ID NO 32
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 32
tcagcccgcg c                                                                    11

<210> SEQ ID NO 33
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: May or may not be present

<400> SEQUENCE: 33 gcgcgccgg                                                                        9

<210> SEQ ID NO 34
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 34
gcgacccgca g                                                                    11

<210> SEQ ID NO 35
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 35
tgatgaacca g                                                                    11

<210> SEQ ID NO 36
<211> LENGTH: 9
<212> TYPE: DNA
<213> ORGANISM: Artificial Sequence
<220> FEATURE:
<223> OTHER INFORMATION: Description of Artificial Sequence: Synthetic

```
        oligonucleotide
<220> FEATURE:
<221> NAME/KEY: modified_base
<222> LOCATION: (5)..(5)
<223> OTHER INFORMATION: May or may not be present

<400> SEQUENCE: 36 ttatgacct                                                                    9

<210> SEQ ID NO 37
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 37
ctgagggatt t                                                                11

<210> SEQ ID NO 38
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: May or may not be present

<400> SEQUENCE: 38 cgttatggc                                                                    9

<210> SEQ ID NO 39
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ggggrgctat a                                                                11

<210> SEQ ID NO 40
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gtcgtgatta gt                                                               12

<210> SEQ ID NO 41
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
```

-continued gtggaagata ta                                                           12

<210> SEQ ID NO 42
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ggaaagaatg tc                                                           12

<210> SEQ ID NO 43
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: May or may not be present

<400> SEQUENCE: 43
gatgaaccag                                                              10

<210> SEQ ID NO 44
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aacaatgcag ac                                                           12

<210> SEQ ID NO 45
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: May or may not be present

<400> SEQUENCE: 45
actattgagt                                                              10

<210> SEQ ID NO 46
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 46
gttatggcga cc                                                           12

```
<210> SEQ ID NO 47
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gactgracgt c                                                           11

<210> SEQ ID NO 48
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: May or may not be present

<400> SEQUENCE: 48 tccgtttgc                                                               9

<210> SEQ ID NO 49
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: May or may not be present

<400> SEQUENCE: 49
gaggatttgg aaa                                                         13

<210> SEQ ID NO 50
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gtcttrctcg ag                                                          12

<210> SEQ ID NO 51
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: May or may not be present

<400> SEQUENCE: 51
gtcagcccgc gcg                                                         13

<210> SEQ ID NO 52
<211> LENGTH: 14
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: May or may not be present

<400> SEQUENCE: 52
ccgcagccct ggcg                                                    14

<210> SEQ ID NO 53
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 53
gcgcgccggc cg                                                      12

<210> SEQ ID NO 54
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: May or may not be present

<400> SEQUENCE: 54
cagactttgc ttt                                                     13

<210> SEQ ID NO 55
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: May or may not be present

<400> SEQUENCE: 55
cgcgcgccgg c                                                       11

<210> SEQ ID NO 56
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 56
```
gcgccggccg gc                                                              12

<210> SEQ ID NO 57
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 57
gccggccggc tc                                                              12

<210> SEQ ID NO 58
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: May or may not be present

<400> SEQUENCE: 58
ggcgacccgc agc                                                             13

<210> SEQ ID NO 59
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 59
cgtgattagt gat                                                             13

<210> SEQ ID NO 60
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gccctggmgt gat                                                             13

<210> SEQ ID NO 61
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: May or may not be present

<400> SEQUENCE: 61

```
ggcgtcgtga t                                                    11

<210> SEQ ID NO 62
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: May or may not be present

<400> SEQUENCE: 62
cttgatttat ttg                                                  13

<210> SEQ ID NO 63
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: May or may not be present

<400> SEQUENCE: 63
gatttatttt gcata                                                15

<210> SEQ ID NO 64
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: May or may not be present

<400> SEQUENCE: 64
gccctgggcg tcg                                                  13

<210> SEQ ID NO 65
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: May or may not be present

<400> SEQUENCE: 65
tggcgtcgtg at                                                   12

<210> SEQ ID NO 66
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (6)..(6)
<223> OTHER INFORMATION: May or may not be present

<400> SEQUENCE: 66
cctggcgtcg t                                                              11

<210> SEQ ID NO 67
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 67
gatttggaaa gg                                                             12

<210> SEQ ID NO 68
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: May or may not be present

<400> SEQUENCE: 68
ctcaaggggg ggctata                                                        17

<210> SEQ ID NO 69
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
acaatscaga c                                                              11

<210> SEQ ID NO 70
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: May or may not be present

<400> SEQUENCE: 70
gcagagcttt g                                                              11

<210> SEQ ID NO 71
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (8)..(8)
<223> OTHER INFORMATION: May or may not be present

<400> SEQUENCE: 71
attatgggac agg                                                            13

<210> SEQ ID NO 72
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: May or may not be present

<400> SEQUENCE: 72
tatcagtttc cctt                                                           14

<210> SEQ ID NO 73
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
cccgcagscc tgg                                                            13

<210> SEQ ID NO 74
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 74
gcgcgccggc cg                                                             12

<210> SEQ ID NO 75
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: May or may not be present

<400> SEQUENCE: 75
gctccgttat ggc                                                            13

<210> SEQ ID NO 76
<211> LENGTH: 11
<212> TYPE: DNA
<213> ORGANISM: Artificial Sequence
<220> FEATURE:
<223> OTHER INFORMATION: Description of Artificial Sequence: Synthetic
```

```
            oligonucleotide
<220> FEATURE:
<221> NAME/KEY: modified_base
<222> LOCATION: (6)..(6)
<223> OTHER INFORMATION: May or may not be present

<400> SEQUENCE: 76
gggcagccct g                                                          11

<210> SEQ ID NO 77
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gcttgytggt gaa                                                        13

<210> SEQ ID NO 78
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 78
ccgttatgcg cac                                                        13

<210> SEQ ID NO 79
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 79
ccaggtttat gac                                                        13

<210> SEQ ID NO 80
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tcgtgatwag tgat                                                       14

<210> SEQ ID NO 81
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (7)..(7)
<223> OTHER INFORMATION: May or may not be present

<400> SEQUENCE: 81
tattttcgca ta                                                         12

<210> SEQ ID NO 82
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gctgaccwcc tggat                                                      15

<210> SEQ ID NO 83
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: May or may not be present

<400> SEQUENCE: 83
ctggatttac atc                                                        13

<210> SEQ ID NO 84
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 84
gctggaatta ca                                                         12

<210> SEQ ID NO 85
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 85
gattaccatc aa                                                         12

<210> SEQ ID NO 86
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 86
tctctcmact tt                                                    12

<210> SEQ ID NO 87
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 87
tgcataacct aa                                                    12

<210> SEQ ID NO 88
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: May or may not be present

<400> SEQUENCE: 88
gcatacccta atc                                                   13

<210> SEQ ID NO 89
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
tggattwcat caa                                                   13

<210> SEQ ID NO 90
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gactttgytt tcctt                                                 15

<210> SEQ ID NO 91
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91 gactgaaarag cta                                                  13

<210> SEQ ID NO 92
<211> LENGTH: 13
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: May or may not be present

<400> SEQUENCE: 92
ttgctgggtg aaa                                                           13

<210> SEQ ID NO 93
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 93
ctggtggaaa ag                                                            12

<210> SEQ ID NO 94
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
tgaaaargac ccc                                                           13

<210> SEQ ID NO 95
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ggaccccmcg aag                                                           13

<210> SEQ ID NO 96
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ccccacsaag tgt                                                           13

<210> SEQ ID NO 97
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (7)..(7)
<223> OTHER INFORMATION: May or may not be present

<400> SEQUENCE: 97
ttaacccgta aa                                                          12

<210> SEQ ID NO 98
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gtccgaytga ca                                                          12

<210> SEQ ID NO 99
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
cgcaagcttg ct                                                          12

<210> SEQ ID NO 100
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ccctctgygt gct                                                         13

<210> SEQ ID NO 101
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: May or may not be present

<400> SEQUENCE: 101
cctttgggcg gat                                                         13

<210> SEQ ID NO 102
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 102
aaaaattctc tt                                                          12
```

<210> SEQ ID NO 103
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gtcgtgatta gt                                                          12

<210> SEQ ID NO 104
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
ggttatgrcc ttgat                                                       15

<210> SEQ ID NO 105
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ctgaacgwct tgc                                                         13

<210> SEQ ID NO 106
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gccatcrcat tgt                                                         13

<210> SEQ ID NO 107
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
ttgtarccct ctg                                                         13

<210> SEQ ID NO 108
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
cccttkacta taa                                                         13

<210> SEQ ID NO 109

```
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
tgactgtrga ttt                                                          13

<210> SEQ ID NO 110
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: May or may not be present

<400> SEQUENCE: 110
ttcctaaact gtt                                                          13

<210> SEQ ID NO 111
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tggaaratat aat                                                          13

<210> SEQ ID NO 112
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: May or may not be present

<400> SEQUENCE: 112
ttaaaccaca gc                                                           12

<210> SEQ ID NO 113
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: May or may not be present

<400> SEQUENCE: 113
aaatgaaaaa attct                                                        15

<210> SEQ ID NO 114
<211> LENGTH: 13
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: May or may not be present

<400> SEQUENCE: 114
gagtgaaaca ttg                                                            13

<210> SEQ ID NO 115
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: May or may not be present

<400> SEQUENCE: 115
aaatgaaaaa attctct                                                        17

<210> SEQ ID NO 116
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
tattgtaatg ac                                                             12

<210> SEQ ID NO 117
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gtggaagata ta                                                             12

<210> SEQ ID NO 118
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
ggaaagaatg tc                                                             12

<210> SEQ ID NO 119
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ttgaatcatg tt                                                             12
```

```
<210> SEQ ID NO 120
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gtggaagata ta                                                              12

<210> SEQ ID NO 121
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121 ttccttggt                                                                   9

<210> SEQ ID NO 122
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
cagactttgt tg                                                              12

<210> SEQ ID NO 123
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ggacaggact ga                                                              12
```

MUTATOR ACTIVITY INDUCED BY MICRORNA-155 (*MIR-155*) LINKS INFLAMMATION AND CANCER

CROSS-REFERENCE TO RELATED APPLICATIONS

This application claims the benefit of U.S. Provisional Application No. 61/449,854 filed Mar. 7, 2011, the entire disclosure of which is expressly incorporated herein by reference.

STATEMENT REGARDING FEDERALLY SPONSORED RESEARCH

This invention was made with government support under Grant No. CA123541, awarded by National Institutes of Health. The government has certain rights in this invention.

SEQUENCE LISTING

The instant application contains a Sequence Listing which has been submitted via EFS-web and is hereby incorporated by reference in its entirety. The ASCII copy, created on Mar. 6, 2012, is named 604_52873_SEQ_LIST_11137.txt, and is 34,668 bytes in size.

TECHNICAL FIELD AND INDUSTRIAL APPLICABILITY OF THE INVENTION

This invention relates generally to the field of molecular biology. Certain aspects of the invention include application in diagnostics, therapeutics, and prognostics of cancers and leukemias associated disorders.

BACKGROUND

There is no admission that the background art disclosed in this section legally constitutes prior art.

miRNAs repress gene expression by inhibiting mRNA translation or by promoting mRNA degradation and are considered to be master regulators of various processes, ranging from proliferation to apoptosis. Both loss and gain of miRNA function contribute to cancer development through the upregulation and silencing, respectively, of different target genes.

Chronic and persistent inflammation contributes to cancer development. Infection driven inflammation is involved in the pathogenesis of about 15-20% of human tumors. Tumor-infiltrating leukocytes, such as monocytes/macrophages, T lymphocytes, and neutrophils, are prime regulators of cancer inflammation. Furthermore, even tumors that are not epidemiologically linked to pathogens are characterized by the presence of an inflammatory component in their microenvironment.

SUMMARY

The present invention is based, at least in part, on the following information and discoveries, as described herein.

In a first broad aspect, there is provided herein a method for modulating WEE1 kinase expression levels in a target cell comprising: administering a microRNA-155 (miR-155) oligonucleotide to the target cell.

In another broad aspect, there is provided herein a method of modulating mutation of a target cell in a subject comprising: administering a miR-155 oligonucleotide to a target cell cells in the subject; and, measuring mutation of the target cell, wherein the target cell is a cancer cell or a precancerous cell.

In another broad aspect, there is provided herein a method of reducing spontaneous mutation rate of a cell in a subject in need thereof, comprising reducing endogenous levels of miR-155.

In another broad aspect, there is provided herein a method of reducing spontaneous mutation rate of an inflammation-related cancer cell in a subject in need thereof, comprising reducing endogenous levels of miR-155.

In another broad aspect, there is provided herein a method of slowing or inhibiting cell proliferation in a cancer cell or cancer cell population comprising: contacting the cell or cell population with a miR-155 antisense compound comprising a miR-155 oligonucleotide is complementary to a sequence at least 90% identical to mature microRNA-155, thereby slowing or inhibiting mutation of the cell or cell population.

In another broad aspect, there is provided herein a method of treating or preventing a miR-155 associated cancer, comprising: identifying a subject having, or suspected of having the miR-155 cancer; and, administering to the target cell a miR-155 oligonucleotide.

In another broad aspect, there is provided herein a method of treating or preventing an miR-155 associated-cancer comprising: identifying a subject having, or suspected of having the miR-155 associated cancer, and administering to the subject a miR-155 antisense compound comprising a miR-155 oligonucleotide having complementary at least 90% identical to mature microRNA-155.

In another broad aspect, there is provided herein a method of modulating the expression of one or more genes in a target cell, the genes being selected from: APC, adenomatous polyposis coli; FADD, Fas (TNFRSF6)-associated via death domain; FOXO3, forkhead box O3; KGF, keratinocyte growth factor; HIVEP2, HIV type I enhancerbinding protein 2; MYO10, myosin X; RHOA, Ras homolog gene family, member A; RIP1, receptorinteracting protein kinase 1; SHIP1, inositol polyphosphate-5-phosphatase; SMAD1/5, SMAD family member 1/5; SOCS1, suppressor of cytokine signaling 1; TP53INP, Tumor protein 53-induced nuclear protein 1, comprising:

contacting the target cell with a miR-155 oligonucleotide.

In certain embodiments, the miR-155 oligonucleotide comprises an antisense miR-155 oligonucleotide.

In certain embodiments, the miR-155 oligonucleotide comprises a miR-155 antisense compound.

In certain embodiments, the miR-155 oligonucleotide comprises a miR-155 antagonist compound.

In certain embodiments, the miR-155 oligonucleotide is selected from the group consisting of a mature miR-155 oligonucleotide, a pre-miR-155 oligonucleotide, and a miR-155 seed sequence.

In certain embodiments, the miR-155 antisense compound comprises a modified oligonucleotide consisting of 12 to 30 linked nucleosides, wherein the nucleobase sequence of the modified oligonucleotide is complementary to a sequence at least 80% identical to mature sequence of the modified oligonucleotide is complementary to a sequence at least 80% identical to mature miR-155, pre-miR-155, a miR-155 seed sequence, or a sequence fully complementary to the sequence of mature miR-155, pre-miR-155, or miR-155.

In certain embodiments, administering a miR-155 oligonucleotide comprises: administering an antisense miR-155 expression vector to a target cell; and expressing an antisense miR-155 in the target cell.

In certain embodiments, administering a miR-155 oligonucleotide comprises: administering a miR-155 expression vector to a target cell; and expressing a miR-155 in the target cell.

In certain embodiments, the miRNA-155 expression vector comprises a nucleic acid sequence encoding a miRNA-155 operably linked to a promoter.

In certain embodiments, the target cell is a cancer cell.

In certain embodiments, the target cell is a breast cancer or precancerous cell.

In certain embodiments, the target cell is a colon cancer or precancerous cell.

In certain embodiments, the target cell is a gastric cancer or precancerous cell In certain embodiments, the target cell is a lung cancer or precancerous cell.

In certain embodiments, the modulation comprises decreasing expression of the one or more genes.

In certain embodiments, the modified oligonucleotide has no more than two mismatches to the nucleobase sequence of mature miR-155.

In certain embodiments, the modulation comprises decreasing expression of the one or more genes.

In certain embodiments, the method comprises contacting the cell with an antisense miR-155 inhibitory RNA (155-I).

In certain embodiments, the cell is contacted with the antisense miR-155 inhibitory RNA (155-I) in an amount sufficient to increase WEE1 levels.

In another broad aspect, there is provided herein a method of reducing spontaneous mutation rate of an inflammation-related cancer cell in a subject in need thereof, comprising contacting the cell with an antisense miR-155 inhibitory RNA (1554).

In certain embodiments, the cell is contacted with the antisense miR-155 inhibitory RNA (155-I) in an amount sufficient to increase WEE1 levels.

In certain embodiments, the method comprises preventing the onset of an inflammatory-related cancer by modulating the up-regulation of miR-155 in a subject in need thereof.

In certain embodiments, the subject is human.

In another broad aspect, there is provided herein a composition useful for reducing spontaneous mutation rate of a cell in a subject in need thereof, comprising an antisense miR-155.

In another broad aspect, there is provided herein a method of identifying an agent that can be used to inhibit an inflammatory-related cancer comprising:

a) contacting miR-155 with an agent to be assessed;

b) contacting one or more target genes of miR-155 with an agent to be assessed; or c) contacting a combination thereof, wherein if the agent inhibits expression of miR-155, enhances expression of the target genes, or performs a combination thereof, then the agent can be used to inhibit proliferation of the inflammatory-related cancer.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE FIGURES

The patent or application file contains one or more drawings executed in color and/or one or more photographs. Copies of this patent or patent application publication with color drawing(s) and/or photograph(s) will be provided by the Patent Office upon request and payment of the necessary fee.

FIG. 1A and FIG. 1B. Average mutation rates of 6-TG-resistant colonies from SW620 (FIG. 1A) and MDA-MB-231 clones (FIG. 1B) stably expressing miR-155 and mock treated (Control) or treated with doxycycline (indicated clones) starting 48 h before 6-TG selection. *P=0.065; **P<0.006 (Student t tests).

FIG. 2A. The relative up-regulation of miR-155 in the indicated cell lines either mock treated or treated with LSMCM for 48 h were determined using qRT-PCR. The figure gives the ratios LPS-stimulated/unstimulated. Values represent mean±SD (n=3).

FIG. 2B. The relative up-regulation of miR-155 in MDA-MB-231 cells treated as indicated was determined using qRT-PCR.

FIG. 2C. The mutation rates (MR) in MDA-MB-231 cells were estimated by calculating the slopes of the curves following mock and TNF/LPS treatment (n=4 estimations of mutation frequency).

FIG. 2D. Ratios of 6-TG-resistant colonies in T47D cells treated with LSMCM for 48 h versus control mock-treated cells.

FIG. 3A. Phenotypes of 6-TG-resistant HCT116 colonies following 48-h mock treatment (−doxycycline) or 48-h doxycycline treatment (+doxycycline). HCT116 cells were transiently infected with pRetroX-Tight-PurmiR-155 and Tet-On constructs before doxycycline treatment.

FIG. 3B. Cells from MDA-MB-231 clone 19B were stained with CFSE before induction of miR-155 expression by doxycycline treatment. The proliferation rate was analyzed by flow cytometry 4 and 5 d later. The experiment was repeated two times with similar results.

FIG. 3C. The levels of WEE1 in T47D cells transfected with premiR-Control, premiR-155, or antisense miR-155 inhibitory RNA (155-I) and subsequently either mock treated or treated with LSMCM for 48 h were determined by Western blotting.

FIG. 3D. The levels of WEE1 in primary B cells isolated from the spleen of Eμ-miR-155 transgenic mice after transfection with premiR-Control or antisense miR-155 inhibitory RNA (155-I).

FIG. 4 shows the ratios of the values for mock-treated/doxycycline-treated cells. Values represent mean±SD (n=3).

FIG. 9. Table 1—Mutations found in HPRT cDNAs prepared from 6-thioguanine (6-TG)-resistant colonies of T47D, HCT116 and MDA-MB-231 cells.

FIG. 10. Table 2—Transcripts encoding factors related to DNA replication and maintenance whose levels decrease significantly following treatment of T47D and MDA-MB-231 cells.

FIG. 11. Table S1—Effects of miR-155 overexpression on the frequency of 6-thioguanine (6-TG)-resistant colonies and the average mutation rate. Mutations found in HPRT cDNAs prepared from 6-TG-resistant colonies of human HCT116 colon cancer cells and from human T47D and MDA-MB-231 breast cancer cells after exposure to LPS-stimulated macrophage-conditioned medium or doxycycline-induced overexpression of miR-155 microRNA.

FIG. 12. Table S2—Mutations found in hypoxanthine phosphoribosyltransferase (HPRT) cDNAs prepared from 6-GT-resistant colonies of human HCT116 colon cancer cells and from human T47D and MDA-MB-231 breast cancer cells after exposure to LPS-stimulated macrophage-conditioned medium or doxycycline-induce overexpression of miR-155 microRNA. Mutations found in hypoxanthine phosphoribosyltransferase (HPRT) cDNA prepared from 6-TG-resistant colonies of human HCT116 colon cancer cells and from human T47D and MDA-MB-231 breast cancer cells after exposure to LPS-stimulated macrophage-conditioned medium (LSMCM) or doxycycline-induced overexpression of miR-155 microRNA. The length of HPRT transcribed region was 1,415 nt. The HPRT region analyzed was nucleotides 123-1,110. $^a$Mock, unstimulated macrophage-conditioned medium. $^b$LSMCM, LPS-stimulated macrophage-conditioned medium. $^c$HPRT coding region, nucleotides 168-824.

FIG. 13. Table S3—Validated targets of miR-155 microRNA that play a role as tumor suppressors or regulators of cell homeostasis: APC, adenomatous polyposis coli; BACH1, BTB and CNC homology 1, basic leucine zipper transcription factor 1; CUTL1, cut-like homeobox 1; FADD, Fas (TNFRSF6)-associated via death domain; JARID2, jumonji, AT-rich interactive domain 2; FOXO3, forkhead box O3; KGF, keratinocyte growth factor; HIVEP2, HIV type I enhancer-binding protein 2; MYO10, myosin X; RHOA, Ras homolog gene family, member A; RIP1, receptorinteracting protein kinase 1; SHIP1, inositol polyphosphate-5-phosphatase; SMAD1/5, SMAD family member 1/5; SOCS1, suppressor of cytokine signaling 1; TP531NP, Tumor protein 53-induced nuclear protein 1.

DETAILED DESCRIPTION

Figure 1A:
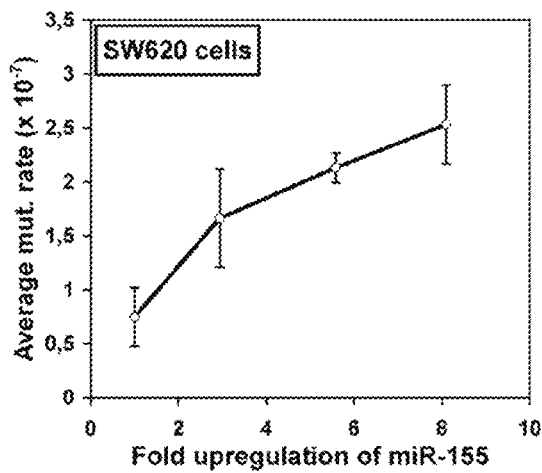
FIGS. 1A-1B. The average mutation rate in SW620 and MBA-MD-231 cells increases with the rate of miR-155 expression.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The present invention provides research tools, diagnostic methods, and therapeutical methods and compositions using the knowledge derived from this discovery. The invention is industrially applicable for the purpose of sensitizing tumor cells to drug-inducing apoptosis and also to inhibit tumor cell survival, proliferation and invasive capabilities.

Terms

It is to be understood that both the foregoing general description and the following detailed description are exemplary and explanatory only and are not intended to limit the scope of the current teachings. In this application, the use of the singular includes the plural unless specifically stated otherwise. In order to facilitate review of the various embodiments of the disclosure, the following explanations of specific terms are provided.

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The use of the word "a" or "an" when used in conjunction with the term "comprising" in the claims and/or the specification may mean "one," but it is also consistent with the meaning of "one or more," "at least one," and "one or more than one."

Also, the use of "comprise", "contain", and "include", or modifications of those root words, for example but not limited to, "comprises", "contained", and "including", are not intended to be limiting. The term "and/or" means that the terms before and after can be taken together or separately. For illustration purposes, but not as a limitation, "X and/or Y" can mean "X" or "Y" or "X and Y".

It is understood that a miRNA is derived from genomic sequences or a gene. In this respect, the term "gene" is used for simplicity to refer to the genomic sequence encoding the precursor miRNA for a given miRNA. However, embodiments of the invention may involve genomic sequences of a miRNA that are involved in its expression, such as a promoter or other regulatory sequences.

The terms "miR," "mir" and "miRNA" generally refer to microRNA, a class of small RNA molecules that are capable of modulating RNA translation (see, Zeng and Cullen, RNA, 9(1):112-123, 2003; Kidner and Martienssen Trends Genet, 19(1):13-6, 2003; Dennis C, Nature, 420(6917):732, 2002; Couzin J, Science 298(5602):2296-7, 2002, each of which is incorporated by reference herein).

MiRNA nucleic acid" generally refers to RNA or DNA that encodes a miR as defined above, or is complementary to a nucleic acid sequence encoding a miR, or hybridizes to such RNA or DNA and remains stably bound to it under appropriate stringency conditions. Particularly included are genomic DNA, cDNA, mRNA, miRNA and antisense molecules, pri-miRNA, pre-miRNA, mature miRNA, miRNA seed sequence; also included are nucleic acids based on alternative backbones or including alternative bases. mRNA nucleic acids can be derived from natural sources or synthesized.

The term "miRNA" generally refers to a single-stranded molecule, but in specific embodiments, molecules implemented in the invention will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complement(s)" of a particular sequence comprising a molecule. For example, precursor miRNA may have a self-complementary region, which is up to 100% complementary miRNA probes of the invention can be or be at least 60, 65, 70, 75, 80, 85, 90, 95, or 100% complementary to their target.

MicroRNAs are generally 21-23 nucleotides in length. MicroRNAs are processed from primary transcripts known as pri-miRNA to short stem-loop structures called precursor (pre)-miRNA and finally to functional, mature microRNA. Mature microRNA molecules are partially complementary to one or more messenger RNA molecules, and their primary function is to down-regulate gene expression. MicroRNAs regulate gene expression through the RNAi pathway.

"MicroRNA seed sequence," "miRNA seed sequence," "seed region" and "seed portion" are used to refer to nucleotides 2-7 or 2-8 of the mature miRNA sequence. The miRNA seed sequence is typically located at the 5' end of the miRNA.

The terms "miRNA-155" and "miR-155" are used interchangeably and, unless otherwise indicated, refer to microRNA-155, including miR-155, pri-miR-155, pre-miR-155, mature miR-155, miRNA-155 seed sequence, sequences comprising a miRNA-155 seed sequence, and variants thereof.

The terms "low miR-expression" and "high miR-expression" are relative terms that refer to the level of miR/s found in a sample. In some embodiments, low and high miR-expression are determined by comparison of miR/s levels in a group of cancerous samples and control or non-cancerous samples. Low and high expression can then be assigned to each sample based on whether the expression of a miR in a sample is above (high) or below (low) the average or median miR expression level. For individual samples, high or low miR expression can be determined by comparison of the sample to a control or reference sample known to have high or low expression, or by comparison to a standard value. Low and high miR expression can include expression of either the precursor or mature forms of miR, or both.

The term "expression vector" generally refers to a nucleic acid construct that can be generated recombinantly or synthetically. An expression vector generally includes a series of specified nucleic acid elements that enable transcription of a particular gene in a host cell. Generally, the gene expression is placed under the control of certain regulatory elements, such as constitutive or inducible promoters.

The term "operably linked" is used to describe the connection between regulatory elements and a gene or its coding region. That is, gene expression is typically placed under the control of certain regulatory elements, for example, without limitation, constitutive or inducible promoters, tissue-specific regulatory elements, and enhancers. A gene or coding region is the to be "operably linked to" or "operatively linked to" or "operably associated with" the regulatory elements, meaning that the gene or coding region is controlled or influenced by the regulatory element.

The term "combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB.

The terms "anticancer agent" and "anticancer drug" generally refer to any therapeutic agents (e.g., chemotherapeutic compounds and/or molecular therapeutic compounds), antisense therapies, radiation therapies, or surgical interventions, used in the treatment of hyperproliferative disease.

The term "adjunctive therapy" generally refers to a treatment used in combination with a primary treatment to improve the effects of the primary treatment.

The term "clinical outcome" generally refers to the health status of a subject following treatment for a disease or disorder, or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

The term "control" generally refers to a sample or standard used for comparison with an experimental sample, such as a tumor sample obtained from a subject. In some embodiments, the control is a sample obtained from a healthy subject or a non-cancerous sample obtained from a subject diagnosed. In some embodiments, the control is non-cancerous cell/tissue sample obtained from the same subject. In some embodiments, the control is a historical control or standard value (i.e., a previously tested control sample or group of samples that represent baseline or normal values, such as the level in a non-cancerous sample). In other embodiments, the control is a sample obtained from a healthy subject, such as a donor. Cancerous samples and non-cancerous tissue samples can be obtained according to any method known in the art.

The term "cytokines" generally refers to proteins produced by a wide variety of hematopoietic and non-hematopoietic cells that affect the behavior of other cells. Cytokines are important for both the innate and adaptive immune responses.

The term "decrease in survival" generally refers to a decrease in the length of time before death of a subject, or an increase in the risk of death for the subject.

The term "detecting the level of miR expression" generally refers to quantifying the amount of such miR present in a sample. Detecting expression of a miR, or any microRNA, can be achieved using any method known in the art or described herein, such as by qRT-PCR. Detecting expression of a miR includes detecting expression of either a mature form of the miR or a precursor form that is correlated with the miR expression. For example, miRNA detection methods involve sequence specific detection, such as by RT-PCR. miR-specific primers and probes can be designed using the precursor and mature miR nucleic acid sequences, which are known in the art and include modifications which do not change the function of the sequences.

The term "normal cell" generally refers to a cell that is not undergoing abnormal growth or division. Normal cells are non-cancerous and are not part of any hyperproliferative disease or disorder.

The term "anti-neoplastic agent" generally refers to any compound that retards the proliferation, growth, or spread of a targeted (e.g., malignant) neoplasm.

The terms "prevent," "preventing" and "prevention" generally refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention. "Preventing" a disease generally refers to inhibiting the full development of a disease.

The terms "treating" and/or "ameliorating a disease" generally refer to a therapeutic intervention that ameliorates a sign or symptom of a disease or pathological condition after it has begun to develop. "Ameliorating" generally refers to the reduction in the number or severity of signs or symptoms of a disease.

The term "subject" includes human and non-human animals. The preferred subject for treatment is a human. "Subject" and "subject" are used interchangeably herein.

The term "therapeutic" generally is a generic term that includes both diagnosis and treatment.

The term "therapeutic agent" generally refers to a chemical compound, small molecule, or other composition, such as an antisense compound, protein, peptide, small molecule, nucleic acid. antibody, protease inhibitor, hormone, chemokine or cytokine, capable of inducing a desired therapeutic or prophylactic effect when properly administered to a subject. For example, therapeutic agents include agents that prevent or inhibit development or metastasis. As used herein, a "candidate agent" is a compound selected for screening to determine if it can function as a therapeutic agent. "Incubating" includes a sufficient amount of time for an agent to interact with a cell or tissue. "Contacting" includes incubating an agent in solid or in liquid form with a cell or tissue. "Treating" a cell or tissue with an agent includes contacting or incubating the agent with the cell or tissue.

The term "therapeutically effective amount" generally refers to that amount of the therapeutic agent sufficient to result in amelioration of one or more symptoms of a disorder, or prevent advancement of a disorder, or cause regression of the disorder. For example, with respect to the treatment of cancer, in one embodiment, a therapeutically effective amount will refer to the amount of a therapeutic agent that decreases the rate of tumor growth, decreases tumor mass, decreases the number of metastases, increases time to tumor progression, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

A "therapeutically effective amount" can be a quantity of a specified pharmaceutical or therapeutic agent sufficient to achieve a desired effect in a subject, or in a cell, being treated with the agent. For example, this can be the amount of a therapeutic agent that alters the expression of miR/s, and thereby prevents, treats or ameliorates the disease or disorder in a subject. The effective amount of the agent will be dependent on several factors, including, but not limited to the subject or cells being treated, and the manner of administration of the therapeutic composition.

The term "pharmaceutically acceptable vehicles" generally refers to such pharmaceutically acceptable carriers (vehicles) as would be generally used. Remington's Pharmaceutical Sciences, by E. W. Martin, Mack Publishing Co., Easton, Pa., 15th Edition (1975), describes compositions and formulations suitable for pharmaceutical delivery of one or more therapeutic compounds, molecules or agents. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The term "pharmaceutically acceptable salt" generally refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts. Examples of bases include, but are not limited to, alkali metal (e.g., sodium) hydroxides, alkaline earth metal (e.g., magnesium) hydroxides, ammonia, and the like. Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound miR-155 Nucleic Acid Molecules Nucleic acid molecules that encode miR-155 are used in various embodiments of the present invention. miR-155 sequences for mature miR-155, pre-miR-155 can be used in some embodiments. In other embodiments cDNAs encoding mature miR-155 and pre-miR-155 can be used. Nucleic acid molecules encoding pri-miR-155 can also be used in some embodiments. A miRNA sequence may comprise from about 6 to about 99 or more nucleotides. In some embodiments, a miRNA sequence comprises about the first 6 to about the first 22 nucleotides of a pre-miRNA-155. Isolated or purified polynucleotides having at least 6 nucleotides (i.e., a hybridizable portion) of a miR-155 coding sequence or its complement are used in some embodiments. In other embodiments, miR-155 polynucleotides preferably comprise at least 22 (continuous) nucleotides, or a full-length miR-155 coding sequence.

In some embodiments, nucleic acids are used that are capable of blocking the activity of a miRNA (anti-miRNA or anti-miR). Such nucleic acids include, for example, antisense miR-155. For example, a "miR-155 antagonist" means an agent designed to interfere with or inhibit the activity of miRNA-155.

In certain embodiments, the miR-155 antagonist can be comprised of an antisense compound targeted to a miRNA. For example, the miR-155 antagonist comprises can be comprised of a small molecule, or the like that interferes with or inhibits the activity of an miRNA.

In certain embodiments, the miR-155 antagonist can be comprised of a modified oligonucleotide having a nucleobase sequence that is complementary to the nucleobase sequence of a miRNA, or a precursor thereof.

In certain embodiments, the anti-miR is an antisense miR-155 nucleic acid comprising a total of about 5 to about 100 or more, more preferably about 10 to about 60 nucleotides, and has a sequence that is preferably complementary to at least the seed region of miR-155. In particularly preferred embodiments, an anti-miRNA may comprise a total of at least about 5, to about 26 nucleotides. In some embodiments, the sequence of the anti-miRNA can comprise at least 5 nucleotides that are substantially complementary to the 5' region of a miR-155, at least 5 nucleotides that are substantially complementary to the 3' region of a miR-155, at least 4-7 nucleotides that are substantially complementary to a miR-155 seed sequence, or at least 5-12 nucleotide that are substantially complementary to the flanking regions of a miR-155 seed sequence.

In some embodiments, an anti-miR-155 comprises the complement of a sequence of a miRNA. In other embodiments an anti-miR-155 comprises the complement of the seed sequence or is able to hybridize under stringent conditions to the seed sequence. Preferred molecules are those that are able to hybridize under stringent conditions to the complement of a cDNA encoding a mature miR-155.

It is to be understood that the methods described herein are not limited by the source of the miR-155 or anti-miR-155. The miR-155 can be from a human or non-human mammal, derived from any recombinant source, synthesized in vitro or by chemical synthesis. The nucleotide may be DNA or RNA and may exist in a double-stranded, single-stranded or partially double-stranded form, depending on the particular context. miR-155 and anti-miR-155 nucleic acids may be prepared by any conventional means typically used to prepare nucleic acids in large quantity. For example, nucleic acids may be chemically synthesized using commercially available reagents and synthesizers by methods that are well-known in the art and/or using automated synthesis methods.

It is also be understood that the methods described herein are not limited to naturally occurring miR-155 sequences; rather, mutants and variants of miR-155 sequences are also within the contemplated scope. For example, nucleotide sequences that encode a mutant of a miR-155 that is a miR-155 with one or more substitutions, additions and/or deletions, and fragments of miR-155 as well as truncated versions of miR-155 maybe also be useful in the methods described herein.

It is also to be understood that, in certain embodiments, in order to increase the stability and/or optimize the delivery of the sense or antisense oligonucleotides, modified nucleotides or backbone modifications can be used. In some embodiments, a miR-155 or anti-miR-155 oligonucleotide can be modified to enhance delivery to target cells. Nucleic acid molecules encoding miR-155 and anti-miR-155 can be used in some embodiments to modulate function, activity and/or proliferation of immune cells.

miR-155 Expression Vectors

Expression vectors that contain a miR-155 or anti-miR-155 coding sequence can be used to deliver a miR-155 or anti-miR155 to target cells. In certain embodiments, expression vectors can contain a miR-155 sequence and/or anti-miR-155 sequence, optionally associated with a regulatory element that directs the expression of the coding sequence in a target cell. It is to be understood that the selection of particular vectors and/or expression control sequences to which the encoding sequence is operably linked generally depends (as is understood by those skilled in the art) on the particular functional properties desired; for example, the host cell to be transformed.

It is also to be understood that vectors useful with the methods described herein are preferably capable of directing replication in an appropriate host and of expression of a miR-155 or anti-miR-155 in a target cell.

It is also to be understood that a useful vector can include a selection gene whose expression confers a detectable marker such as a drug resistance. Non-limiting examples of selection genes include those vectors that encode proteins that confer resistance to antibiotics or other toxins, e.g., ampicillin, neomycin, methotrexate, or tetracycline, complement auxotrophic deficiencies, or supply critical nutrients withheld from the media. It is also to be understood that the detectable marker can optionally be present on a separate plasmid and introduced by co-transfection.

It is also to be understood that expression control elements can be used to regulate the expression of an operably linked coding sequence. Non-limiting examples include: inducible promoters, constitutive promoters, enhancers, and other regulatory elements. In some embodiments an inducible promoter is used that is readily controlled, such as being responsive to a nutrient in the target cell's medium. In some embodiments, the promoter is the U6 promoter or CMV promoter. It is also to be understood that other methods, vectors, and target cells suitable for adaptation to the expression of miR-155 in target cells can be readily adapted to the specific circumstances.

Delivery of Oligonucleotides and Expression Vectors to a Target Cell or Tissue

In certain embodiments, a miR-155 or anti-miR-155 oligonucleotide is delivered to a target cell. In other embodiments, an expression vector encoding a miR-155 or anti-miR-155 is delivered to a target cell where the miR-155 or anti-miR-155 is expressed. It is to be understood that different methods for delivery of oligonucleotides and expression vectors to target cells can be used.

In certain embodiments, the target cells may be present in a host, such as in a mammal, or may be in culture outside of a host. Thus, the delivery of miR-155 or anti-miR-155 to target cells in vivo, ex vivo and in vitro can accomplished in a suitable manner. In certain embodiments, a miR-155 or anti-miR-155 oligonucleotide is delivered to a target organ or tissue. Target organs and tissues may include locations where cancer cells or precursors of such cells are known to be located and may include, for example, solid cancers such as breast, colon, gastric and lung cancers.

In certain embodiments, cell development, function, proliferation and/or activity is modulated by delivering miR-155 or anti miR-155.

In certain embodiments, the mutation of a cell can be modulated (e.g., suppressed) by administering a miRNA-155 or anti-miR-155 oligonucleotide to the B cells. The numbers and/or activity of the cells can be modulated by administering a miRNA-155 or anti-miR-155 oligonucleotide to the cancer cells or to pre-cancerous cells.

In certain embodiments, the immune function and/or development of the cells can be modulated by delivering miR-155 or anti-miR-155 to the cells.

It is to be understood that the delivery of oligonucleotides and/or expression vectors to a target cell can be accomplished using different methods. In certain embodiments, a transfection agent can be used. In general, a transfection agent (e.g., a transfection reagent and/or delivery vehicle) can be a compound or compounds that bind(s) to or complex(es) with oligonucleotides and polynucleotides, and enhances their entry into cells. Non-limiting examples of useful transfection reagents include: cationic liposomes and lipids, polyamines, calcium phosphate precipitates, polycations, histone proteins, polyethylenimine, polylysine, and polyampholyte complexes. Another delivery method can include electroporating miRNA/s into a cell without inducing significant cell death. In addition, miRNAs can be transfected at different concentrations.

Non-limiting examples of useful reagents for delivery of miRNA, anti-miRNA and expression vectors include: protein and polymer complexes (polyplexes), lipids and liposomes (lipoplexes), combinations of polymers and lipids (lipopolyplexes), and multilayered and recharged particles. Transfection agents may also condense nucleic acids. Transfection agents may also be used to associate functional groups with a polynucleotide. Functional groups can include cell targeting moieties, cell receptor ligands, nuclear localization signals, compounds that enhance release of contents from endosomes or other intracellular vesicles (such as membrane active compounds), and other compounds that alter the behavior or interactions of the compound or complex to which they are attached (interaction modifiers).

In certain embodiments, miR-155 or anti-miR-155 nucleic acids and a transfection reagent can be delivered systematically such as by injection. In other embodiments, they may be injected into particular areas comprising target cells, such as particular organs, for example a solid cancer tissue. The skilled artisan will be able to select and use an appropriate system for delivering miRNA-155, anti-miRNA-155 or an expression vector to target cells in vivo, ex vivo and/or in vitro without undue experimentation.

General Description

Described herein are the effects of miR-155 overexpression and proinflammatory environment on the frequency of spontaneous hypoxanthine phosphoribosyltransferase (HPRT) mutations that can be detected based on the resistance to 6-thioguanine (6-TG). Both miR-155 overexpression and inflammatory environment increased the frequency of HPRT mutations and down-regulated WEE1, a kinase that blocks cell-cycle progression. The increased frequency of HPRT mutation was only modestly attributable to defects in mismatch repair machinery. This result shows that miR-155 enhances the mutation rate by simultaneously targeting different genes that suppress mutations and decreasing the efficiency of DNA safeguard mechanisms by targeting of cell-cycle regulators such as WEE1.

By simultaneously targeting tumor suppressor genes and inducing a mutator phenotype, miR-155 allows the selection of gene alterations required for tumor development and progression. The drugs reducing endogenous miR-155 levels are thus useful in the treatment of inflammation-related cancers.

Described herein are results showing that the mutator activity of miR-155 and that of the miR-155-linked inflammatory environment are key mechanisms connecting inflammation and cancer. Also described herein are results that show that miR-155 and inflammatory stimuli increase the spontaneous mutation rate.

Also provided are methods to treat suppress mutation rates in subject in need of such treatment, comprising administering a pharmaceutically-effective amount of a miR-155 composition herein.

Also provided are methods to treat cancer in a subject in need of such treatment, comprising administering a pharmaceutically-effective amount of an anti-sense miRNA, wherein the antisense miRNA is antisense to miRNA-155.

Also provided are methods for inducing apoptosis of rapidly mutating cells, comprising introducing an apoptosis-effective amount of a composition as described herein. In certain embodiments, the method comprises introducing an apoptosis-effective amount of an anti-sense miRNA, wherein the antisense miRNA is antisense to miR-155.

Also provided are methods for identifying pharmaceutically-useful compositions, comprising: introducing an antisense miRNA-155 to a cell culture; introducing a test composition to the cell culture; and identifying test compositions which induce apoptosis as pharmaceutically-useful compositions.

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLE I

Results

Overexpression of MiR-155 Results in Enhanced Mutation Rate.

Human miR-155 resides in the non-coding BIC transcript (EMBL:AF402776), located on chromosome 21. miR-155 targets core components of the DNA mismatch repair (MMR) machinery, among other mutator pathways, suggesting that elevated levels of miR-155 might enhance the rate of spontaneous mutations.

To measure the mutation rate, hypoxanthine phosphoribosyltransferase (HPRT) locus was used as the method for estimating mutation rate. The HPRT enzyme catalyzes the conversion of guanine into guanine monophosphate and hypoxanthine into inosine monophosphate in the purine salvage pathway.

Figure 4:
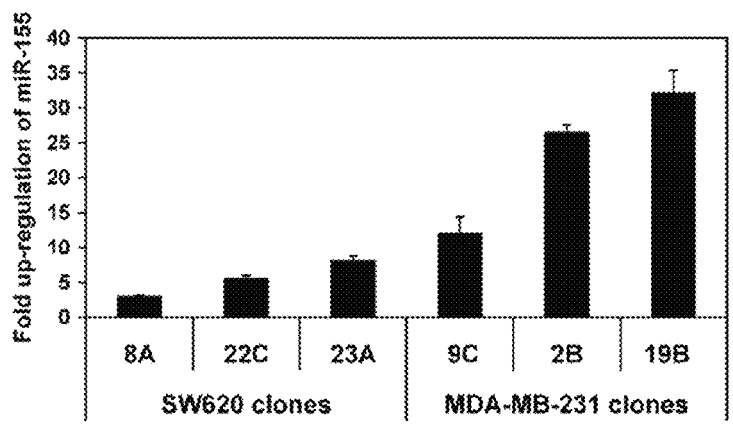
FIG. 4. The levels of microRNA-155 (miR-155) expression vary with the clones and the cell lines. SW620 and MDA-MB-231 clones stably transfected with a pRetroX-tight-Pur construct expressing mature miR-155 were mock treated or treated with doxycycline for 48 h. The relative levels of miR-155 were determined subsequently using quantitative RT-PCR.

The loss of HPRT function confers resistance to 6-thioguanine (6-TG), because 6-TG becomes cytotoxic only after phosphoribosylation by HPRT. This resistance can be used to identify cells that have acquired mutations at the HPRT locus. Because the acquired mutations are thought to occur randomly, the HPRT gene can be used as a reporter gene, and the frequency of mutation at the HPRT locus can be used as an estimate of global genomic instability. To measure the effects of miR-155 on mutation rate, the inventor first developed stable clones of SW620 colorectal adenocarcinoma cells and MDA-MB-231 breast adenocarcinoma cells expressing mature miR-155 under the control of the Tet-On inducible system. Incubation of SW620 clones 8A, 22C, and 23A with doxycycline increased miR-155 expression by 2.94±0.23-, 5.58±0.43-, and 8.10±0.65-fold, respectively (mean±SD) (FIG. 4 and FIG. 11—Table S1).

Figure 1B:
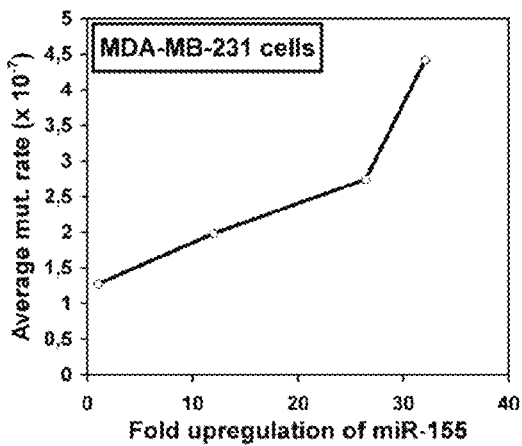

Similarly, doxycycline treatment increased miR-155 expression by 12.01±2.34-, 26.42±1.11-, and 32.07±3.27-fold in MDA-MB-231 clones 9C, 2B, and 19B, respectively. The cell growth-adjusted HPRT mutation rate, estimated based on a modified version of fluctuation analysis, increased with miR-155 levels in both SW620 and MDA-MB-231 cell clones (FIG. 1A and FIG. 1B). Constant elevated expression of miR-155 the enhanced mutation rate by up to 3.39-fold in SW620 clones and up to 3.47-fold in MDA-MB-231 clones (FIG. 11—Table S1).

Figure 5:
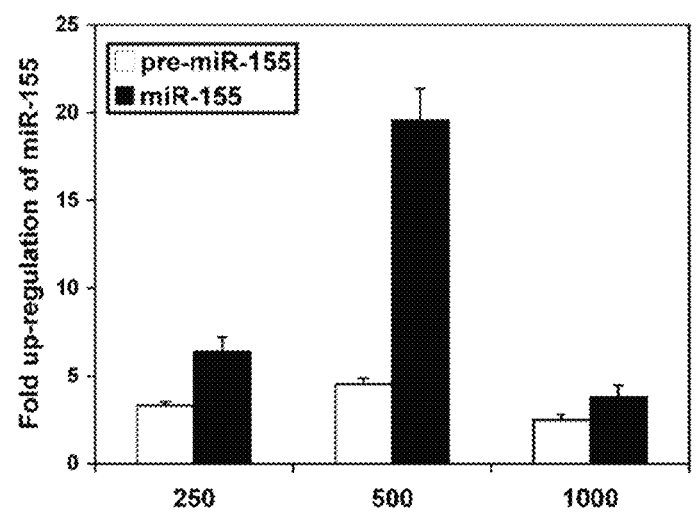
FIG. 5. Effects of increasing doses of doxycycline on the expression of miR-155. HCT116 cells were transiently transfected with a pRetroX-Tight-Pur construct expressing miR-155 precursor (premiR-155) or miR-155 mature form (miR-155) before 48-h treatment with the indicated doses of doxycycline (ng/mL).

Moreover, HCT116 colorectal carcinoma cells transiently overexpressing miR-155 by 19.57±0.62-fold under the control of Tet-On inducible system (FIG. 5) showed a 2.81-fold higher mutation rate (FIG. 11—Table S1). These results establish a direct link between mutation rate and miR-155 levels.

The basal spontaneous cell growth-adjusted mutation rates of SW620 and MDA-MB-231 cells was comparable ($0.75\pm0.27\times10^{-7}$ and $1.28\times10^{-7}$ mutations per cell, respectively) and were ~440-fold lower than the spontaneous mutation rate of HCT116 cells ($560\times10^{-7}$ mutations per cell) (FIG. 11—Table S1), because HCT116 cells contain a deletion of the hMLH1 MMR gene. The deletion of the hMLH1 MMR gene decreased the 155-induced mutator activity only partially, showing that miR-155-induced mutator activity is not very sensitive to the basal level of mutation rate (i.e., to the integrity of the DNA safeguarding machinery) and that miR-155 targets additional transcripts implicated in DNA repair and/or genome stability.

Inflammatory Stimuli Up-Regulate miR-155 in Breast Cancer Cells.

Human cell lines were screened for the effects of proinflammatory environment on miR-155 expression. Colon cancer cell lines (SW480, SW620, HCT15, HCT116, and RKO) were included because a fraction of colorectal cancers appear linked to the inflammatory environment. Breast (MDA-MB-231, T47D, 453, 436, and MCF7) and lung cancer (A459) cell lines were included because miR-155 is up-regulated in these types of cancers, and four other cell lines were included for comparison.

Figure 2A:
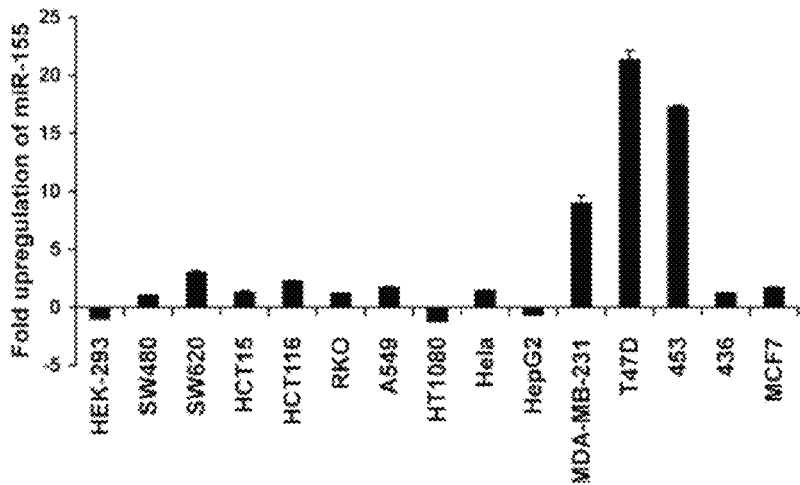
FIGS. 2A-2D. Proinflammatory environment increases the mutation rates in MDA-MB-231 cells and the frequency of mutant colonies in T47D cells.

Cells were treated overnight with the supernatant of LPS stimulated human THP-1 monocytic cells, namely LPS-stimulated macrophage-conditioned medium (LSMCM), which contains many inflammatory cytokines such as TNF, IL-6, IL-8, and IL1-β. Based on quantitative RT-PCR (qRT-PCR) analyses, miR-155 expression in colon and lung cancer cell lines was affected only slightly by LSMCM (FIG. 2A).

In contrast, miR-155 levels increased by 9-, 17-, and 21-fold in MDA-MB-231, BC-453, and T47D breast cancer cell lines, respectively. The inventor also analyzed the expression of miR-155a, a microRNA that is up-regulated in certain tumors and in LPS-challenged THP-1 cells, since it is now believed by the inventor herein that miR-155a controls the termination of the immune response. In sharp contrast with miR-155, the highest miR-155a levels were found in HCT15 and HCT116 colon cell lines (not shown), indicating that the up-regulation of miR-155 and miR-155a by inflammatory stimuli occurs independently in the above cancer cell lines and likely is tissue specific.

Figure 2B:
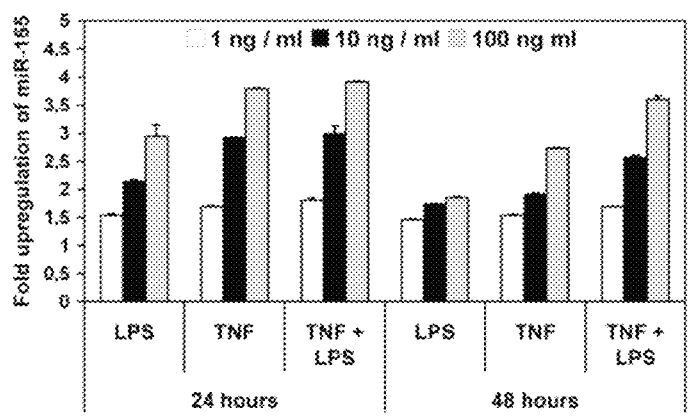

Because both TNF and LPS can induce miR-155, the inventor analyzed the effects of these two molecules in MDA-MB-231 cells. It was found that stimulation with either TNF or LPS or with both increased miR-155 expression (FIG. 2B). The inventor therefore used TNF/LPS to mimic the effects of a proinflammatory environment.

Inflammatory Stimuli Enhance the Mutation Rate.

In MDA-MB-231 cells without stimulation, the mutation rate was calculated to be $0.69\times10^{-7}$ mutations per cell per generation, a value similar to that previously found in SW480 cells ($0.75\times10^{-7}$). The estimated mutation rate was based on the average mutant frequency and population doubling. Of note, both MDAMB-231 and SW480 cells have intact DNA-repair machinery, unlike HCT116 cells. Mutant frequencies already had became significantly different (P=0.038) 3 d after treatment, with mutation rate increasing by 2.52-fold to $1.73\times10^{-7}$ mutations per cell per generation (FIG. 2C) in TNF/LPS-treated MDA-MB-231 cells vs. untreated control cells. The treatment lowered the rate of cell proliferation, likely because TNF induces growth arrest in breast cancer cells. Accordingly, one or two LSMCM stimulations of T47D cells increased the frequency of 6-TG-resistant colonies by 50% and 150%, respectively (FIG. 2D).

Thus, proinflammatory signals resulting in the up-regulation of miR-155 expression induce a significant, although moderate, mutator phenotype, which might be enhanced with chronic inflammation.

Characterization of HPRT Mutants.

The inventor then analyzed HPRT mutations found in cDNAs prepared from RNA extracted from T47D, HCT116, and MDA-MB-231 6-TG-resistant colonies to determine the mutation signature (FIG. 11—Table S1 and FIG. 12—Table S2).

HPRT mutations from doxycycline-treated HCT116 cells displayed single base deletions or insertions of the type generally found in DNA MMR-deficient cells. The majority displayed a frameshift, transition, and transversion mutation signature consistent with an MMR defect. There also was an increase in insertions and exon deletions with miR-155 overexpression; this increase generally has been ascribed to altered recombination repair. In contrast, deletion mutations consistent with recombination repair defects accounted for the majority of HPRT mutations in LSMCM-stimulated T47D cells and doxycycline treated MDA-MB-231 cells, regardless of conditions (FIG. 11—Table S1 and FIG. 12—Table S2). These results are consistent with a role for recombination repair, exemplified by breast cancer 1 (BRCA1) and breast cancer 2 (BRCA2) mutations, in these breast tumor cell lines. Of note, these types of mutations have been found previously in several T-cell leukemic cell lines. However, the inventor noted a modest increase in transitions and transversions consistent with decreased MMR in these cells.

Overexpression of miR-155 Enhances Cell Proliferation.

Figure 3A:
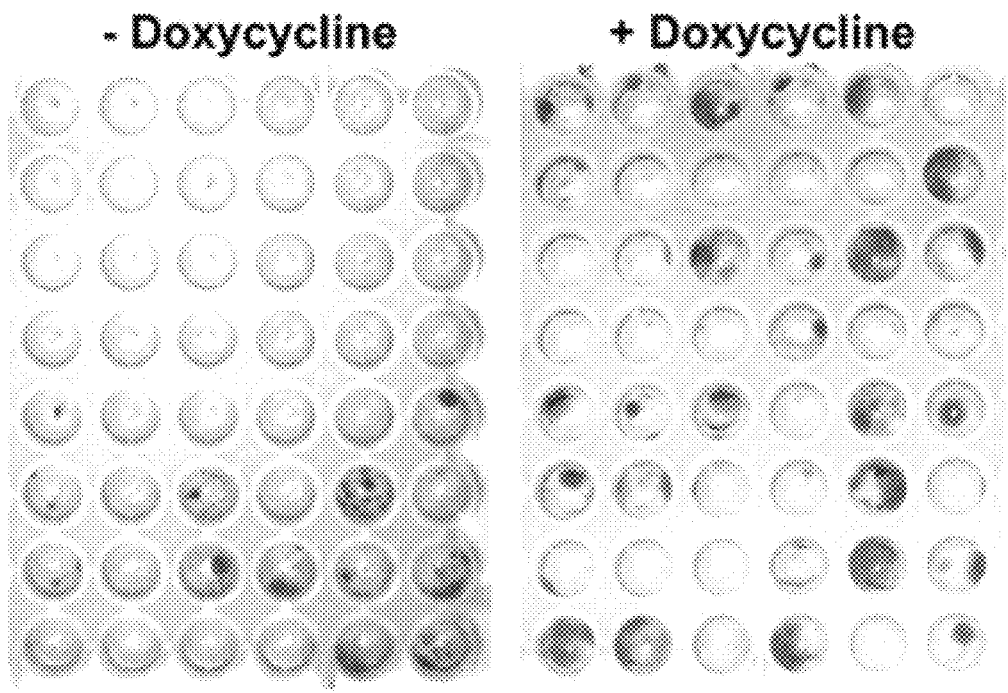
FIGS. 3A-3D. Elevated miR-155 levels increase the rate of proliferation by targeting WEE1 transcripts.

Remarkably, miR-155 up-regulation increased the size of HCT116 (FIG. 3A) and MDA-MB-231 HPRT mutant colonies and allowed them to appear earlier during the selection process. Based on a forward scatter comparison, larger colonies of MDA-MB-231 clone 19B, that presented a 32-fold up-regulation of miR-155 after doxycycline treatment, did not arise from the presence of larger cells (not shown).

Figure 3C:
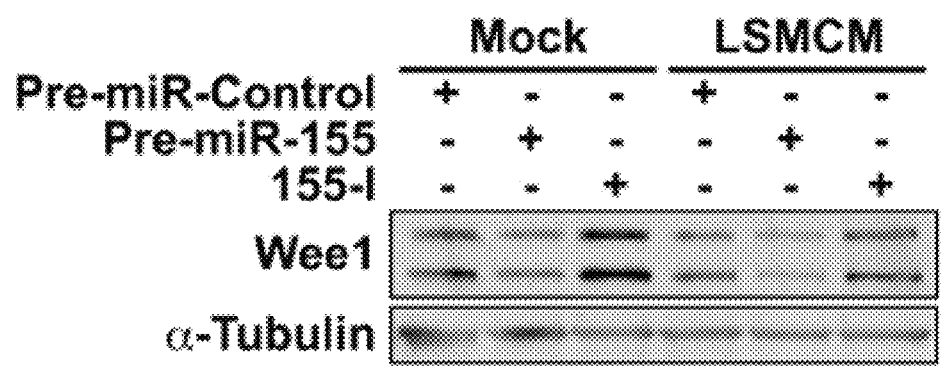
Figure 3D:
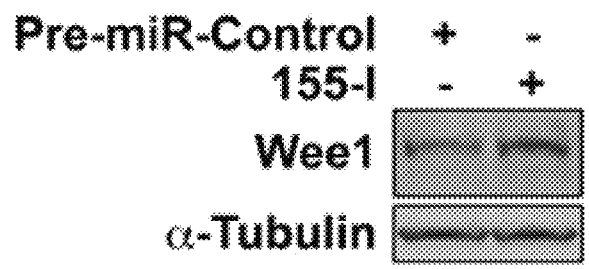
Figure 3B:
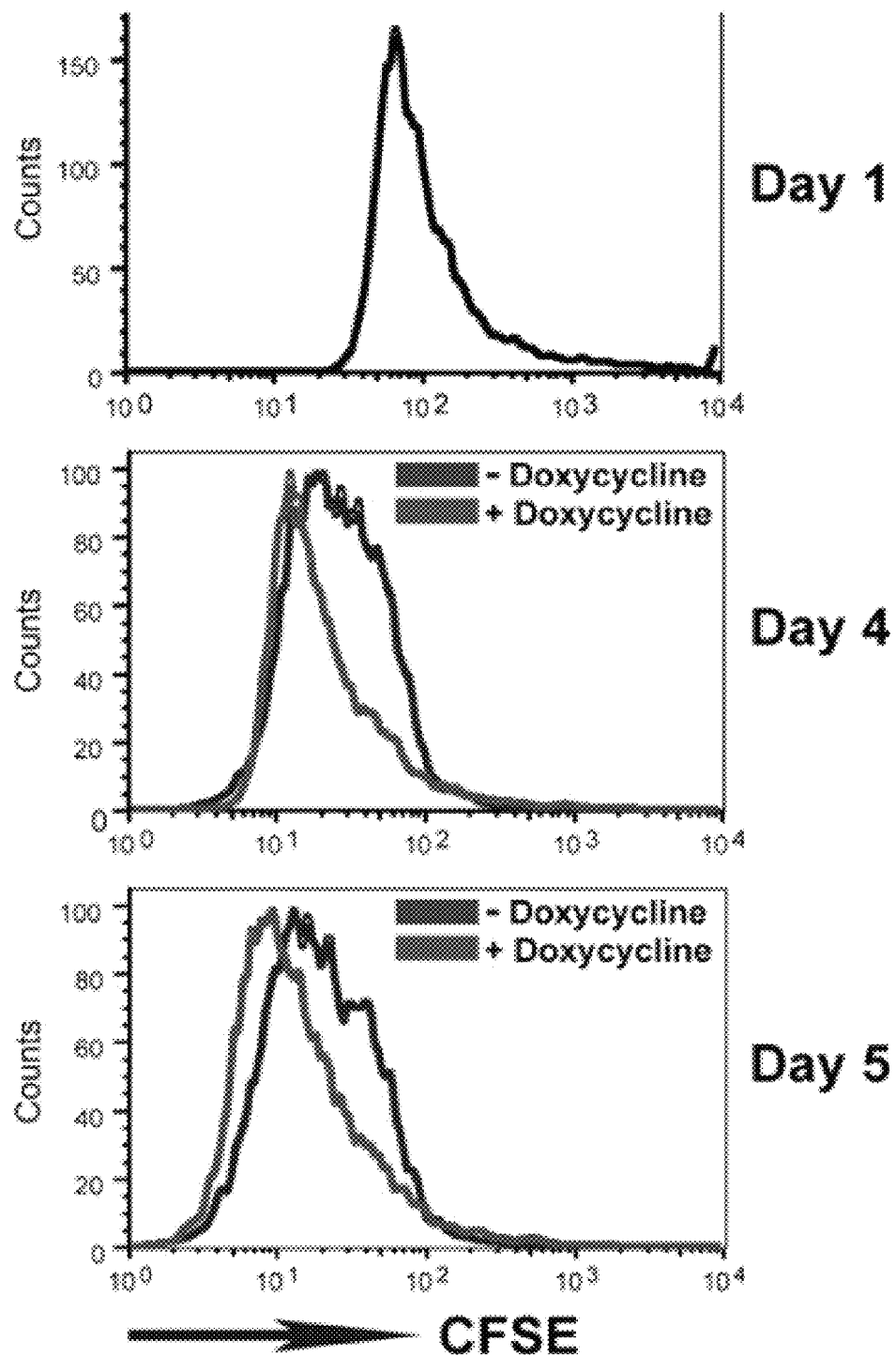

In contrast, carboxyfluorescein succinimidyl ester (CFSE) staining suggested that these cells underwent at least one extra round of cell division within 4-5 d as compared with untreated cells (FIG. 3B). These results correlate with reports showing that miR-155 promotes proliferation in transgenic mice. Thus, the larger size of HPRT mutant colonies overexpressing miR-155 probably arises from enhanced cell proliferation.

MiR-155 and Inflammatory Environment Down-Regulate WEE1, a Cell-Cycle Inhibitor.

Figure 6:
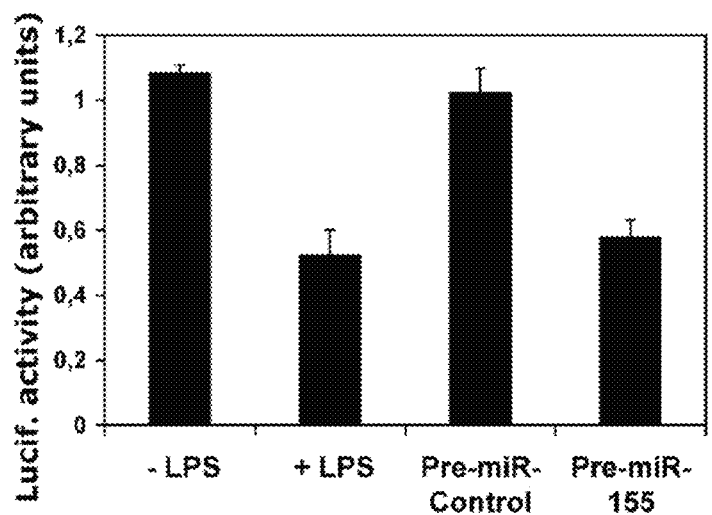
FIG. 6. miR-155 targets the WEE1 3' UTR. T47D cells transfected with a reporter construct containing the 3' UTR of WEE1 downstream of the luciferase coding region were treated with an unstimulated macrophage-conditioned medium (−LPS) or with LSMCM (+LPS) or were transfected with premiR-Control or premiR-155. Results were normalized to *Renilla* luciferase. Values represent mean±SD (n=5).

While not wishing to be bound by theory, the inventor herein now believes that miR-155 enhances cell proliferation by targeting cell-cycle regulators. Indeed, in T47D cells, both LSMCM treatment and miR-155 overexpression reduced the levels of WEE1, a kinase that catalyzes the inhibitory tyrosine phosphorylation of Cdc2/cyclin B, blocking cell-cycle progression at the G2/M phase (FIG. 3C). In contrast, an antisense miR-155 inhibitory RNA (155-I) increased WEE1 accumulation. Both LSMCM and miR-155 overexpression also reduced the expression of a luciferase reporter construct containing the WEE1 3' UTR (FIG. 6).

Accordingly, 155-I increased Wee1 levels in primary B cells isolated from Eµ-miR-155 transgenic mice that overexpress miR-155 in B-cell lineage, thus confirming that Wee1 is a bona fide miR-155 target. Taken together, these results show that inflammatory stimuli down-regulate WEE1 through upregulation of miR-155. Because WEE1 depletion rapidly induces DNA damage in newly replicated DNA, these results show that miR-155 overexpression may shorten the period required for selection of cancer-associated mutations. Furthermore, Affymetrix microarrays revealed that transcripts coding for several factors controlling cell cycle, DNA repair, and genome stability were affected by LSMCM in both T47D and MDA-MB-231 cell lines (FIG. 10—Table 2). This result shows that the ability of inflammatory stimuli to induce defective checkpoints and genomic instability, similar to miR-155, might contribute to tumorigenesis.

Discussion

In this example, the mutator activity of miR-155 and of the miR-155-related proinflammatory environment were analyzed. Cells in which inflammatory stimuli resulted in the up-regulation of miR-155 showed a two- to threefold increase in the mutation rate as deduced by HPRT assay.

Furthermore, inducible expression of miR-155 resulted in a similar increase in mutation rate, showing that the up-regulation of the mutation rate by the inflammatory stimuli is miR-155 dependent. The mutation rate was not increased in cells in which inflammatory stimuli up-regulated only miR-155, another microRNA implicated in the innate immune response (data not shown.

Although miR-155 levels in MDA-MB-231 cells were increased constantly by 12- and 32-fold during doxycycline treatment, they increased transiently by only plus or minus fourfold after LPS/TNF treatment (FIG. 1B and FIG. 2B).

Figure 2C:
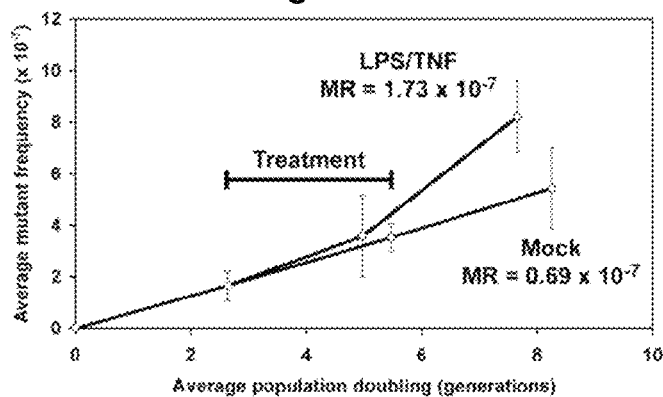
Figure 2D:
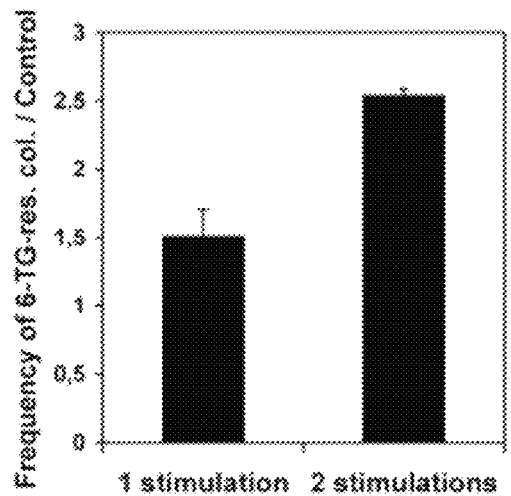

Nevertheless, the mutation rate increased by 1.56- to 3.47-fold after doxycycline treatment and by 2.52-fold after TNF/LPS treatment (FIG. 1B and FIG. 2C). This result shows that increased miR-155 levels resulting from chronic inflammation, autoimmune diseases, or the deregulation of endogenous genetic circuitries with the onset of cancer may produce a significant mutator phenotype. These results also show that other inflammatory signaling pathways may work in synergy or in parallel with miR-155.

Of note, miR-155 targets tumor suppressor genes such as Fas-associated via death domain (FADD), Jumonji AT-rich interactive domain 2 (JARID2), and Src homology 2-containing inositol phosphatase-1 (SHIP1) (FIG. 13—Table S3). In addition, other microRNAs with mutator activity are up-regulated by LPS signaling. The increased mutation rate in HCT116 cells that lack the hMLH1 DNA repair enzyme showed that this increase occurs through miR-155 targeting of other transcripts involved in DNA repair, recombination, or cell-cycle checkpoints. Because mutations accumulate during the S phase, when the replication of the DNA takes place right before the G2/M check point, the inventor looked for transcripts that are predicted targets of miR-155 and act as inhibitors of G2/M transition because their reduced expression might be associated with an increased mutation rate. In addition, these transcripts can act as targets of LPS/TNF signaling. It is to be understood that the inventor first concentrated on WEE1 kinase, because it fulfilled all these criteria.

In T47D cells, overexpression of miR-155 or treatment with LSMCM resulted in the down-regulation of WEE1 expression. By targeting WEE1 and consequently facilitating G2/M transition, miR-155 allows cells that have not yet repaired the DNA to proceed to mitosis, resulting in accumulated mutations. Akt kinase also is known to function as a G2/M initiator and to inactivate WEE1 by phosphorylation, thus promoting the cell-cycle transition. Akt is implicated in LPS signaling by modulating the levels of miR-155, among other microRNAs. While not wishing to be bound by theory, the inventor herein now believes that oncogenic Akt and onco-inflammatory miR-155 cross talk at the level of WEE1 during inflammation. The inventor considers that the increased mutation rate associated with inflammatory signals is a combinatorial effect of miR-155 targeting of WEE1 and other DNA repair enzymes that are down-regulated by LPS and are either direct or indirect targets of miR-155. It is believed that cancer results from the accumulation of mutations in somatic cells, and this example shows that, by increasing the mutation rate, the inflammatory miR-155 is a key player in inflammatory-induced cancers in general.

The control of cell-cycle progression and DNA repair in eukaryotes are highly conserved. However, in the event of an infection the cells must respond quickly by producing cytokines, chemokines, and other inflammatory components of the immune defense. During this robust response, it is possible that the DNA repair machinery and cell-cycle checkpoints are put on hold. At this stage the up-regulation of miR-155 by inflammatory stimuli to clear the antigen quickly also results in an increased mutation rate. Furthermore, regardless of the primary cause of a mutation, there is a high probability that, in the event of an infection, the mutation will be fixed.

Figure 7:
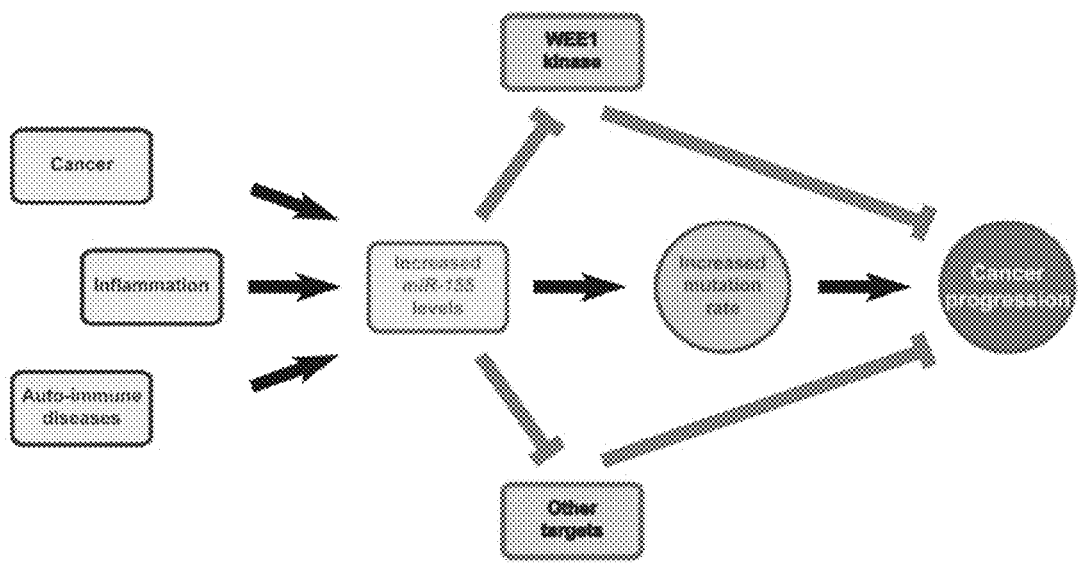
FIG. 7. Schematic representation showing that the up-regulation of miR-155 over a prolonged period as a consequence of chronic inflammation or the deregulation of endogenous genetic circuitries in cancer or other diseases may lead to higher mutation rates in vivo. It was found that the targeting of WEE1 by miR-155 would further extend DNA damage. The up-regulation of miR-155 also down-regulates tumor-suppressor factors and other factors controlling cell homeostasis (FIG. 10—Table 2 and FIG. 7). Taken together, these effects can shorten the process of malignant transformation and favor cancer progression.

While not wishing to be bound by theory, the inventor herein now we believes that simultaneous miR-155—driven suppression of a number of tumor suppressor genes combined with a mutator phenotype allows the shortening of the series of steps required for tumorigenesis and represents a model for cancer pathogenesis (FIG. 7).

Thus, the up-regulation of miR-155 by chronic inflammation appears to indicate at least one of the missing links between cancer and inflammation.

Materials and Methods

Cell Culture, Transfection, and Treatment.

Cells were grown following standard procedures. T47D cells were transfected using lipofectamine (Invitrogen). Unstimulated LSMCM were prepared from the supernatant of human THP-1 monocytic cells mock stimulated or stimulated with *Salmonella enteritidis* derived LPS (100 ng/mL, Sigma) for 6 h. THP-1 cells subsequently were centrifuged, and the supernatant was filtrated to eliminate any remaining cells.

T47D cells then were cultivated in the presence of unstimulated medium or LSMCM for 48 h. When needed, a second stimulation was conducted in the same way, after the cells had been allowed to recover 4 d in regular medium. TNF was obtained from Invitrogen. The B-cell line was established by purifying B cells from the spleen of an Eµ-miR-155 transgenic mouse using the isolation kit from R & D Systems. B cells subsequently were cultured for 2 wk in 100 ng/mL RPMI/15% FBS/LPS and for 3 more weeks without LPS. They were electroporated using the Amaxa kit (Lonza).

Retroviral Infection.

The Retro-X Tet-Advanced System (Clontech) was used according to the manufacturer's instruction. Clones stably expressing miR-155 were prepared from MDA-MB-231 cells and SW620 cells following manufacturers' instructions. In brief, cells were infected first with the pRetroX-tight-Pur-miR-155 response virus. Colonies resistant for puromycin then were infected with the pRetroX-Tet-On Advanced regulator virus and selected for resistance to both puromycin and Geneticin. Throughout the selection process, cells were grown in medium containing Tet-FBS (Clontech) that does not contain any tetracycline residue. A fraction of double-resistant clones then was treated with 500 ng/mL doxycycline for 2 d before miR-155 expression was analyzed by qRT-PCR. HCT116 cells were transiently infected with a viral suspension containing both the pRetroX-Tet-On Advanced regulator vector and the pRetroX-tight-Pur response vector containing the construct of interest and then were left to recover for 2 d in regular medium before the addition of doxycycline.

Preparation of Expression Constructs.

The WEE1 reporter construct was prepared by inserting the 3' UTR of human WEE1, prealably amplified by PCR from HEK-293 cells' genomic DNA, downstream of the Luciferase gene in the XbaI site of the pGL3-Control vector (Promega). The mature miR-155 and miR-155 precursor (premiR-155) were cloned in the pRetroX-tight-Pur vector following digestion by NotI and EcoRI of double-strand DNAs prepared by reannealing the following primers:

```
miR-155 mature:
V155MatForward:
                                        [SEQ ID NO: 1]
5'-ATAGCGGCCGCTTAATGCTAATCGTGATAGGGGTGAATTCGCG-3'
and V155-MatReverse:
                                        [SEQ ID NO: 2]
5'-CGCGAATTCACCCCTATCACGATTAGCATTAAGCGGCCGCTAT-3';

premiR-155:
V155PreForward:
                                        [SEQ ID NO: 3]
5'ATAGCGGCCGCCTGTTAATGCTAATCGTGATAGGGGTTTTTGCCTCC AACTGACTCCTACATATTAGCATTAACAGGAATTCGCG-3'
and V155PreReverse:
                                        [SEQ ID NO: 4]
5'CGCGAATTCCTGTTAATGCTAATATGTAGGAGTCAGTTGGAGGCAAA

AACCCCTATCACGATTAGCATTAACAGGCGGCCGCTAT-3'.
```

Selection of 6-TG-Resistant Colonies.

To eliminate any preexisting HPRT mutants, cells were grown in 100 µM hypoxanthine, 400 nM aminopterin, and 16 µM thymidine (HAT medium) Sigma) for 3 d. The MDA-MB-231 cells used for the experiment reported in FIG. 2C were cleansed in HAT medium for 15 d. After three washes, cells were resuspended and incubated in regular medium for another 3 d. T47D, HCT116, SW620, or MDA-MB-231 cells then were treated with macrophage-conditioned medium or doxycycline as required. Two days later, HCT116 cells were plated in 96-well round-bottomed plates (1,000 cells per well), and T47D, SW620, or MDA-MB-231 cells were plated in 48-well plates (106 cells per plate) in selection medium containing 30 µM 6-TG. HPRT mutants then were selected based on their resistance to 6-TG. During the selection process, cells containing the retroviral constructs were constantly stimulated with doxycycline. After 2-3 wk of selection on 6-TG medium (with 6-TG-containing medium changed every 3 d), plates were stained with crystal violet to allow the visualization and counting of 6-TG-resistant colonies.

Estimation of Mutation Rates.

Figure 8:
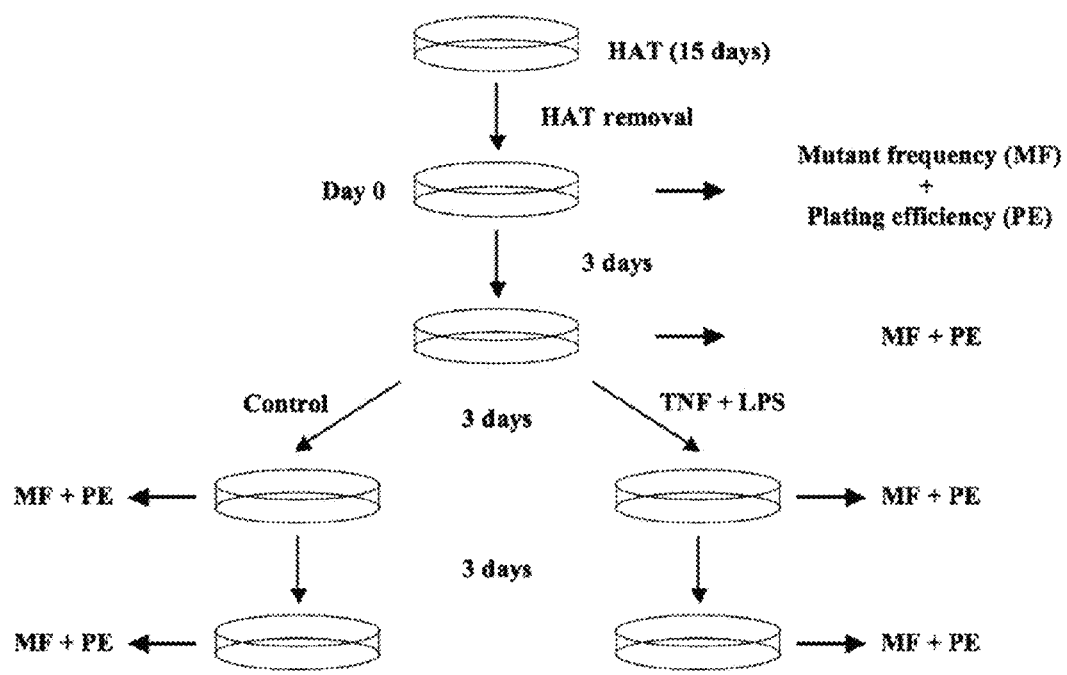
FIG. 8. Schematic representation summarizing the experimental design of FIG. 2C. HAT, 100 μM hypoxanthine, 400 nM aminopterin, 16 μM thymidine.

For the experiments with SW620 and MDA-MB-231 stable clones (FIG. 1 and FIG. 11—Table S1), mutation rates were adjusted for cell growth and were estimated based on a modified version of fluctuation analysis. The cell growth-adjusted mutation rate was analyzed based on the formula $r=f\times\tau/t$, where "f" is the mutation frequency (mutations per cell), "$\tau$" is 1/cell division rate (in cell divisions per day), and "t" is the length of miR-155 induction (in days). For the experiments with MDA-MB-231 cells (FIG. 2C), the estimated mutation rate was based on the average mutant frequency and population doubling according to the schema shown in FIG. 8.

Mutant frequency and population doubling were estimated at each of the steps shown thereafter (i.e., right after HAT cleansing, 3 d after HAT cleansing, 3 d after mock (control) or TNF/LPS treatment, and 3 d after the end of the treatment). Cells were plated in 6-TG-supplemented medium at a density of $1.5\times10^6$ cells per 10-cm dish. Additionally, plating efficiency (PE) at the time of selection was determined by plating 500 cells per 10-cm dish in triplicate in RPMI medium without hypoxanthine. Cells were incubated for 14-20 d, and colonies were visualized by staining with 0.5% crystal violet in 4% paraformaldehyde (Sigma). Mutant frequency (MF) then was determined as follows: $MF=a/(60\times10^6\times[b/1.5\times10^3])$, where "a" is the total number of 6-TG-resistant colonies, and "b" is the total number of colonies on all three plates. PE and the exact number of cells subcultured were used to calculate population doubling (PD) as follows: $PD=(\ln[\text{total number of cells}]-\ln[\text{number of cells plated}\times PE])/\ln 2$. Mutation rate was estimated by plotting the observed mutant frequencies as a function of PD and calculating the slope by linear regression. This slope yields the mutation rate (mutations per cell per generation).

Analysis of HPRT cDNA Mutations.

The 6-TG-resistant colonies from miR-155-Off and miR-155-On infected cells were selected randomly as representative mutant clones. Clones were expanded for 1 wk before RNA extraction. Total RNA was reverse-transcribed using the High Capacity cDNA Reverse Transcription Kit with RNase Inhibitor from Applied Biosystems. HPRT cDNAs (nucleotides 123-1,110) were amplified subsequently by PCR using the Advantage 2 Polymerase Mix from Clontech, with the forward primer 5'-GCGCGCCGGCCGGCTCCGTT-3' [SEQ ID NO:5] and the reverse primer 5'-GGCGATGT-CAATAGGACTCCAGATG-3' [SEQ ID NO:6].

In most cases, the PCR products were cloned in the TOPO vector (Invitrogen) and subsequently sequenced following plasmid purification. In other cases, the PCR products were purified using the PCR purification kit from Qiagen and were directly sequenced at the sequencing facility at Ohio State University using the primers 5'-GCCGGCCGGCTCCGT-TATGG-3' [SEQ ID NO:7] and 5'-ATGTCAATAGGACTC-CAGATG-3' [SEQ ID NO:8].

Isolation of RNAs and qRT-PCR.

RNA was extracted with TRIzol (Invitrogen) and subsequently subjected to DNase digestion (Turbo-DNase; Ambion). MiR-155 qRT-PCR was performed using TaqMan MicroRNA Assays (Applied Biosystems). Values were normalized using RNU-44. Real-time PCR was run in triplicate from three different cDNAs.

FACS Analysis.

CFSE was purchased from Molecular Probes/Invitrogen. CFSE staining was carried out using manufacturer's protocol.

Cells were fixed in 1% paraformaldehyde before analyses. Flow cytometry analyses were performed at the corresponding facility of Ohio State University. Data were analyzed using the software program FlowJo (Tree Star, Inc.).

Western Blots.

Cells were lysed 48 h after transfection or electroporation. Anti-WEE1 and anti-α-tubulin antibodies were from Cell Signaling Technology.

Affymetrix Microarray Analyses.

RNAs extracted with TRIzol (Invitrogen) were subsequently subjected to DNase digestion (Turbo-DNase; Ambion). Affymetrix microarray analyses were done at the Ohio State University microarray facility.

Luciferase Assays.

Cells plated in 12-well plates (1×106 cells per plate) were transfected with 0.4 μg of DNA (pGL3-control vector or WEE1 reporter constructs; Promega), 20 ng of *Renilla* luciferase control vector (pRL-TK; Promega), and 50 nM of either a premiR control (premiR Precursor Molecule-Negative Control #1; Ambion), premiR-155 (miR-155 precursor; Ambion), or 155-I (an antisense miR-155 inhibitory RNA; Ambion). Assays were performed 48 h after transfection using the Dual Luciferase Reporter Assay System (Promega). Firefly luciferase activity was normalized to *Renilla* luciferase activity.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

What is claimed is:

1. A method for modulating WEE1 kinase expression levels in an inflammation-related solid cancer target cell, comprising: administering a microRNA-155 (miR-155) antagonist to the target cell in an amount sufficient to modulate WEE1 kinase levels, and wherein the WEE1 levels are increased after administration.

2. The method of claim 1, wherein the miR-155 antagonist comprises a modified oligonucleotide consisting of 12 to 30 linked nucleosides, wherein the nucleobase sequence of the modified oligonucleotide is complementary to a sequence at least 80% identical to mature miR-155, pre-miR-155, a miR-155 seed sequence, or a sequence fully complementary to the sequence of mature miR-155, pre-miR-155, or miR-155.

3. The method of claim 1, wherein administering a miR-155 antagonist comprises: administering an antisense miR-155 expression vector to a target cell; and expressing an antisense miR-155 in the target cell.

4. The method of claim 1, wherein the target cell is a breast cancer or precancerous cell.

5. The method of claim 1, wherein the target cell is a colon cancer or precancerous cell.

6. The method of claim 1, wherein the target cell is a gastric cancer or precancerous cell.

7. The method of claim 1, wherein the target cell is a lung cancer or precancerous cell.

8. The method of claim 2, wherein the modified oligonucleotide has no more than two mismatches to the nucleobase sequence of mature miR-155.

9. The method of claim 1, comprising contacting the target cell with an antisense miR-155 inhibitory RNA (155-I), and wherein the WEE1 levels are increased after 155-I treatment.

10. A method of reducing spontaneous mutation rate of an inflammation-related solid cancer target cell in a subject in need thereof, comprising: contacting the target cell with an antisense miR-155 inhibitory RNA (155-I) in an amount sufficient to increase WEE1 levels, wherein the WEE1 levels are increased after 155-I treatment.

11. The method of claim 10, wherein the miR-155 inhibitory RNA (155-I) comprises a miR-155 antagonist compound.

12. The method of claim 10, wherein the miR-155 inhibitory RNA (155-I) binds to at least one oligonucleotide selected from the group consisting of:

a mature miR-155 oligonucleotide, a pre-miR-155 oligonucleotide, and a miR-155 seed sequence.

13. The method of claim 12, wherein the miR-155 inhibitory RNA comprises a modified oligonucleotide consisting of 12 to 30 linked nucleosides, wherein the nucleobase sequence of the modified oligonucleotide is complementary to a sequence at least 80% identical to mature miR-155, pre-miR-155, a miR-155 seed sequence, or a sequence fully complementary to the sequence of mature miR-155, pre-miR-155, or miR-155.

14. The method of claim 10, wherein contacting the cell comprises: administering an antisense miR-155 expression vector to the target cell; and expressing an antisense miR-155 in the target cell.

15. The method of claim 10, wherein contacting the cell comprises: administering a miR-155 inhibitory RNA (155-I) expression vector to the target cell; and expressing 155-I in the target cell.

16. The method of claim 15, wherein the miR-155 inhibitory RNA (155-I) expression vector comprises a nucleic acid sequence encoding 155-I operably linked to a promoter.

17. The method of claim 10, wherein the cell is a breast cancer or precancerous cell.

18. The method of claim 10, wherein the cell is a colon cancer or precancerous cell.

19. The method of claim 10, wherein the cell is a gastric cancer or precancerous cell.

20. The method of claim 10, wherein the cell is a lung cancer or precancerous cell.

21. The method of claim 13, wherein the modified oligonucleotide has no more than two mismatches to the nucleobase sequence of mature miR-155.

22. The method of claim 10, wherein the subject is human.

23. A method of preventing the onset of an inflammatory-related breast cancer, comprising: normalizing WEE1 levels by reducing inflammatory-related up-regulation of miR-155 in a subject in need thereof, by administering an antisense miR-155 inhibitory RNA (155-I) to a breast cell such that the resulting expression of miR-155 is normalized or elevated by no more than two-fold as compared with a control level of miR-155 expression, and wherein WEE1 levels are increased after 155-I treatment.

24. The method of claim 10, wherein the cell further comprises a cell exhibiting at least one mutation selected from the group comprising: the mutations listed in FIG. 12 (SEQ ID NOS: 9-123).

25. The method of claim 1, wherein the administration of the miR-155 antagonist reduces the miR-155 level in the target cell from greater than four-fold to less than two-fold as compared with a control level of miR-155, wherein the control level is derived from a non-cancerous cell, and wherein the WEE1 levels are increased after miR-155 antagonist administration.

26. The method of claim 10, wherein the administration of the 155-I reduces the miR-155 level in the cancer cell from greater than four-fold to less than two-fold as compared with a control level of miR-155, wherein the control level is derived from a non-cancerous cell, and wherein the WEE1 levels are increased after 155-I administration.

* * * * *